United States Patent
Jimbo et al.

(10) Patent No.: US 12,240,842 B2
(45) Date of Patent: Mar. 4, 2025

(54) COMPOUND, TAUTOMER OF COMPOUND OR SALT OF COMPOUND OR TAUTOMER, METHOD FOR PRODUCING SAME, COLORING COMPOSITION, DYEING METHOD, AND DYED ARTICLE

(71) Applicant: FUJIFILM CORPORATION, Tokyo (JP)

(72) Inventors: Yoshihiro Jimbo, Shizuoka (JP); Yasuhiro Ishiwata, Shizuoka (JP); Motoki Ueda, Shizuoka (JP); Yoshihiko Fujie, Shizuoka (JP)

(73) Assignee: FUJIFILM CORPORATION, Tokyo (JP)

( * ) Notice: Subject to any disclaimer, the term of this patent is extended or adjusted under 35 U.S.C. 154(b) by 59 days.

(21) Appl. No.: 18/298,376

(22) Filed: Apr. 11, 2023

(65) Prior Publication Data
US 2023/0242523 A1 Aug. 3, 2023

Related U.S. Application Data

(63) Continuation of application No. PCT/JP2021/037957, filed on Oct. 13, 2021.

(30) Foreign Application Priority Data

Oct. 14, 2020 (JP) .................... 2020-173290
Dec. 25, 2020 (JP) .................... 2020-217653

(51) Int. Cl.
| | |
|---|---|
| *C07D 419/00* | (2006.01) |
| *C07D 231/38* | (2006.01) |
| *C07D 403/12* | (2006.01) |
| *C07D 417/12* | (2006.01) |
| *C09B 27/00* | (2006.01) |
| *C09B 33/044* | (2006.01) |
| *C09B 67/44* | (2006.01) |

(52) U.S. Cl.
CPC ......... *C07D 417/12* (2013.01); *C07D 231/38* (2013.01); *C07D 403/12* (2013.01); *C09B 27/00* (2013.01); *C09B 33/044* (2013.01); *C09B 67/0083* (2013.01)

(58) Field of Classification Search
CPC .. C07D 417/12; C07D 231/38; C07D 403/12; C07D 403/14; C09B 27/00; C09B 33/044; C09B 67/0083; C09B 33/02; C09B 33/04; C09B 33/24; D06P 1/04; C09D 11/037; C09D 11/328
USPC .......................................................... 8/692
See application file for complete search history.

(56) References Cited

U.S. PATENT DOCUMENTS

| | | | | |
|---|---|---|---|---|
| 2,446,662 A | * | 8/1948 | Nies ........................ | C09B 45/06 534/769 |
| 5,739,348 A | * | 4/1998 | Vishwakarma ...... | C07D 249/20 548/259 |
| 6,214,519 B1 | * | 4/2001 | Suzuki ................ | G11B 7/2472 430/270.16 |
| 2002/0034605 A1 | | 3/2002 | Matsui et al. | |
| 2003/0045122 A1 | * | 3/2003 | Lee ......................... | C09B 45/22 438/758 |
| 2009/0081401 A1 | | 3/2009 | Matsui et al. | |
| 2017/0121527 A1 | | 5/2017 | Haleem et al. | |

FOREIGN PATENT DOCUMENTS

| | | | | |
|---|---|---|---|---|
| CN | 106243775 A | | 12/2016 | |
| CN | 113444378 A | | 9/2021 | |
| JP | 10044606 A | * | 2/1998 | ............. B41M 5/26 |
| JP | 2002-074740 A | | 3/2002 | |
| JP | 2017-515930 A | | 6/2017 | |

OTHER PUBLICATIONS

STIC Search Report dated Jul. 18, 2024.*
Kumar, Ashok et al, "Exploration of antimicrobial and antioxidant potential of newly synthesized 2,3-disubstituted quinazoline-4(3)-ones", Bioorganic & Medicinal Chemistry Letters, Elsevier, Amsterdam NL, vol. 21, No. 14, May 10, 2011, pp. 4353-4357, (Retrieved on May 15, 2011).
Korol'kova, V.S. et al.: "Synthesis and spectrophotometric study of 5-benzoyl-2-(3,4-dihydroxyphenyl)azo-4-trifluoromethylthiazole", Latvijas Psr Zinatnu Akademijas Vestis, Kimijas Serija, No. 1, Jan. 1, 1989, pp. 98-101.
Extended European Search Report dated Feb. 8, 2024, issued in corresponding EP Patent Application No. 21880167.8.
English language translation of the following: Office Action dated May 13, 2024 from the SIPO in a Chinese patent application No. 202180069974.3 corresponding to the instant patent application.
(Continued)

*Primary Examiner* — Eisa B Elhilo
(74) *Attorney, Agent, or Firm* — SOLARIS Intellectual Property Group, PLLC

(57) ABSTRACT

Provided are a compound represented by Formula 1, a tautomer of the compound or a salt of the compound or the tautomer, a coloring composition and a dyed article containing the compound represented by Formula 1, the tautomer of the compound, or the salt of the compound or the tautomer, and a dyeing method using the compound represented by Formula 1, the tautomer of the compound, or the salt of the compound or the tautomer. In Formula 1, X, R, Ar, n, and m1 are as defined in the specification.

Formula 1

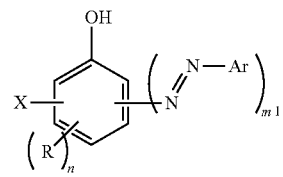

13 Claims, No Drawings

(56) References Cited

OTHER PUBLICATIONS

C.T. Keerthi Kumar et al., "Synthesis, Characterization and Antimicrobial Activity of Heterocyclic Azodyes Derived from Thiadiazole", Chemical Science Transactions, 2013, 2(4), 1346-1351, scheme 1, p. 1348, lines 27-32.

E.V. Sadchikova et al., "Reactivity of diazoazoles and azolediazonium salts in C-azo coupling reactions", Russian Chemical Bulletin, 2005, 54(2), 354-365, scheme 2.

International Search Report issued in International Application No. PCT/JP2021/037957 on Dec. 28, 2021.

Written Opinion of the ISA issued in International Application No. PCT/JP2021/037957 on Dec. 28, 2021.

\* cited by examiner

COMPOUND, TAUTOMER OF COMPOUND OR SALT OF COMPOUND OR TAUTOMER, METHOD FOR PRODUCING SAME, COLORING COMPOSITION, DYEING METHOD, AND DYED ARTICLE

CROSS-REFERENCE TO RELATED APPLICATIONS

This application is a continuation application of International Application No. PCT/JP2021/037957, filed Oct. 13, 2021, which is incorporated herein by reference. Further, this application claims priority from Japanese Patent Application No. 2020-173290, filed Oct. 14, 2020, and Japanese Patent Application No. 2020-217653, filed Dec. 25, 2020, which are incorporated herein by reference.

BACKGROUND OF THE INVENTION

1. Field of the Invention

The present disclosure relates to a compound, a tautomer of the compound or a salt of the compound or the tautomer, a method for producing the compound, the tautomer of the compound, or the salt of the compound or the tautomer, a coloring composition, a dyeing method, and a dyed article.

2. Description of the Related Art

In the related art, since an azo coloring agent usually has various visible light absorptions, the azo coloring agent has been used as a coloring agent in various fields. For example, the azo coloring agent has been used in various fields such as coloring of synthetic resins, printing inks, coloring agents for sublimation type thermal transfer materials, ink jet inks, and coloring agents for color filters.

In recent years, a color image has been mainstream as an image recording material, and uses of the coloring agent has been diversified. Specifically, the coloring agent has been widely used in ink jet type recording materials, thermal transfer type recording materials, electrophotographic type recording materials, transfer type silver halide photosensitive materials, and printing inks. In addition, a color filter is used to record or reproduce a color image in an imaging element of an imaging device, such as a charge-coupled device (CCD) and a complementary metal oxide semiconductor (CMOS), and in a liquid crystal display (LCD) and a plasma display panel (PDP) as a display. In these color image recording materials or color filters, colorants (dyes or pigments) of three primary colors using a so-called additive color mixing method or subtractive color mixing method have been used in order to reproduce or record a full color image.

In addition, various dyeing agents for dyeing fibers and the like have been known for a long time, and in recent years, many hair dyeing agents for dyeing hair and the like have been developed.

The hair dyeing agents can be classified according to dyes to be used or the presence or absence of a decolorizing effect on melanin. Typical examples of the hair dyeing agents include a two-agent type permanent hair dyeing agent formed of a first agent which contains an alkaline agent, an oxidation dye, and optionally a direct dye such as a nitro dye, and a second agent which contains an oxidizing agent; and a one-agent type semi-permanent hair dyeing agent that contains an organic acid or an alkaline agent and at least one of as an acid dye, a basic dye, or a direct dye such as a nitro dye.

Examples of the azo coloring agent in the related art include coloring agents disclosed in JP2017-515930A.

SUMMARY OF THE INVENTION

However, there may be a case where a coloring agent having a special hue other than yellow, magenta, and cyan in the related art is required. For example, a coloring agent having low chroma saturation or a coloring agent having a wide absorption waveform and absorption over the entire visible region is required. Therefore, there is currently no robust colorant which has these preferred absorption characteristics and can withstand various use conditions and environmental conditions, and improvement is strongly desired.

An object to be achieved by an aspect of the present invention is to provide a novel compound, a tautomer of the compound, or a salt of the compound or the tautomer.

An object to be achieved by another aspect of the present invention is to provide a coloring composition with a hue having low chroma saturation.

An object to be achieved by still another aspect of the present invention is to provide a method for producing the compound, the tautomer of the compound, or the salt of the compound or the tautomer, and a dyeing method and a dyed article dyed with the compound, the tautomer of the compound, or the salt of the compound or the tautomer.

The methods for achieving the above-described objects include the following aspects.

<1> A compound represented by Formula 1, a tautomer of the compound, or a salt of the compound or the tautomer.

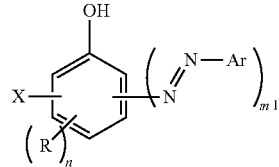

Formula 1

In Formula 1, X— represents $R^1O$—, $R^{2a}R^{2b}N$—, or $R^3S$—, $R^1$, $R^{2a}$, and $R^{2b}$ each independently represent a hydrogen atom or an alkyl group, and $R^3$ represents an alkyl group. In a case where X— is $R^{2a}R^{2b}N$—, $R^{2a}$ and $R^{2b}$ may be the same or different from each other, and $R^{2a}$ and $R^{2b}$ may be bonded to each other to form a nitrogen-containing hetero ring. R's each independently represent a substituent, n represents 0, 1, 2, or 3, and in a case where n represents 2 or 3, R's may be the same or different from each other. Ar represents an aromatic hydrocarbon group or a heterocyclic group, m1 represents 1, 2, or 3, and in a case where m1 represents 2 or 3, Ar's may be the same or different from each other. However, at least one of Ar's is a heterocyclic group.

<2> The compound, the tautomer of the compound, or the salt of the compound or the tautomer according to <1>, in which m1 is 2 or 3.

<3> The compound, the tautomer of the compound, or the salt of the compound or the tautomer according to <2>, in which m1 is 2.

<4> The compound, the tautomer of the compound, or the salt of the compound or the tautomer according to any one of <1> to <3>,
in which a bonding position of X— is a meta-position with respect to a hydroxy group.
<5> The compound, the tautomer of the compound, or the salt of the compound or the tautomer according to any one of <1> to <4>,
in which R is a halogen atom, a hydroxy group, an alkyl group, an aryl group, an alkoxy group, an aryloxy group, an acyl group, an alkoxycarbonyl group, a carboxy group, a carbamoyl group, a cyano group, an acylamino group, a sulfonylamino group, an alkylthio group, an arylthio group, an alkylsulfonyl group, an arylsulfonyl group, or a sulfo group.
<6> The compound, the tautomer of the compound, or the salt of the compound or the tautomer according to any one of <1> to <5>,
in which the at least one of Ar's is a group represented by any of Formulae (A-1) to (A-28).

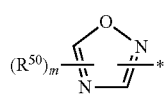
(A-25)

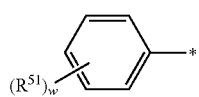
(A-26)

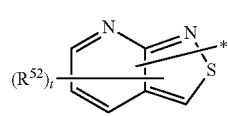
(A-27)

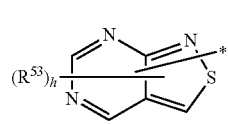
(A-28)

In Formulae (A-1) to (A-28), * represents a position bonded to an azo group in Formula 1, $R^{21}$ to $R^{27}$, $R^{29}$, $R^{31}$, and $R^{33}$ to $R^{53}$ each independently represent a halogen atom, an alkyl group, an aryl group, a heterocyclic group, a cyano group, a hydroxy group, a nitro group, an alkoxy group, an aryloxy group, an amino group, an acylamino group, an aminocarbonylamino group, an alkoxycarbonylamino group, an alkylsulfonylamino group, an arylsulfonylamino group, an alkylthio group, an arylthio group, a heterocyclicthio group, a sulfamoyl group, an alkylsulfonyl group, an arylsulfonyl group, an acyl group, an alkoxycarbonyl group, or a carbamoyl group, $R^{28}$, $R^{30}$, and $R^{32}$ each independently represent a hydrogen atom, a halogen atom, an alkyl group, an aryl group, a heterocyclic group, a cyano group, a hydroxy group, a nitro group, an alkoxy group, an aryloxy group, an amino group, an acylamino group, an aminocarbonylamino group, an alkoxycarbonylamino group, an alkylsulfonylamino group, an arylsulfonylamino group, an alkylthio group, an arylthio group, a heterocyclicthio group, a sulfamoyl group, an alkylsulfonyl group, an arylsulfonyl group, an acyl group, an alkoxycarbonyl group, or a carbamoyl group, adjacent groups among $R^{21}$ to $R^{53}$ may be bonded to each other to form a saturated or unsaturated 5- or 6-membered ring structure, a, p, q, r, and s represent an integer of 0 to 4, b and c represent an integer of 0 to 6, d, e, f, g, t, and u represent an integer of 0 to 3, h, i, j, k, l, and o represent an integer of 0 to 2, w represents an integer of 0 to 5, m represents 0 or 1, and two or more groups represented by $R^{21}$ to $R^{53}$ in a same molecule may be the same or different from each other.

<7> The compound, the tautomer of the compound, or the salt of the compound or the tautomer according to any one of <1> to <6>,
  in which the compound, the tautomer of the compound, or the salt of the compound or the tautomer is a bisazo coloring agent.

<8> A coloring composition comprising:
  the compound, the tautomer of the compound, or the salt of the compound or the tautomer according to any one of <1> to <6>.

<9> The coloring composition according to <8>, further comprising:
  an aqueous solvent.

<10> A dyeing method using the coloring composition according to <8> or <9>.

<11> A dyed article comprising:
  the compound, the tautomer of the compound, or the salt of the compound or the tautomer according to any one of <1> to <7>.

<12> A method for producing the compound, the tautomer of the compound, or the salt of the compound or the tautomer according to any one of <1> to <7>, the method comprising:
  a step of reacting a diazonium salt represented by Formula 5' with a compound represented by Formula 6 to obtain a compound represented by Formula 7'.

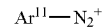
Formula 5'

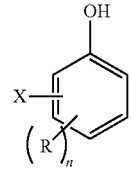
Formula 6

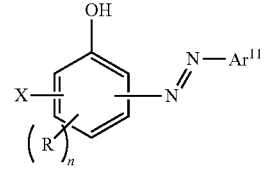
Formula 7'

In Formula 5', Formula 6, and Formula 7', $Ar^{11}$ represents a heterocyclic group, R represents a substituent, X— represents $R^1O$—, $R^{2a}R^{2b}N$—, or $R^3S$—, $R^{2a}$, and $R^{2b}$ each independently represent a hydrogen atom or an alkyl group, $R^3$ represents an alkyl group, n represents 0, 1, 2, or 3, and in a case where n represents 2 or 3, R's may be the same or different from each other.

<13> A method for producing the compound, the tautomer of the compound, or the salt of the compound or the tautomer according to any one of <1> to <7>, the method comprising:
  a step of reacting a diazonium salt represented by Formula 5 with a compound represented by Formula 6 to obtain a compound represented by Formula 7; and
  a step of reacting the obtained compound represented by Formula 7 with a diazonium salt represented by Formula 8.

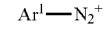
Formula 5

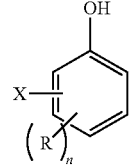
Formula 6

Formula 7

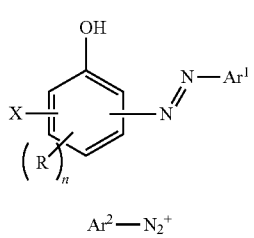

Formula 8

$Ar^2—N_2^+$

In Formulae 5 to 8, $Ar^1$ and $Ar^2$ each independently represent an aromatic hydrocarbon group or a heterocyclic group, R represents a substituent, X— represents $R^1O—$, $R^{2a}R^{2b}N—$, or $R^3S—$, $R^1$, $R^{2a}$, and $R^{2b}$ each independently represent a hydrogen atom or an alkyl group, $R^3$ represents an alkyl group, n represents 0, 1, or 2, and in a case where n represents 2, R's may be the same or different from each other. However, $Ar^1$ and $Ar^2$ are not simultaneously aromatic hydrocarbon groups.

<14> A method for producing the compound, the tautomer of the compound, or the salt of the compound or the tautomer according to any one of <1> to <7>, the method comprising:
a step of reacting a diazonium salt represented by Formula 5 with a compound represented by Formula 10 to obtain a compound represented by Formula 11; and
a step of reacting the obtained compound represented by Formula 11 with a diazonium salt represented by Formula 8 to obtain a compound represented by Formula 12.

Formula 5

$Ar^1—N_2^+$

Formula 10

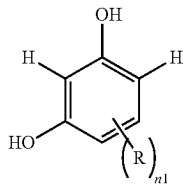

Formula 11

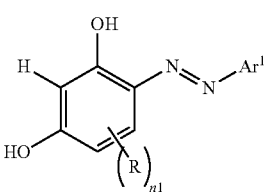

Formula 8

$Ar^2—N_2^+$

Formula 12

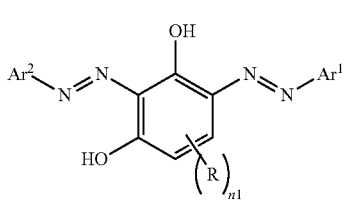

In Formula 5, Formula 8, and Formulae 10 to 12, $Ar^1$ and $Ar^2$ each independently represent an aromatic hydrocarbon group or a heterocyclic group, R represents a substituent, n1 represents 0, 1, or 2, and in a case where n1 represents 2, R's may be the same or different from each other. However, $Ar^1$ and $Ar^2$ are not simultaneously aromatic hydrocarbon groups.

<15> A method for producing the compound, the tautomer of the compound, or the salt of the compound or the tautomer according to any one of <1> to <7>, the method comprising:
a step of reacting a diazonium salt represented by Formula 5 with a compound represented by Formula 13 to obtain a compound represented by Formula 14; and
a step of reacting the obtained compound represented by Formula 14 with a diazonium salt represented by Formula 8 to obtain a compound represented by Formula 15.

Formula 5

$Ar^1—N_2^+$

Formula 13

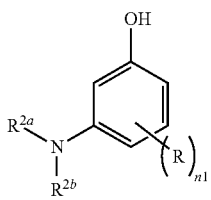

Formula 14

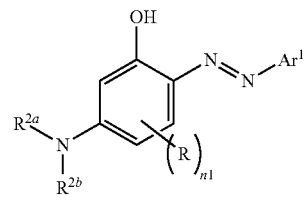

Formula 8

$Ar^2—N_2^+$

Formula 15

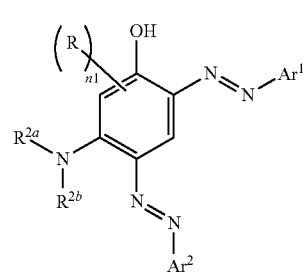

In Formula 5, Formula 8, and Formulae 13 to 15, $Ar^1$ and $Ar^2$ each independently represent an aromatic hydrocarbon group or a heterocyclic group. $R^{2a}$ and $R^{2b}$ each independently represent a hydrogen atom or an alkyl group, $R^{2a}$ and $R^{2b}$ may be the same or different from each other, and $R^{2a}$ and $R^{2b}$ may be bonded to each other to form a nitrogen-containing hetero ring. R represents a substituent, n1 represents 0, 1, 2, or 3, and in a case where n1 represents 2 or 3, R's may be the same or different from each other. However, $Ar^1$ and $Ar^2$ are not simultaneously aromatic hydrocarbon groups.

According to the aspect of the present invention, it is possible to provide a novel compound, a tautomer of the compound, or a salt of the compound or the tautomer.

According to another aspect of the present invention, it is possible to provide a coloring composition with a hue having low chroma saturation.

In addition, according to still another aspect of the present invention, it is possible to provide a method for producing the compound, the tautomer of the compound, or the salt of the compound or the tautomer, and a dyeing method and a dyed article dyed with the compound, the tautomer of the compound, or the salt of the compound or the tautomer.

DESCRIPTION OF THE PREFERRED EMBODIMENTS

Hereinafter, the content of the present disclosure will be described in detail. The description of configuration requirements below is made based on representative embodiments of the present disclosure in some cases, but the present disclosure is not limited to such embodiments.

In the present specification, the numerical ranges shown using "to" indicate ranges including the numerical values described before and after "to" as a lower limit value and an upper limit value.

In numerical ranges described in stages in the present specification, an upper limit value or a lower limit value described in one numerical range may be replaced with an upper limit value or a lower limit value of a numerical range described in another stage. In addition, in the numerical ranges described in the present specification, the upper limit value or the lower limit value of the numerical ranges may be replaced with the values shown in examples.

In addition, in a case where substitution or unsubstitution is not noted in regard to the notation of a "group" (atomic group) in the present specification, the "group" includes not only a group not having a substituent but also a group having a substituent. For example, an "alkyl group" not only includes an alkyl group not including a substituent (unsubstituted alkyl group), but also an alkyl group including a substituent (substituted alkyl group).

Further, a term "step" in the present specification indicates not only an independent step but also a step which cannot be clearly distinguished from other steps as long as the intended purpose of the step is achieved. In addition, in the present disclosure, "% by mass" is identical to "% by weight" and "part by mass" is identical to "part by weight".

Furthermore, in the present disclosure, a combination of two or more preferred aspects is a more preferred aspect.

Hereinafter, the present disclosure will be described in detail.

(Compound represented by Formula 1, tautomer of compound, or salt of compound or tautomer)

A compound, a tautomer of the compound, or a salt of the compound or the tautomer according to an embodiment of the present disclosure is a compound represented by Formula 1, a tautomer of the compound, or a salt of the compound or the tautomer.

A certain aspect of the compound represented by Formula 1, the tautomer of the compound, or the salt of the compound or the tautomer according to the embodiment of the present disclosure can be suitably used as an azo coloring agent.

In addition, a certain aspect of the compound represented by Formula 1, the tautomer of the compound, or the salt of the compound or the tautomer according to the embodiment of the present disclosure can be suitably used as a bisazo coloring agent.

The present disclosure includes not only the compound represented by Formula 1 but also the tautomer of the compound.

In addition, the compound represented by Formula 1 or the tautomer of the compound may be in a form of a salt, or may be a mixed salt of two or more kinds thereof.

The tautomer is generally known that, for example, a compound exists as two or more isomers which can be easily interconverted from one to the other, and examples thereof include an isomer produced by moving a proton bonded to one atom in a molecule to another atom.

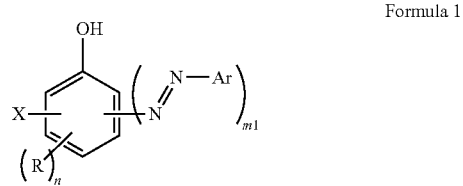

Formula 1

In Formula 1, X— represents $R^1O$—, $R^{2a}R^{2b}N$—, or $R^3S$—, $R^1$, $R^{2a}$, and $R^{2b}$ each independently represent a hydrogen atom or an alkyl group, and $R^3$ represents an alkyl group. In a case where X— is $R^{2a}R^{2b}N$—, $R^{2a}$ and $R^{2b}$ may be the same or different from each other, and $R^{2a}$ and $R^{2b}$ may be bonded to each other to form a nitrogen-containing hetero ring. R's each independently represent a substituent, n represents 0, 1, 2, or 3, and in a case where n represents 2 or 3, R's may be the same or different from each other. Ar represents an aromatic hydrocarbon group or a heterocyclic group, m1 represents 1, 2, or 3, and in a case where m1 represents 2 or 3, Ar's may be the same or different from each other. However, at least one of Ar's is a heterocyclic group.

As a result of intensive studies by the present inventors, it has been found that a novel compound, a tautomer thereof, and a salt thereof can be provided by adopting the configuration of the compound represented by Formula 1.

In addition, as a result of intensive studies by the present inventors, it has been found that a compound, a coloring composition, and a colored product with a hue having low chroma saturation can be provided by adopting the above-described configuration.

The mechanism of the excellent effects obtained by employing the above-described configuration is not clear, but is presumed as follows.

Since the compound represented by Formula 1, the tautomer thereof, or the salt thereof described above has a phenol structure, an X— structure (that is, a $R^1O$— structure, a $R^{2a}R^{2b}N$— structure, or a $R^3S$— structure), an azo group, and a heterocyclic group linked to at least one azo group, a compound having low chroma saturation is obtained. In addition, dissociation of the phenol structure (formation of a phenoxide structure) results in obtaining a compound having lower chroma saturation.

In addition, since the compound represented by Formula 1, the tautomer thereof, or the salt thereof described above has the above-described configuration, it is presumed that a hue having low lightness is obtained, fastness of the hue is excellent, an absorption waveform is wide, and absorption is observed over the entire visible region (wavelength of 400 nm to 700 nm).

Hereinafter, details of the compound represented by Formula 1, the tautomer thereof, or the salt thereof will be described.

In Formula 1, Ar represents an aromatic hydrocarbon group or a heterocyclic group. In a case where m1 in Formula 1 represents 2 or 3, Ar's may be the same or different from each other. However, at least one of Ar's is a heterocyclic group. From the viewpoint of low chroma saturation, low brightness, and broad absorption in the visible region, it is preferable that Ar's are each independently a heterocyclic group.

The aromatic hydrocarbon group in Ar may be unsubstituted or may have a substituent. As the aromatic hydrocarbon group which may have a substituent, a phenyl group, a 1-naphthyl group, or a 2-naphthyl group is preferable.

From the viewpoint of low chroma saturation, low brightness, and broad absorption in the visible region, the heterocyclic group in Ar is preferably a heterocyclic group containing one or more heteroatoms selected from the group consisting of an oxygen atom, a sulfur atom, and a nitrogen atom in the ring.

From the viewpoint of low chroma saturation, low brightness, and broad absorption in the visible region, the heterocyclic group in Ar is preferably a heterocyclic group including a 5-membered hetero ring or a 6-membered hetero ring, more preferably a heterocyclic group including a 5-membered hetero ring, and particularly preferably a 5-membered heteroaromatic ring group.

In addition, from the viewpoint of low chroma saturation, low brightness, and broad absorption in the visible region, the heterocyclic group in Ar is preferably a heteroaromatic ring group, and more preferably a 5- or 6-membered heterocyclic group containing one or more heteroatoms selected from the group consisting of an oxygen atom, a sulfur atom, and a nitrogen atom in the ring.

Furthermore, from the viewpoint of low chroma saturation, low brightness, and broad absorption in the visible region, the heterocyclic group in Ar is preferably a heterocyclic group containing a sulfur atom, more preferably a heterocyclic group containing a sulfur atom and a nitrogen atom, and particularly preferably a heteroaromatic ring group containing a sulfur atom and a nitrogen atom.

The heterocyclic group in Ar may be a ring fused with another ring. Among such fused ring groups, a group fused with a 5-membered ring or a 6-membered ring is preferable.

The number of carbon atoms in the heterocyclic group in Ar is preferably 2 to 20 and more preferably 2 to 10.

In addition, from the viewpoint of low chroma saturation, low brightness, and broad absorption in the visible region, the number of heteroatoms in the heterocyclic group in Ar is preferably 2 or more, more preferably 2 to 4, and particularly preferably 2 or 3.

Furthermore, in a case where Ar's is two pieces or more, each Ar may be the same group (in a case where at least two are heterocyclic groups) or different groups, but from the viewpoint of low chroma saturation, low brightness, and broad absorption in the visible region, it is preferable to be the same group.

The heterocyclic group in Ar of Formula 1 is preferably derived from a diazo component. Here, the diazo component is a partial structure which can be introduced by converting a heterocyclic compound having an amino group as a substituent into a diazo compound, and subjecting it to a diazo coupling reaction with a coupler (for example, a phenol structure portion in Formula 1).

In other words, the heterocyclic group in Ar is a substituent in an amino-substituted heterocyclic compound capable of diazotization, in which the amino group is removed to form a monovalent group.

The aromatic hydrocarbon group and heterocyclic group in Ar of Formula 1 can contain one or more substituents, and two or more substituents may be the same or different from each other.

Examples of the substituent include a halogen atom, a hydroxy group, an alkyl group, a cycloalkyl group, an alkenyl group, a cycloalkenyl group, an alkynyl group, an aryl group, a heterocyclic group, an alkoxy group, an aryloxy group, a heterocyclicoxy group, a sulfo group, an acyl group, an alkoxycarbonyl group, an aryloxycarbonyl group, a carboxy group, a carbamoyl group, an acyloxy group, a carbamoyloxy group, an alkoxycarbonyloxy group, aryloxycarbonyloxy, a cyano group, a nitro group, an amino group (including an anilino group), an acylamino group, an alkoxycarbonylamino group, a carbamoylamino group, an aryloxycarbonylamino group, a sulfamoylamino group, an alkylsulfonylamino group, an arylsulfonylamino group, a mercapto group, an alkylthio group, an arylthio group, a heterocyclicthio group, a sulfamoyl group, an alkylsulfinyl group, an arylsulfinyl group, an alkylsulfonyl group, an arylsulfonyl group, an arylazo group, a heterocyclic azo group, an imide group, a phosphino group, a phosphinyl group, a phosphinyloxy group, and a phosphinylamino group. More specific examples of the substituent include a halogen atom (for example, a fluorine atom, a chlorine atom, a bromine atom, and an iodine atom), an alkyl group (a linear, branched, or cyclic alkyl group having 1 to 10, preferably 1 to 6 carbon atoms; for example, methyl, ethyl, n-propyl, isopropyl, t-butyl, n-octyl-2-chloroethyl-2-cyanoethyl-2-ethylhexyl, cyclopropyl, and cyclopentyl), an alkenyl group (a linear, branched, or cyclic alkenyl group having 2 to 10, preferably 2 to 6 carbon atoms; for example, vinyl, allyl, prenyl, and cyclopenten-1-yl), an alkynyl group (an alkynyl group having 2 to 10, preferably 2 to 6 carbon atoms; for example, ethynyl and propargyl), an aryl group (an aryl group having 6 to 12, preferably 6 to 8 carbon atoms; for example, phenyl, p-tolyl, naphthyl, 3-chlorophenyl, and 2-aminophenyl), heterocyclic group (a monovalent group having 1 to 12, preferably 2 to 6 carbon atoms, which is obtained by removing one hydrogen atom from a 5-membered or 6-membered aromatic or non-aromatic heterocyclic compound; for example, 1-pyrazolyl, 1-imidazolyl, 2-furyl, 2-thienyl, 4-pyrimidinyl, and 2-benzothiazolyl), a cyano group, a hydroxy group, a nitro group, an alkoxy group (a linear, branched, or cyclic alkoxy group having 1 to 10, preferably 1 to 6 carbon atoms; for example, methoxy, ethoxy, isopropoxy, t-butoxy, cyclopentyloxy, 2-buten-1-yloxy, and 2-methoxyethoxy), an aryloxy group (an aryloxy group having 6 to 12, preferably 6 to 8 carbon atoms; for example, phenoxy, 2-methylphenoxy, 4-t-butylphenoxy, and 3-nitrophenoxy), a heterocyclicoxy group (a heterocyclicoxy group having 1 to 12, preferably 2 to 6 carbon atoms; for example, 1-phenyltetrazol-5-oxy-2-tetrahydropyranyloxy), an acyloxy group (an acyloxy group having 1 to 12, preferably 1 to 8 carbon atoms; for example, a formyloxy group, acetyloxy, pivaloyloxy, benzoyloxy, and p-methoxyphenylcarbonyloxy), a carbamoyloxy group (a carbamoyloxy group having 1 to 10, preferably 1 to 6 carbon atoms; for example, N,N-dimethylcarbamoyloxy, N,N-diethylcarbamoyloxy, morpholinocarbonyloxy, and N,N-octylcarbamoyloxy), an alkoxycarbonyloxy group (an alkoxycarbonyloxy group having 2 to 10, preferably 2 to 6 carbon atoms; for example, methoxycarbonyloxy, ethoxycarbonyloxy, t-butoxycarbonyloxy, and n-octyloxycarbonyloxy), an aryloxycarbonyloxy group (an aryloxycarbonyloxy group having 7 to 12, preferably 7 to 10 carbon atoms; for example, phenoxycarbonyloxy and p-methoxyphenoxycarbonyloxy), an amino group (an amino group, an alkylamino group having 1 to 10, preferably 1 to 6 carbon atoms, an anilino group having 6 to 12, preferably 6 to 8 carbon atoms, or a heterocyclic amino group having 1 to 12, preferably 2 to 6 carbon atoms; for example, including amino, methylamino, dimethylamino, anilino, N-methyl-anilino, diphenylamino, imidazol-2-ylamino, and pyrazol-3-ylamino), an acylamino group (an alkylcarbonylamino group having 1 to 10, preferably 1 to 6 carbon atoms, an arylcarbonylamino group having 6 to 12, preferably 6 to 8 carbon atoms, or a heterocyclic carbonylamino group having 2 to 12, preferably 2 to 6 carbon atoms; for example, including formylamino, acetylamino, pivaloylamino, benzoylamino, pyridine-4-carbonylamino, and thiophene-2-carbonylamino), an aminocarbonylamino group (aminocarbonylamino having 1 to 12, preferably 1 to 6 carbon atoms; for example, carbamoylamino, N,N-dimethylaminocarbonylamino, N,N-diethylaminocarbonylamino, and morpholin-4-ylcarbonylamino), an alkoxycarbonylamino group (an alkoxycarbonylamino group having 2 to 10, preferably 2 to 6 carbon atoms; for example, methoxycarbonylamino, ethoxycarbonylamino, and t-butoxycarbonylamino), an aryloxycarbonylamino group (an aryloxycarbonylamino group having 7 to 12, preferably 7 to 9 carbon atoms; for example, phenoxycarbonylamino, p-chlorophenoxycarbonylamino, and 4-methoxyphenoxycarbonylamino), a sulfamoylamino group (a sulfamoylamino group having 0 to 10, preferably 0 to 6 carbon atoms; for example, sulfamoylamino, N,N-dimethylaminosulfonylamino, and N-(2-hydroxyethyl)sulfamoylamino), an alkylsulfonylamino group (an alkylsulfonylamino group having 1 to 10, preferably 1 to 6 carbon atoms; for example, methylsulfonylamino and butylsulfonylamino), an arylsulfonylamino group (an arylsulfonylamino group having 6 to 12, preferably 6 to 8 carbon atoms; for example, phenylsulfonylamino, 2,3,5-trichlorophenylsulfonylamino, and p-methylphenylsulfonylamino), a mercapto group, an alkylthio group (an alkylthio group having 1 to 10, preferably 1 to 6 carbon atoms; for example, methylthio, ethylthio, and butylthio), an arylthio group (arylthio having 6 to 12, preferably 6 to 8 carbon atoms; for example, phenylthio, p-chlorophenylthio, and m-methoxythio), a heterocyclicthio group (a heterocyclicthio group having 2 to 10, preferably 1 to 6 carbon atoms; for example, 2-benzothiazolylthio, 1-phenyltetrazol-5-ylthio), a sulfamoyl group (a sulfamoyl group having 0 to 10, preferably 0 to 6 carbon atoms; for example, sulfamoyl, N-ethylsulfamoyl, N,N-dimethylsulfamoyl, N-acetylsulfamoyl, and N-benzoylsulfamoyl), an alkylsulfinyl group (an alkylsulfinyl group having 1 to 10, preferably 1 to 6 carbon atoms; for example, methylsulfinyl and ethylsulfinyl), an arylsulfinyl group (an arylsulfinyl group having 6 to 12, preferably 6 to 8 carbon atoms; for example, phenylsulfinyl and p-methylphenylsulfinyl), an alkylsulfonyl group (an alkylsulfonyl group having 1 to 10, preferably 1 to 6 carbon atoms; for example, methylsulfonyl and ethylsulfonyl), an arylsulfonyl group (an arylsulfonyl group having 6 to 12, preferably 6 to 8 carbon atoms; for example, phenylsulfonyl and p-chlorophenylsulfonyl), a sulfo group, an acyl group, (a formyl group, an alkylcarbonyl group having 2 to 10, preferably 2 to 6 carbon atoms, or an arylcarbonyl group having 7 to 12, preferably 7 to 9 carbon atoms; for example, acetyl, pivaloyl, 2-chloroacetyl, benzoyl, and 2,4-dichlorobenzoyl), an alkoxycarbonyl group (an alkoxycarbonyl group having 2 to 10, preferably 2 to 6 carbon atoms; for example, methoxycarbonyl, ethoxycarbonyl, t-butoxycarbonyl, and isobutyloxycarbonyl), an aryloxycarbonyl group (an aryloxycarbonyl group having 7 to 12, preferably 7 to 9 carbon atoms; for example, phenoxycarbonyl-2-chlorophenoxycarbonyl, 3-nitrophenoxycarbonyl, and 4-t-butyl phenoxycarbonyl), a carbamoyl group (a carbamoyl group having 1 to 10, preferably 1 to 6 carbon atoms; for example, carbamoyl, N-methylcarbamoyl, N,N-dimethylcarbamoyl, N-(2-hydroxyethyl)carbamoyl, and N-(methylsulfonyl)carbamoyl), an arylazo group (an arylazo group having 6 to 12, preferably 6 to 8 carbon atoms; for example, phenylazo and p-chlorophenylazo), a heterocyclic azo group (a heterocyclic azo group having 1 to 10, preferably 1 to 6 carbon atoms; for example, pyrazol-3-ylazo, thiazol-2-ylazo, and 5-methylthio-1,3,4-thiadiazole-2-ylazo), an imide group (an imide group having 2 to 10, preferably 4 to 8 carbon atoms; for example, succinimide and phthalimide), a phosphino group (a phosphino group having 2 to 12, preferably 2 to 6 carbon atoms; for example, dimethylphosphino, diphenylphosphino, and methylphenoxyphosphino), a phosphinyl group (a phosphinyl group having 2 to 12 carbon atoms, preferably 2 to 6 carbon atoms; for example, phosphinyl and diethoxyphosphinyl), a phosphinyloxy group (a phosphinyloxy group having 2 to 12, preferably 2 to 6 carbon atoms; for example, diphenoxyphosphinyloxy and dibutoxyphosphinyloxy), and a phosphinylamino group (a phosphinylamino group having 2 to 12, preferably 2 to 6 carbon atoms; for example, dimethoxyphosphinylamino and dimethylaminophosphinylamino).

In a case where these groups are groups which can be further substituted, these groups can further contain a substituent, and preferred examples thereof include groups having the same definition as those described as preferred substituents of the heterocyclic group in Ar. In a case where these groups are substituted with two or more substituents, these substituents may be the same or different from each other.

As the substituent of the aromatic hydrocarbon group and heterocyclic group in Ar of Formula 1, a halogen atom, an alkyl group, an aryl group, an heterocyclic group, a cyano group, a hydroxy group, a nitro group, an alkoxy group, an aryloxy group, an amino group (including an anilino group), an acylamino group, an aminocarbonylamino group, an alkoxycarbonylamino group, an alkylsulfonylamino group, an arylsulfonylamino group, an alkylthio group, an arylthio group, a heterocyclicthio group, a sulfamoyl group, an alkylsulfonyl group, an arylsulfonyl group, an acyl group, an alkoxycarbonyl group, or a carbamoyl group is preferable, and a halogen atom, an alkyl group, a cyano group, a hydroxy group, a nitro group, an alkoxy group, an amino group (including an anilino group), an acylamino group, an alkylsulfonylamino group, or a carbamoyl group is more preferable.

From the viewpoint of low chroma saturation, low brightness, fastness of hue, and broad absorption in the visible region, it is preferable that at least one of Ar's is a group represented by any of Formulae (A-1) to (A-28).

In addition, from the viewpoint of low chroma saturation, low brightness, fastness of hue, and broad absorption in the visible region, it is preferable that at least one of Ar's is a group represented by any of Formulae (A-1) to (A-28); it is more preferable that at least one of Ar's is a group represented by Formula (A-1), Formula (A-5), Formula (A-8), Formula (A-9), Formula (A-10), Formula (A-11), Formula (A-12), Formula (A-13), Formula (A-14), Formula (A-15), Formula (A-17), Formula (A-19), Formula (A-22), Formula (A-23), Formula (A-24), or Formula (A-25); and it is particularly preferable that at least one of Ar's is a group represented by Formula (A-8), Formula (A-9), Formula (A-10), Formula (A-11), Formula (A-14), Formula (A-15), Formula (A-22), Formula (A-23), or Formula (A-27).

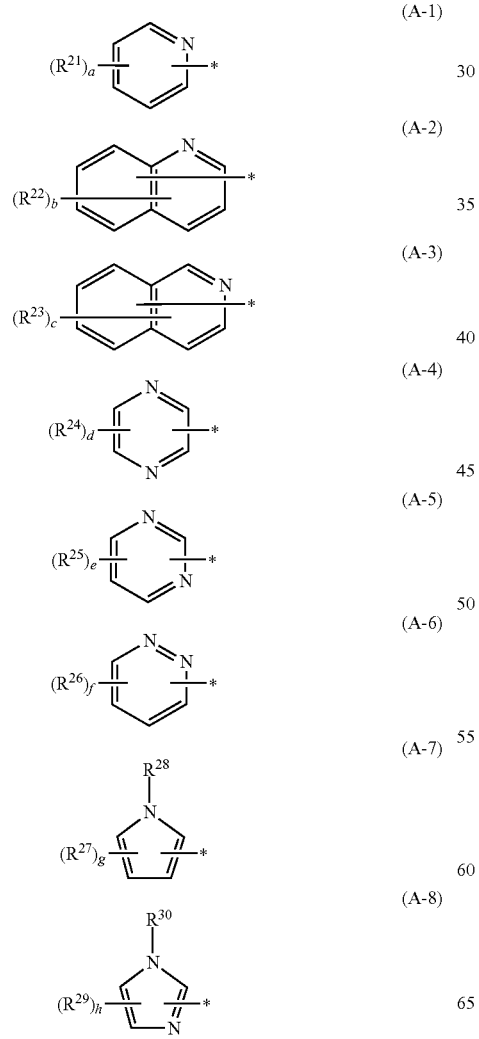
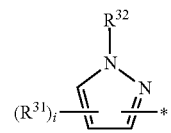
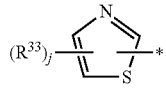
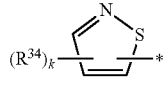
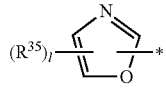
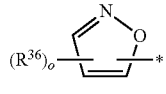
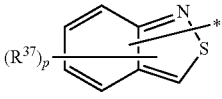
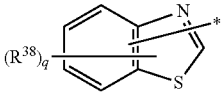
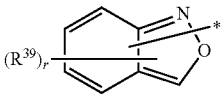
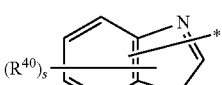
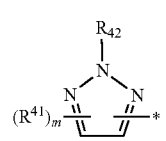
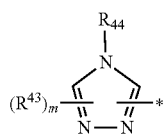
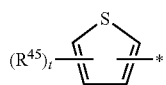
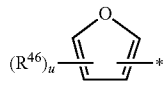
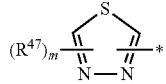

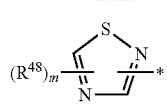 (A-23)

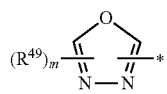 (A-24)

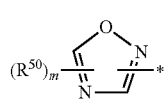 (A-25)

 (A-26)

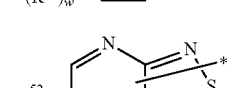 (A-27)

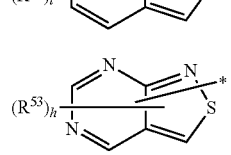 (A-28)

In Formulae (A-1) to (A-28), * represents a position bonded to an azo group in Formula 1, $R^{21}$ to $R^{27}$, $R^{29}$, $R^{31}$, and $R^{33}$ to $R^{53}$ each independently represent a halogen atom, an alkyl group, an aryl group, a heterocyclic group, a cyano group, a hydroxy group, a nitro group, an alkoxy group, an aryloxy group, an amino group, an acylamino group, an aminocarbonylamino group, an alkoxycarbonylamino group, an alkylsulfonylamino group, an arylsulfonylamino group, an alkylthio group, an arylthio group, a heterocyclicthio group, a sulfamoyl group, an alkylsulfonyl group, an arylsulfonyl group, an acyl group, an alkoxycarbonyl group, or a carbamoyl group, $R^{28}$, $R^{30}$, and $R^{32}$ each independently represent a hydrogen atom, a halogen atom, an alkyl group, an aryl group, a heterocyclic group, a cyano group, a hydroxy group, a nitro group, an alkoxy group, an aryloxy group, an amino group, an acylamino group, an aminocarbonylamino group, an alkoxycarbonylamino group, an alkylsulfonylamino group, an arylsulfonylamino group, an alkylthio group, an arylthio group, a heterocyclicthio group, a sulfamoyl group, an alkylsulfonyl group, an arylsulfonyl group, an acyl group, an alkoxycarbonyl group, or a carbamoyl group, adjacent groups among $R^{21}$ to $R^{53}$ may be bonded to each other to form a saturated or unsaturated 5- or 6-membered ring structure, a, p, q, r, and s represent an integer of 0 to 4, b and c represent an integer of 0 to 6, d, e, f, g, t, and u represent an integer of 0 to 3, h, i, j, k, l, and o represent an integer of 0 to 2, w represents an integer of 0 to 5, m represents 0 or 1, and two or more groups represented by $R^{21}$ to $R^{53}$ in a same molecule may be the same or different from each other.

In a case where $R^{21}$ to $R^{53}$ are groups which can be further substituted, $R^{21}$ to $R^{53}$ can further contain a substituent, and in this case, the substituent is the same as those mentioned as the substituent of the heterocyclic group in Ar of Formula 1.

From the viewpoint of low chroma saturation, low brightness, fastness of hue, and broad absorption in the visible region, R in Formula 1 is preferably a halogen atom, a hydroxy group, an alkyl group, an aryl group, an alkoxy group, an aryloxy group, an acyl group, an alkoxycarbonyl group, a carboxy group, a carbamoyl group, a cyano group, an acylamino group, a sulfonylamino group, a sulfamoyl group, an alkylthio group, an arylthio group, an alkylsulfonyl group, an arylsulfonyl group, or a sulfo group; more preferably a halogen atom, a hydroxy group, an alkyl group, an aryl group, an alkoxy group, an aryloxy group, an acyl group, an alkoxycarbonyl group, or a carboxy group; and particularly preferably a hydroxy group, an alkyl group, or an acyl group.

The halogen atom represented as R is, for example, preferably a fluorine atom, a chlorine atom, a bromine atom, or an iodine atom, and particularly preferably a fluorine atom or a chlorine atom.

The alkyl group represented as R is preferably an alkyl group having 1 to 12 carbon atoms, and particularly preferably an alkyl group having 1 to 8 carbon atoms. For example, a methyl group, an ethyl group, an n-butyl group, or a t-butyl group is preferable.

The aryl group represented as R is preferably an aryl group having 6 to 12 carbon atoms. For example, a phenyl group, a 1-naphthyl group, or a 2-naphthyl group is preferable.

The alkoxy group represented as R is preferably an alkoxy group having 1 to 12 carbon atoms, and more preferably an alkoxy group having 1 to 8 carbon atoms. For example, a methoxy group, an ethoxy group, an n-butoxy group, a t-butoxy group, or a 2-methoxyethoxy group is preferable.

The aryloxy group represented as R is preferably an aryloxy group having 6 to 12 carbon atoms. For example, a phenoxy group or a 4-methylphenoxy group is preferable.

The acyl group represented as R is preferably an acyl group having 1 to 12 carbon atoms, and particularly preferably an acyl group having 1 to 7 carbon atoms. For example, a formyl group, an acetyl group, a hydroxyacetyl group, a propionyl group, a 2-methylpropionyl group, or a benzoyl group is preferable.

The alkoxycarbonyl group represented as R is preferably an alkoxycarbonyl group having 2 to 10 carbon atoms, and particularly preferably an alkoxycarbonyl group having 2 to 6 carbon atoms. For example, a methoxycarbonyl group, an ethoxycarbonyl group, a t-butoxycarbonyl group, or an isobutyloxycarbonyl group is preferable.

The carbamoyl group represented as R is preferably a carbamoyl group having 1 to 10 carbon atoms, and particularly preferably a carbamoyl group having 1 to 6 carbon atoms. For example, a carbamoyl group, an N-methylcarbamoyl group, an N,N-dimethylcarbamoyl group, an N-(2-hydroxyethyl)carbamoyl group, or an N-(methylsulfonyl)carbamoyl group is preferable.

With the acylamino group represented as R, as an alkylcarbonylamino group, an alkylcarbonylamino group having 1 to 10 carbon atoms is preferable, and an alkylcarbonylamino group having 1 to 6 carbon atoms is particularly preferable. In addition, as an arylcarbonylamino group, an arylcarbonylamino group having 6 to 12 carbon atoms is preferable, and an arylcarbonylamino group having 6 to 8 carbon atoms is particularly preferable. In addition, as a heterocyclic carbonylamino group, a heterocyclic carbonylamino group having 2 to 12 carbon atoms is preferable, and a heterocyclic carbonylamino group having 2 to 6 carbon atoms is particularly preferable. For example, a formylamino group, an acetylamino group, a pivaloylamino group, a benzoylamino group, a pyridine-4-carbonylamino group, a thiophene-2-carbonylamino group, or the like is preferable.

With the sulfonylamino group represented as R, as an alkylsulfonylamino group, an alkylsulfonylamino group having 1 to 10 carbon atoms is preferable, and an alkylsulfonylamino group having 1 to 6 carbon atoms is particularly preferable. In addition, as an arylsulfonylamino group, an arylsulfonylamino group having 6 to 12 carbon atoms is preferable, and an arylsulfonylamino group having 6 to 8 carbon atoms is particularly preferable. For example, a methylsulfonylamino group, a butylsulfonylamino group, a phenylsulfonylamino group, a 2,3,5-trichlorophenylsulfonylamino group, or a p-methylphenylsulfonylamino group is preferable.

The sulfamoyl group represented as R is preferably a sulfamoyl group having 0 to 10 carbon atoms, and particularly preferably a sulfamoyl group having 0 to 6 carbon atoms. For example, a sulfamoyl group, an N-ethyl sulfamoyl group, an N,N-dimethyl sulfamoyl group, an N-acetyl sulfamoyl group, or an N-benzoyl sulfamoyl group is preferable.

The alkylthio group represented as R is preferably an alkylthio group having 1 to 10 carbon atoms, and particularly preferably an alkylthio group having 1 to 6 carbon atoms. For example, a methylthio group, an ethylthio group, or a butylthio group is preferable.

The arylthio group represented as R is preferably an arylthio group having 6 to 12 carbon atoms, and particularly preferably an arylthio group having 6 to 8 carbon atoms. For example, a phenylthio group, a p-chlorophenylthio group, or an m-methoxyphenylthio group is preferable.

The alkylsulfonyl group represented as R is preferably an alkylsulfonyl group having 1 to 10 carbon atoms, and particularly preferably an alkylsulfonyl group having 1 to 6 carbon atoms. For example, a methylsulfonyl group or an ethylsulfonyl group is preferable.

The arylsulfonyl group represented as R is preferably an arylsulfonyl group having 6 to 12 carbon atoms, and particularly preferably an arylsulfonyl group having 6 to 8 carbon atoms. For example, a phenylsulfonyl group or a p-chlorophenylsulfonyl group is preferable.

In a case where n is 2, two R's may be bonded to each other to form a ring. The ring to be formed is preferably a 5-membered ring or a 6-membered ring. The ring to be formed may be saturated or unsaturated, but is preferably unsaturated. The ring to be formed may be either a hydrocarbon ring or a hetero ring, but is preferably an aromatic hydrocarbon ring or a heteroaromatic ring. As an example of the ring to be formed, a cyclohexene ring, a benzene ring, a naphthalene ring, a pyrrole ring, or a pyrazole ring is preferable. A benzene ring or a pyrrole ring is particularly preferable.

In Formula 1, X— represents $R^1O$—, $R^{2a}R^{2b}N$—, or $R^3S$—, $R^1$, $R^{2a}$, and $R^{2b}$ each independently represent a hydrogen atom or an alkyl group, and $R^3$ represents an alkyl group. In a case where X— is $R^{2a}R^{2b}N$—, $R^{2a}$ and $R^{2b}$ may be the same or different from each other, and $R^{2a}$ and $R^{2b}$ may be bonded to each other to form a nitrogen-containing hetero ring. From the viewpoint of low chroma saturation and low brightness, X— is more preferably $R^1O$— or $R^{2a}R^{2b}N$—.

The alkyl group represented as $R^1$, $R^{2a}$, $R^{2b}$, or $R^3$ in Formula 1 is preferably an alkyl group having 1 to 12 carbon atoms, and particularly preferably an alkyl group having 1 to 4 carbon atoms. For example, a methyl group, an ethyl group, an n-butyl group, or a t-butyl group is preferable.

From the viewpoint of low chroma saturation, low brightness, water solubility, and broad absorption in the visible region, $R^1$, $R^{2a}$, and $R^{2b}$ in Formula 1 are preferably a hydrogen atom or a methyl group.

In a case where X— represents $R^{2a}R^{2b}N$—, $R^{2a}R^{2b}N$— may be any of an amino group ($H_2N$—), a monoalkyl-substituted amino group, or a dialkyl-substituted amino group.

In a case where X— represents $R^{2a}R^{2b}N$— and $R^{2a}$ and $R^{2b}$ are bonded to each other to form a nitrogen-containing hetero ring, the nitrogen-containing hetero ring is preferably a 5-membered or 6-membered nitrogen-containing hetero ring. Examples of the nitrogen-containing hetero ring include a pyrrolidine ring, a piperidine ring, a morpholine ring, and a piperazine ring.

A bonding position of X— (that is, $R^1O$—, $R^{2a}R^{2b}N$—, or $R^3S$—) in Formula 1 is not particularly limited, but from the viewpoint of low chroma saturation, low brightness, fastness of hue, and broad absorption in the visible region, the bonding position of X— is a meta-position with respect to a hydroxy group.

From the viewpoint of low chroma saturation, low brightness, fastness of hue, and broad absorption in the visible region, m1 in Formula 1 is preferably 2 or 3, and more preferably 2.

From the viewpoint of low chroma saturation, low brightness, fastness of hue, and broad absorption in the visible region, n in Formula 1 is preferably 0, 1, or 2, and more preferably 0 or 1.

In a case where the compound represented by Formula 1 forms a salt, it is preferable to form a salt with a monovalent or divalent cation. As the monovalent cation, an alkali metal cation (for example, a lithium cation, a sodium cation, and a potassium cation) or an ammonium cation (for example, an ammonium cation, a trimethylammonium cation, a triethylammonium cation, and a tetramethylammonium cation) is preferable. As the divalent cation, an alkaline earth metal cation (for example, a calcium cation) is preferable.

The compound represented by Formula 1 includes a compound represented by any of Formulae A1 to A3.

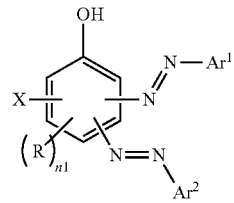

Formula A1

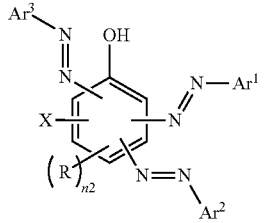

Formula A2

-continued

Formula A3

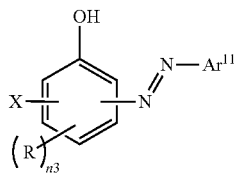

In Formula A1, X— represents $R^1O$—, $R^{2a}R^{2b}N$—, or $R^3S$—, $R^{2a}$, and $R^{2b}$ each independently represent a hydrogen atom or an alkyl group, $R^3$ represents an alkyl group, and in a case where X— is $R^{2a}R^{2b}N$—, $R^{2a}$ and $R^{2b}$ may be the same or different from each other and $R^{2a}$ and $R^{2b}$ are bonded to each other to form a nitrogen-containing hetero ring. $Ar^1$ and $Ar^2$ each independently represent an aromatic hydrocarbon group or a heterocyclic group, and R's each independently represent a substituent. n1 represents 0, 1, or 2, and in a case where n1 represents 2, R's may be the same or different from each other. However, $Ar^1$ and $Ar^2$ are not simultaneously aromatic hydrocarbon groups.

In Formula A2, X— represents $R^1O$—, $R^{2a}R^{2b}N$—, or $R^3S$—, $R^{2a}$, and $R^{2b}$ each independently represent a hydrogen atom or an alkyl group, $R^3$ represents an alkyl group, and in a case where X— is $R^{2a}R^{2b}N$—, $R^{2a}$ and $R^{2b}$ may be the same or different from each other and $R^{2a}$ and $R^{2b}$ are bonded to each other to form a nitrogen-containing hetero ring. n2 represents 0 or 1. $Ar^1$, $Ar^2$, and $Ar^3$ each independently represent an aromatic hydrocarbon group or a heterocyclic group. However, $Ar^1$ and $Ar^2$ are not simultaneously aromatic hydrocarbon groups.

In Formula A3, X— represents $R^1O$—, $R^{2a}R^{2b}N$—, or $R^3S$—, $R^{2a}$, and $R^{2b}$ each independently represent a hydrogen atom or an alkyl group, $R^3$ represents an alkyl group, and in a case where X— is $R^{2a}R^{2b}N$—, $R^{2a}$ and $R^{2b}$ may be the same or different from each other and $R^{2a}$ and $R^{2b}$ are bonded to each other to form a nitrogen-containing hetero ring. n3 represents 0, 1, 2, or 3, and in a case where n3 represents 2 or 3, R's may be the same or different from each other. $Ar^{11}$ represents a heterocyclic group.

$Ar^1$, $Ar^2$, $Ar^3$, and $Ar^{11}$ in Formulae A1 to A3 each independently have the same definition as Ar in Formula 1, and preferred aspects thereof are also the same.

R, $R^{2a}$, and $R^{2b}$ in Formulae A1 to A3 each independently have the same definition as R, $R^{2a}$, and $R^{2b}$ in Formula 1, and preferred aspects thereof are also the same.

From the viewpoint of low chroma saturation, low brightness, fastness of hue, and broad absorption in the visible region, it is preferable that n1's in Formula A1 are each independently 0 or 1.

From the viewpoint of low chroma saturation, low brightness, fastness of hue, and broad absorption in the visible region, it is preferable that n2's in Formula A2 are each independently 0.

From the viewpoint of low chroma saturation, low brightness, fastness of hue, and broad absorption in the visible region, it is preferable that n3's in Formula A3 are each independently 0, 1, or 2, it is more preferable to be 0 or 1, and it is still more preferable to be 0.

From the viewpoint of low chroma saturation, low brightness, fastness of hue, and broad absorption in the visible region, the compound represented by Formula 1 is preferably a compound represented by any of Formulae A1-1 to A1-3, Formulae A2-1 to A2-3, or Formulae A3-1 to A3-3, more preferably a compound represented by any of Formulae A1-1 to A1-3 or Formulae A2-1 to A2-3, and still more preferably a compound represented by any of Formula A1-1, Formula A1-2, or Formula A1-3.

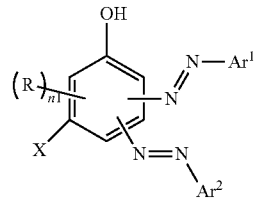

Formula A1-1

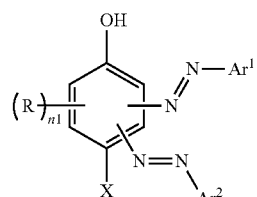

Formula A1-2

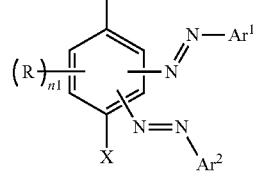

Formula A1-3

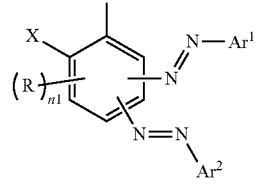

Formula A2-1

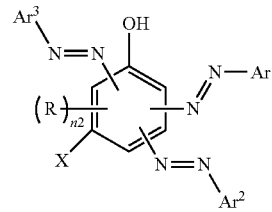

Formula A2-2

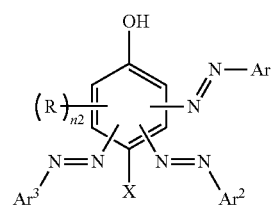

Formula A2-3

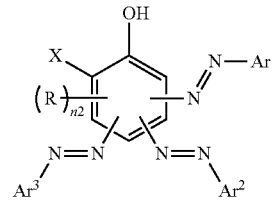

Formula A3-1

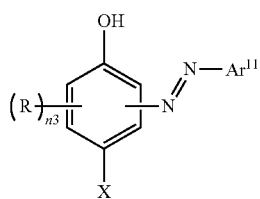

Formula A3-2

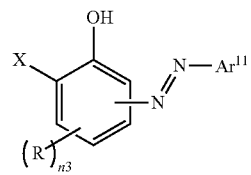

Formula A3-3

In Formulae A1-1 to A1-3, X— represents $R^1O$—, $R^{2a}R^{2b}N$—, or $R^3S$—, $R^1$, $R^{2a}$, and $R^{2b}$ each independently represent a hydrogen atom or an alkyl group, $R^3$ represents an alkyl group, and in a case where X— is $R^{2a}R^{2b}N$—, $R^{2a}$ and $R^{2b}$ may be the same or different from each other and $R^{2a}$ and $R^{2b}$ are bonded to each other to form a nitrogen-containing hetero ring. $Ar^1$ and $Ar^2$ each independently represent an aromatic hydrocarbon group or a heterocyclic group, and R's each independently represent a substituent. n1 represents 0, 1, or 2, and in a case where n1 represents 2, R's may be the same or different from each other. However, $Ar^1$ and $Ar^2$ are not simultaneously aromatic hydrocarbon groups.

In Formulae A2-1 to A2-3, X— represents $R^1O$—, $R^{2a}R^{2b}N$—, or $R^3S$—, $R^1$, $R^{2a}$, and $R^{2b}$ each independently represent a hydrogen atom or an alkyl group, $R^3$ represents an alkyl group, and in a case where X— is $R^{2a}R^{2b}N$—, $R^{2a}$ and $R^{2b}$ may be the same or different from each other and $R^{2a}$ and $R^{2b}$ are bonded to each other to form a nitrogen-containing hetero ring. n1 represents 0 or 1. $Ar^1$, $Ar^2$, and $Ar^3$ each independently represent an aromatic hydrocarbon group or a heterocyclic group. However, $Ar^1$ and $Ar^2$ are not simultaneously aromatic hydrocarbon groups.

In Formulae A3-1 to A3-3, X— represents $R^1O$—, $R^{2a}R^{2b}N$—, or $R^3S$—, $R^1$, $R^{2a}$, and $R^{2b}$ each independently represent a hydrogen atom or an alkyl group, $R^3$ represents an alkyl group, and in a case where X— is $R^{2a}R^{2b}N$—, $R^{2a}$ and $R^{2b}$ may be the same or different from each other and $R^{2a}$ and $R^{2b}$ are bonded to each other to form a nitrogen-containing hetero ring. n3 represents 0, 1, 2, or 3, and in a case where n3 represents 2 or 3, R's may be the same or different from each other. $Ar^{11}$ represents a heterocyclic group.

$Ar^1$, $Ar^2$, R, $R^1$, $R^{2a}$, $R^{2b}$, $R^3$, and n1 in Formulae A1-1 to A1-3 each independently have the same definition as $Ar^1$, $Ar^2$, R, $R^1$, $R^{2a}$, $R^{2b}$, $R^3$, and n1 in Formula A1, and preferred aspects thereof are also the same.

$Ar^1$, $Ar^2$, $Ar^3$, $R^1$, $R^{2a}$, $R^{2b}$, $R^3$, and n2 in Formulae A2-1 to A2-3 each independently have the same definition as $Ar^1$, $Ar^2$, $Ar^3$, $R^1$, $R^{2a}$, $R^{2b}$, in Formula A2, and preferred aspects thereof are also the same.

$Ar^{11}$, $R^1$, $R^{2a}$, $R^{2b}$, $R^3$, and n3 in Formulae A3-1 to A3-3 each independently have the same definition as $Ar^{11}$, $R^1$, $R^{2a}$, $R^{2b}$, and $R^3$ in Formula A3, and preferred aspects thereof are also the same.

In a case where X— in Formula A1 represents $R^1O$—, from the viewpoint of low chroma saturation, low brightness, fastness of hue, and broad absorption in the visible region, as the compound represented by Formula A1, it is preferable that $Ar^1$ and $Ar^2$ are each independently a heterocyclic group, $R^1$ is a hydrogen atom, R is a hydroxy group, an alkyl group, or an acyl group, and n1 is 0 or 1; it is more preferable that $Ar^1$ is a heterocyclic group having a sulfur atom, $Ar^2$ is a heterocyclic group different from $Ar^1$, $R^1$ is a hydrogen atom, R is a hydroxy group, an alkyl group, or an acyl group, and n1 is 0 or 1; and it is particularly preferable that $Ar^1$ is a heterocyclic group having a sulfur atom and a nitrogen atom, $Ar^2$ is a heterocyclic group different from $Ar^1$, $R^1$ is a hydrogen atom, R is a hydroxy group, an alkyl group, or an acyl group, and n1 is 0 or 1.

In a case where X— in Formula A1 represents $R^{2a}R^{2b}N$—, from the viewpoint of low chroma saturation, low brightness, fastness of hue, and broad absorption in the visible region, as the compound represented by Formula A1, it is preferable that $Ar^1$ and $Ar^2$ are each independently a heterocyclic group, $R^{2a}$ and $R^{2b}$ are each independently a hydrogen atom or an alkyl group having 1 to 12 carbon atoms, in a case where $R^{2a}$ and $R^{2b}$ are bonded to form a nitrogen-containing hetero ring, the nitrogen-containing hetero ring is a pyrrolidino group, a piperidino group, or a morpholino group, R is a halogen atom (for example, a chlorine atom) or a methyl group, and n1 is 0 or 1; it is more preferable that $Ar^1$ is a 5-membered heterocyclic group or a 5-membered and 6-membered fused heterocyclic group, $Ar^2$ is a 5-membered heterocyclic group, a 5-membered and 6-membered fused heterocyclic group, or an aromatic hydrocarbon group, $R^{2a}$ is a hydrogen atom or an alkyl group having 1 to 4 carbon atoms (for example, a methyl group, an ethyl group, an n-butyl group, or a t-butyl group), $R^{2b}$ is a hydrogen atom or an alkyl group having 1 to 4 carbon atoms (for example, a methyl group, an ethyl group, an n-butyl group, or a t-butyl group), R is a hydrogen atom or a methyl group, and n1 is 0 or 1; and it is particularly preferable that $Ar^1$ is a 5-membered heterocyclic group or a 5-membered and 6-membered fused heterocyclic group, $Ar^2$ is a 5-membered heterocyclic group or a 5-membered and 6-membered fused heterocyclic group, $R^{2a}$ is a hydrogen atom or a methyl group, $R^{2b}$ is a hydrogen atom or a methyl group, R is a chlorine atom or a methyl group, and n1 is 0 or 1.

In a case where X— in Formula A1 represents $R^3S$—, from the viewpoint of low chroma saturation, low brightness, fastness of hue, and broad absorption in the visible region, as the compound represented by Formula A1, it is preferable that $Ar^1$ and $Ar^2$ are each independently a heterocyclic group, $R^3$ is an alkyl group having 1 to 4 carbon atoms, R is a halogen atom (for example, a chlorine atom) or a methyl group, and n1 is 0 or 1; it is more preferable that $Ar^1$ is a 5-membered hetero ring or a 5-membered and 6-membered fused hetero ring, $Ar^2$ is a 5-membered heterocyclic group, a 5-membered and 6-membered fused heterocyclic group, or an aromatic hydrocarbon group, $R^3$ is an alkyl group having 1 to 4 carbon atoms, R is a chlorine atom or a methyl group, and n1 is 0 or 1; and it is particularly preferable that $Ar^1$ is a 5-membered hetero ring or a 5-membered and 6-membered fused hetero ring, $Ar^2$ is a 5-membered hetero ring or a 5-membered and 6-membered fused hetero ring, $R^3$ is a methyl group, R is a chlorine atom or a methyl group, and n1 is 0 or 1.

In a case where X— in Formula A2 represents $R^1O$—, from the viewpoint of low chroma saturation, low brightness, fastness of hue, and broad absorption in the visible region, as the compound represented by Formula A2, it is preferable that $Ar^1$, $Ar^2$, and $Ar^3$ are each independently a heterocyclic group, $R^1$ is a hydrogen atom, a methyl group, an ethyl group, or a hydroxyethyl group, R is a halogen atom (for example, a chlorine atom) or a methyl group, and n2 is 0 or 1; it is more preferable that $Ar^1$ is a 5-membered hetero ring or a 5-membered and 6-membered fused hetero ring, $Ar^2$ is a 5-membered hetero ring or a 5-membered and 6-membered fused hetero ring, $Ar^3$ is a 5-membered heterocyclic group, a 5-membered and 6-membered fused heterocyclic group, or an aromatic hydrocarbon group, $R^1$ is a hydrogen atom or a methyl group, R is a chlorine atom or a methyl group, and n2 is 0 or 1; and it is particularly preferable that $Ar^1$ is a 5-membered hetero ring, $Ar^2$ is a 5-membered hetero ring or a 5-membered and 6-membered fused hetero ring, $Ar^3$ is a 5-membered hetero ring or a 5-membered and 6-membered fused hetero ring, $R^1$ is a hydrogen atom or a methyl group, and n2 is 0.

In a case where X— in Formula A2 represents $R^{2a}R^{2b}N$—, from the viewpoint of low chroma saturation, low brightness, fastness of hue, and broad absorption in the visible region, as the compound represented by Formula A2, it is preferable that $Ar^1$, $Ar^2$, and $Ar^3$ are each independently a heterocyclic group, $R^{2a}$ and $R^{2b}$ are each independently a hydrogen atom or an alkyl group having 1 to 12 carbon atoms, in a case where $R^{2a}$ and $R^{2b}$ are bonded to form a nitrogen-containing hetero ring, the nitrogen-containing hetero ring is a pyrrolidino group, a piperidino group, or a morpholino group, R is a halogen atom (for example, a chlorine atom) or a methyl group, and n2 is 0 or 1; it is more preferable that $Ar^1$ is a 5-membered hetero ring or a 5-membered and 6-membered fused hetero ring, $Ar^2$ is a 5-membered hetero ring or a 5-membered and 6-membered fused hetero ring, $Ar^3$ is a 5-membered heterocyclic group, a 5-membered and 6-membered fused heterocyclic group, or an aromatic hydrocarbon group, $R^{2a}$ is a hydrogen atom or an alkyl group having 1 to 4 carbon atoms (for example, a methyl group, an ethyl group, an n-butyl group, or a t-butyl group), $R^{2b}$ is a hydrogen atom or an alkyl group having 1 to 4 carbon atoms (for example, a methyl group, an ethyl group, an n-butyl group, or a t-butyl group), R is a chlorine atom or a methyl group, and n2 is 0 or 1; and it is particularly preferable that $Ar^1$ is a 5-membered heterocyclic group, $Ar^2$ is a 5-membered heterocyclic group or a 5-membered and 6-membered fused heterocyclic group, $Ar^3$ is a 5-membered heterocyclic group or a 5-membered and 6-membered fused heterocyclic group, $R^{2a}$ is a hydrogen atom or a methyl group, $R^{2b}$ is a hydrogen atom or a methyl group, and n2 is 0.

In a case where X— in Formula A2 represents $R^3S$—, from the viewpoint of low chroma saturation, low brightness, fastness of hue, and broad absorption in the visible region, as the compound represented by Formula A2, it is preferable that $Ar^1$, $Ar^2$, and $Ar^3$ are each independently a heterocyclic group, $R^3$ is an alkyl group having 1 to 4 carbon atoms, R is a chlorine atom or a methyl group, and n2 is 0 or 1; it is more preferable that $Ar^1$ is a 5-membered heterocyclic group or a 5-membered and 6-membered fused heterocyclic group, $Ar^2$ is a 5-membered heterocyclic group or a 5-membered and 6-membered fused heterocyclic group, $Ar^3$ is a 5-membered heterocyclic group, a 5-membered and 6-membered fused heterocyclic group, or an aromatic hydrocarbon group, $R^3$ is an alkyl group having 1 to 4 carbon atoms, R is a chlorine atom or a methyl group, and n2 is 0 or 1; and it is particularly preferable that $Ar^1$ is a 5-membered heterocyclic group, $Ar^2$ is a 5-membered heterocyclic group or a 5-membered and 6-membered fused heterocyclic group, $Ar^3$ is a 5-membered heterocyclic group or a 5-membered and 6-membered fused heterocyclic group, $R^3$ is a methyl group, and n2 is 0.

In a case where X— in Formula A3 represents $R^1O$—, from the viewpoint of low chroma saturation, low brightness, fastness of hue, and broad absorption in the visible region, as the compound represented by Formula A3, it is preferable that $Ar^{11}$ is a heterocyclic group, $R^1$ is a hydrogen atom, a methyl group, an ethyl group, or a hydroxyethyl group, R is a halogen atom (for example, a chlorine atom) or a methyl group, and n3 is 0 or 1; it is more preferable that $Ar^{11}$ is a 5-membered heterocyclic group or a 5-membered and 6-membered fused heterocyclic group, $R^1$ is a hydrogen atom or a methyl group, R is a chlorine atom or a methyl group, and n3 is 0 or 1; and it is particularly preferable that $Ar^{11}$ is a 5-membered heterocyclic group or a 5-membered and 6-membered fused heterocyclic group, $R^1$ is a hydrogen atom or a methyl group, and n3 is 0.

In a case where X— in Formula A3 represents $R^{2a}R^{2b}N$—, from the viewpoint of low chroma saturation, low brightness, fastness of hue, and broad absorption in the visible region, as the compound represented by Formula A3, it is preferable that $Ar^{11}$ is a heterocyclic group, $R^{2a}$ and $R^{2b}$ are each independently a hydrogen atom or an alkyl group having 1 to 12 carbon atoms, in a case where $R^{2a}$ and $R^{2b}$ are bonded to form a nitrogen-containing hetero ring, the nitrogen-containing hetero ring is a pyrrolidino group, a piperidino group, or a morpholino group, R is a chlorine atom or a methyl group, and n3 is 0 or 1; it is more preferable that $Ar^{11}$ is a 5-membered heterocyclic group or a 5-membered and 6-membered fused heterocyclic group, $R^{2a}$ is a hydrogen atom or an alkyl group having 1 to 4 carbon atoms (for example, a methyl group, an ethyl group, an n-butyl group, or a t-butyl group), $R^{2b}$ is a hydrogen atom or an alkyl group having 1 to 4 carbon atoms (for example, a methyl group, an ethyl group, an n-butyl group, or a t-butyl group), R is a chlorine atom or a methyl group, and n3 is 0 or 1; and it is particularly preferable that $Ar^{11}$ is a 5-membered heterocyclic group or a 5-membered and 6-membered fused heterocyclic group, $R^{2a}$ is a hydrogen atom or a methyl group, $R^{2b}$ is a hydrogen atom or a methyl group, R is a chlorine atom or a methyl group, and n3 is 0 or 1.

In a case where X— in Formula A3 represents $R^3S$—, from the viewpoint of low chroma saturation, low brightness, fastness of hue, and broad absorption in the visible region, as the compound represented by Formula A3, it is preferable that $Ar^{11}$ is a heterocyclic group, $R^3$ is an alkyl group having 1 to 4 carbon atoms, R is a chlorine atom or a methyl group, and n3 is 0 or 1; it is more preferable that $Ar^{11}$ is a 5-membered heterocyclic group or a 5-membered and 6-membered fused heterocyclic group, $R^3$ is an alkyl group having 1 to 4 carbon atoms, R is a chlorine atom or a methyl group, and n3 is 0 or 1; and it is particularly preferable that $Ar^{11}$ is a 5-membered heterocyclic group or a 5-membered and 6-membered fused heterocyclic group, $R^3$ is a methyl group, and n3 is 0.

Specific examples of the compound represented by Formula 1 are described below, but the present disclosure is not limited to these examples. Me represents a methyl group, and Et represents an ethyl group (the same applies hereinafter).

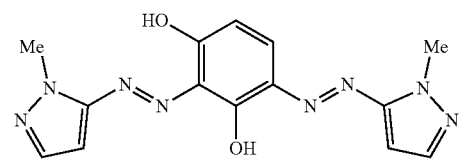

D-1

-continued

D-2, D-3, D-4, D-5, D-6, D-7, D-8, D-9, D-10, D-11, D-12, D-13, D-14, D-15

-continued
D-16
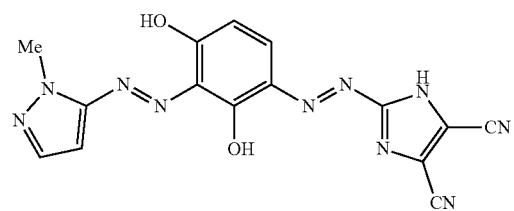
D-17
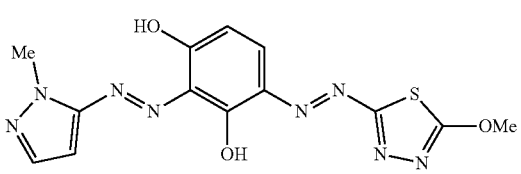
D-18
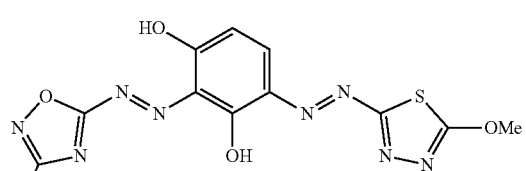
D-19
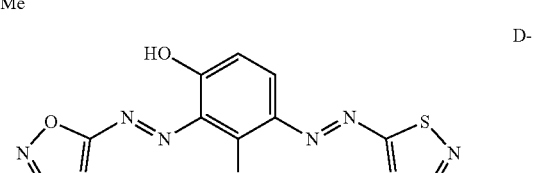
D-20
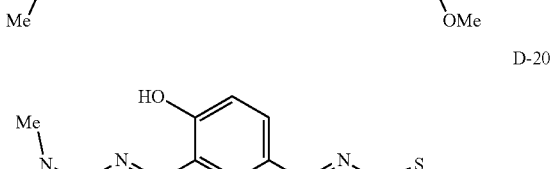
D-21
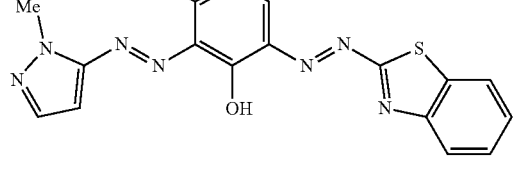
D-22
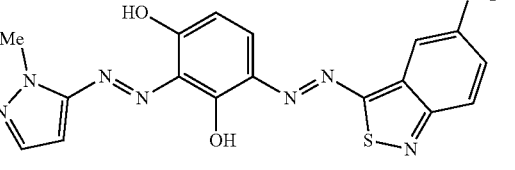
-continued
D-23
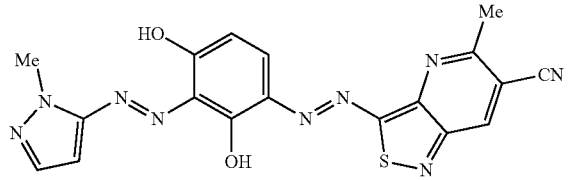
D-24
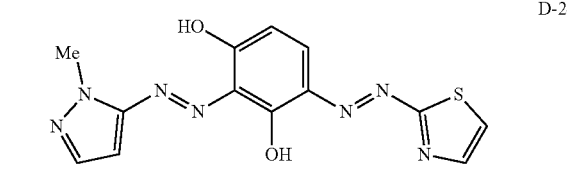
D-25
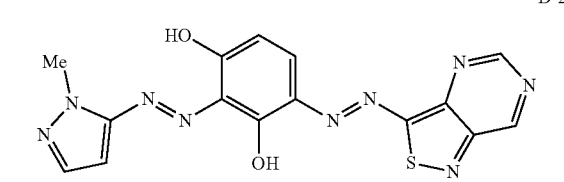
D-26
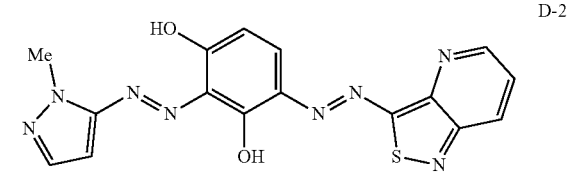
D-27
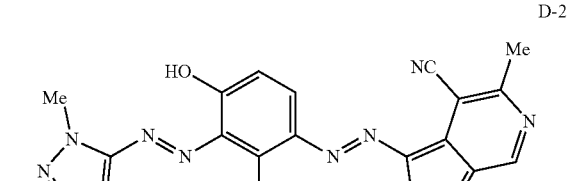
D-28
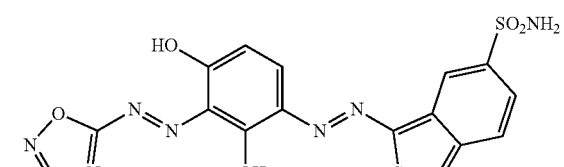
D-29
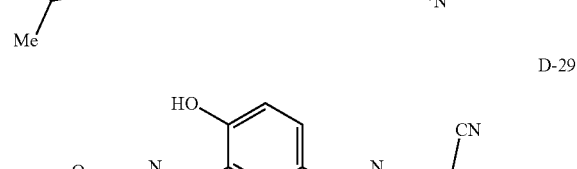
D-30
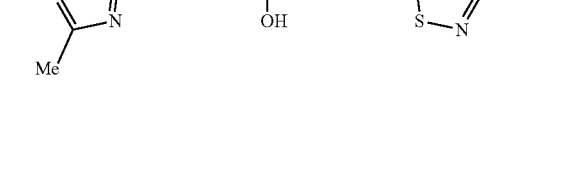

D-31
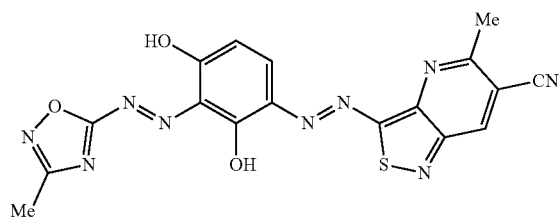
D-32
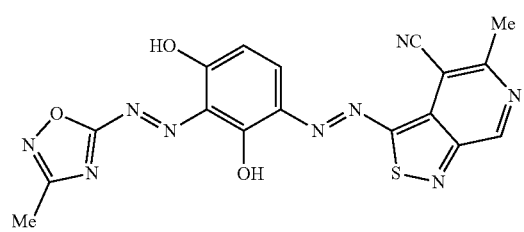
D-33
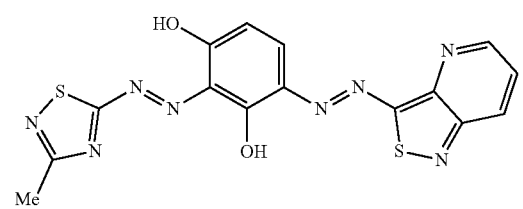
D-34
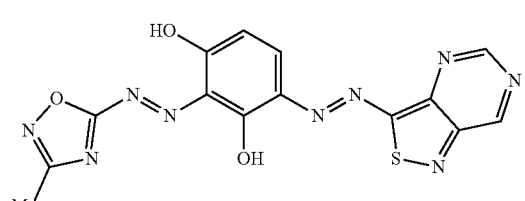
D-35
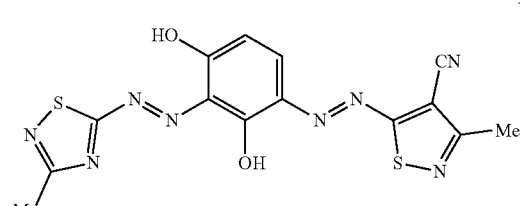
D-36
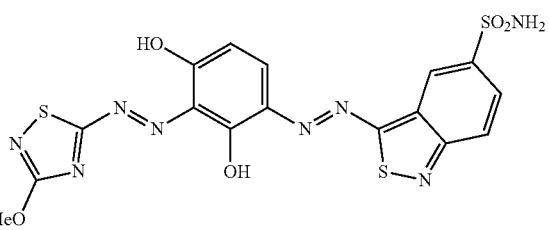
D-37
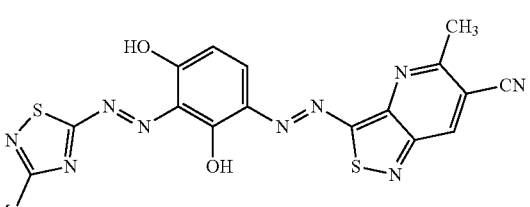
D-38
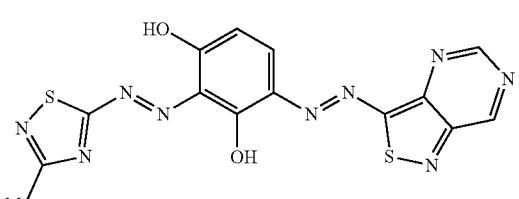
D-39
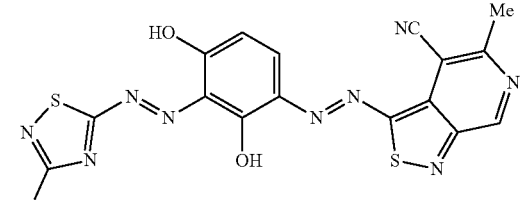
D-40
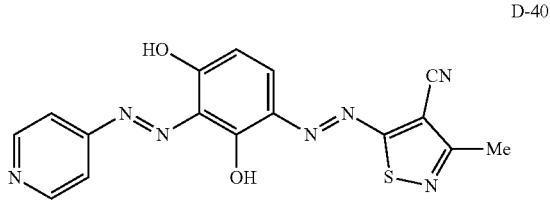
D-41
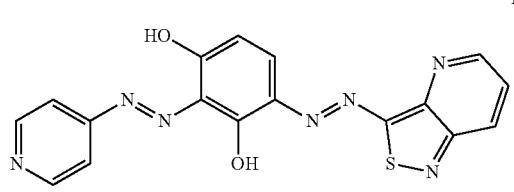
D-42
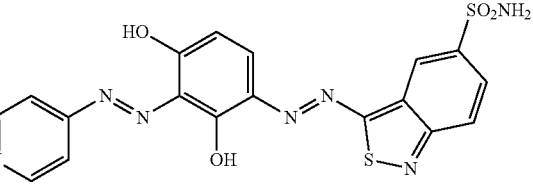
D-43
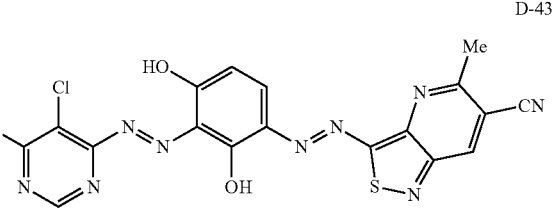

D-44
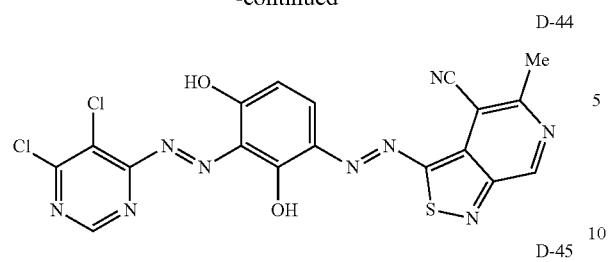
D-45
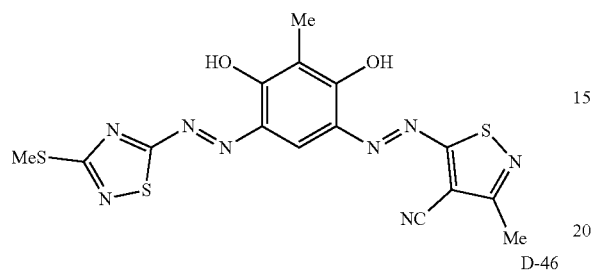
D-46
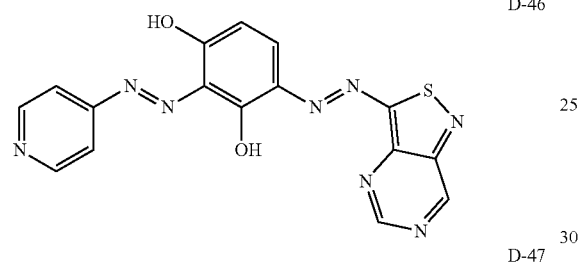
D-47
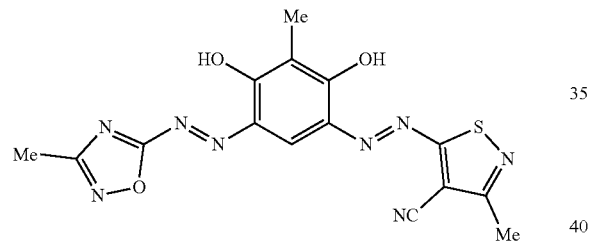
D-48
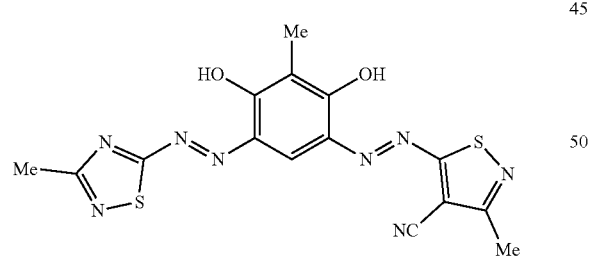
D-49
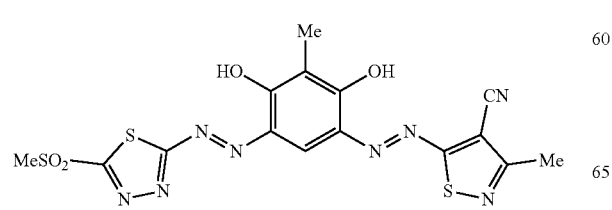
D-50
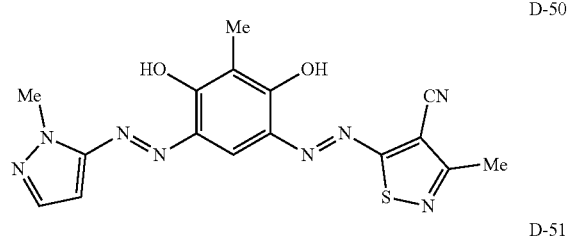
D-51
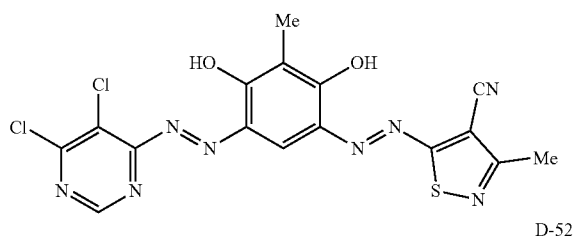
D-52
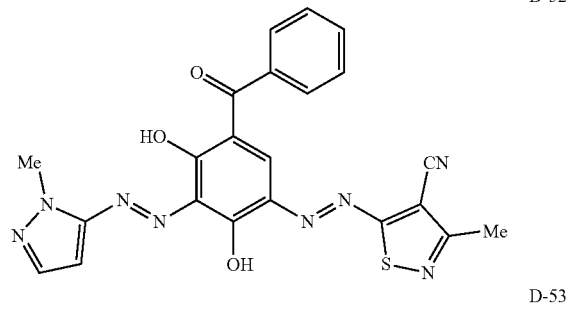
D-53
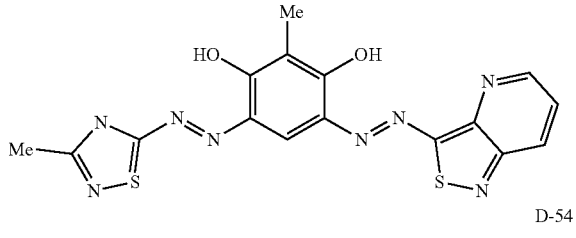
D-54
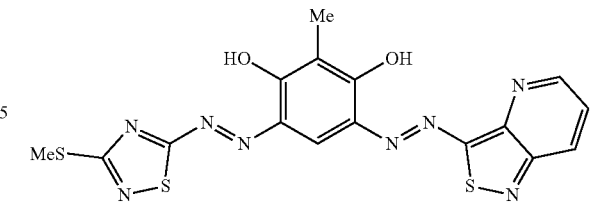
D-55
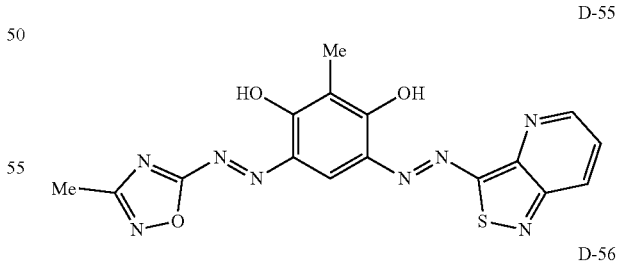
D-56
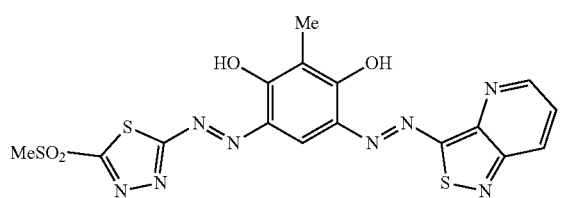

D-57
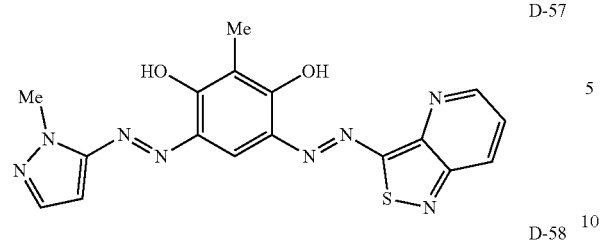
D-58
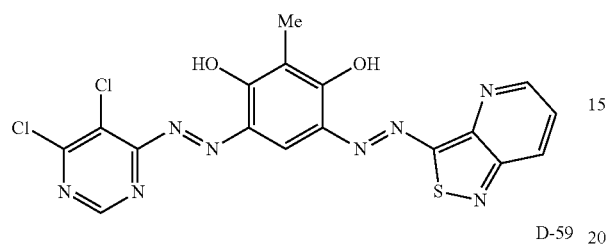
D-59
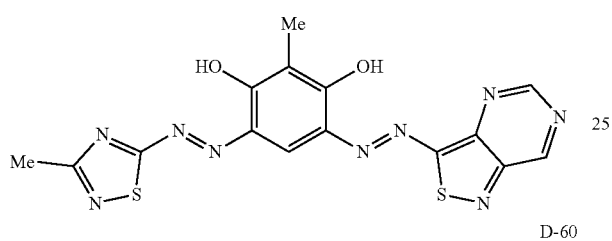
D-60
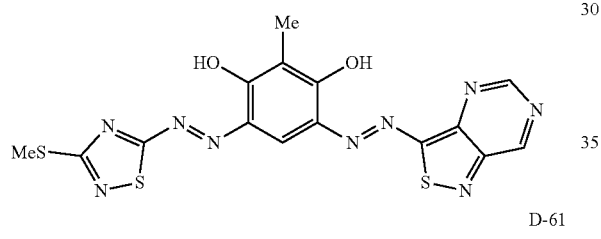
D-61
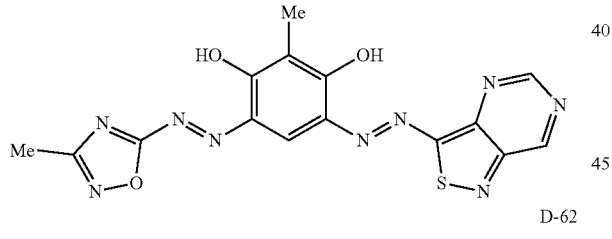
D-62
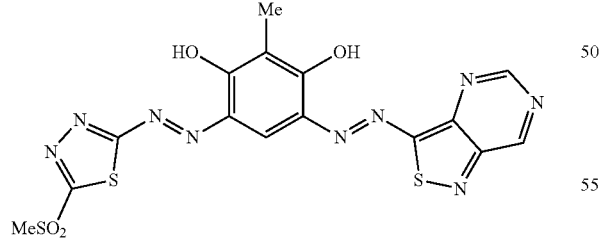
D-63
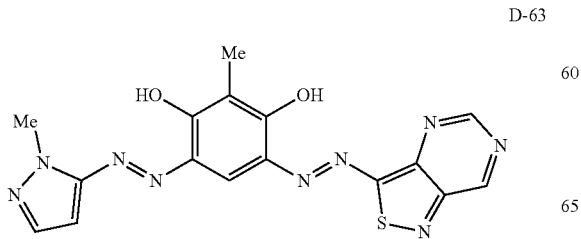
D-64
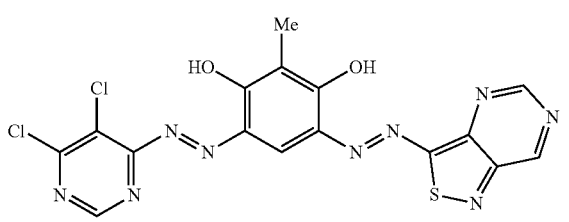
D-65
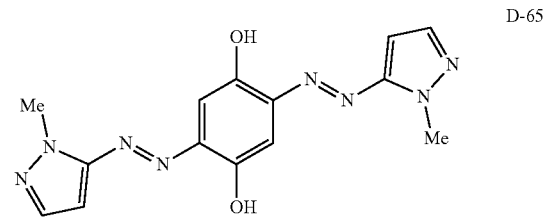
D-66
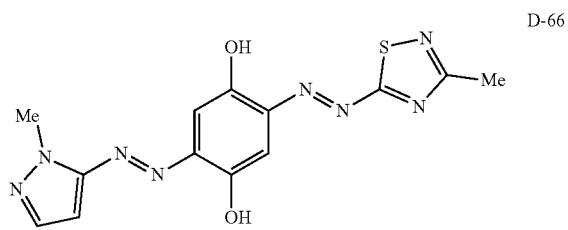
D-67
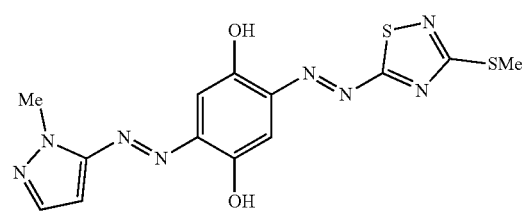
D-68
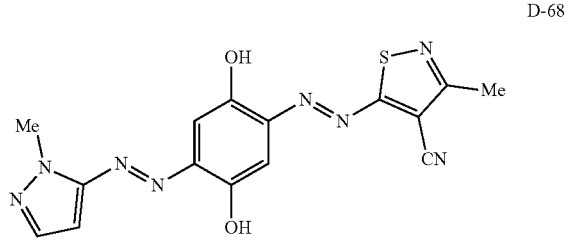
D-69
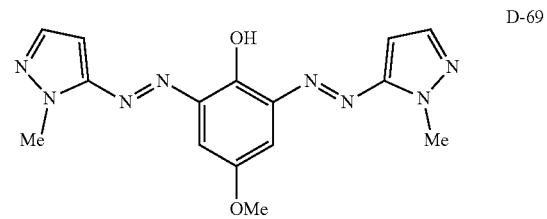
D-70
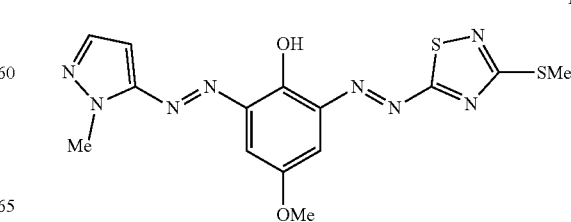

-continued
D-71
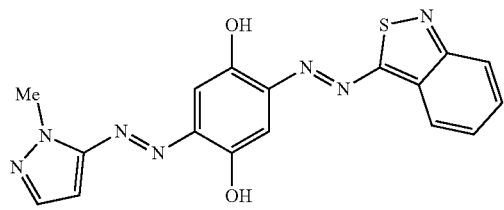
D-72
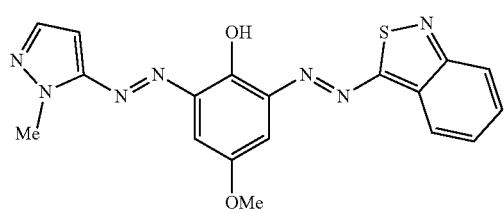
D-73
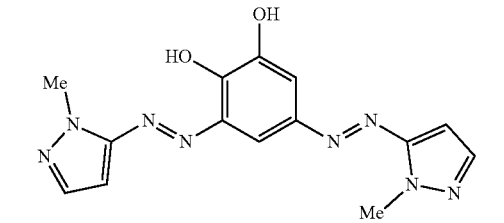
D-74
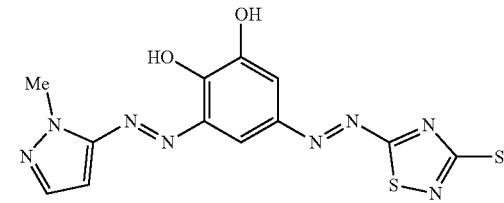
D-75
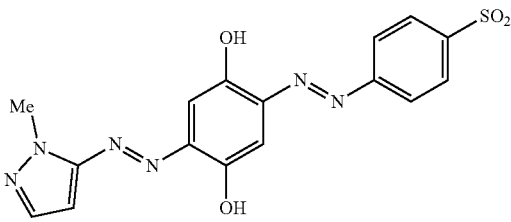
D-76
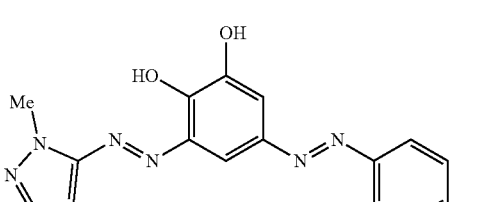
D-77
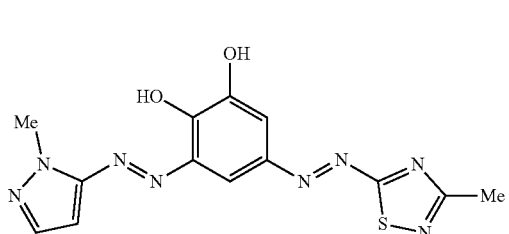
-continued
D-78
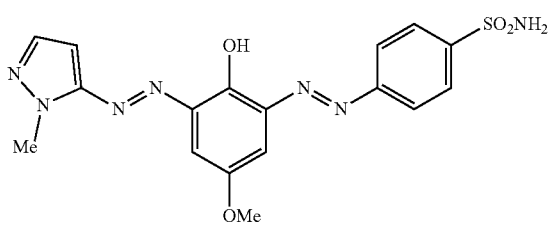
D-79
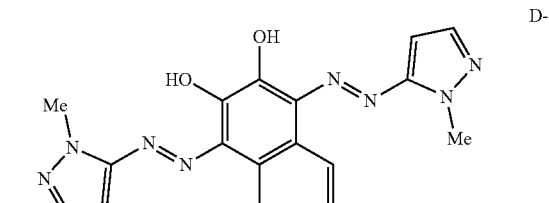
D-80
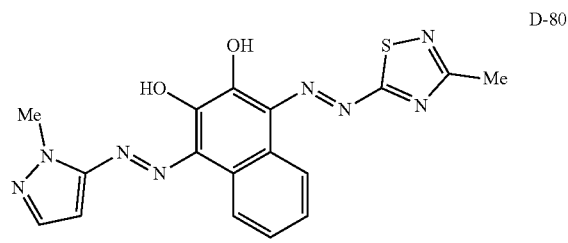
D-81
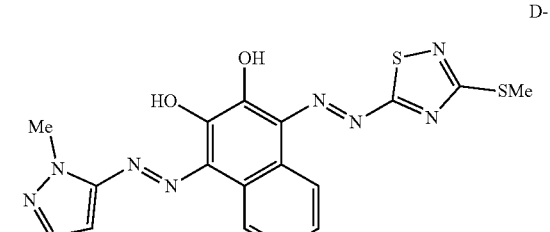
D-82
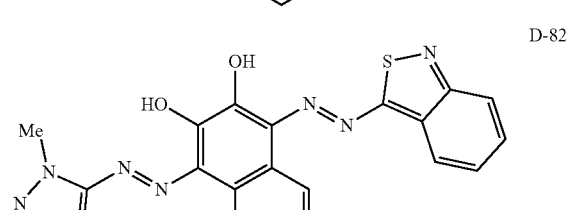
D-83
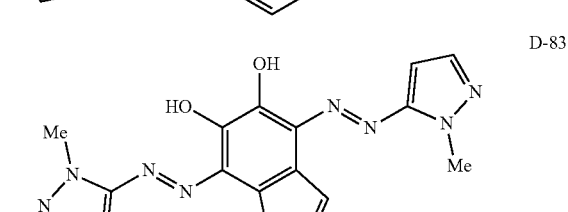
D-84
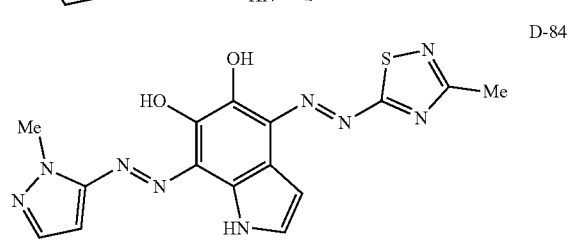

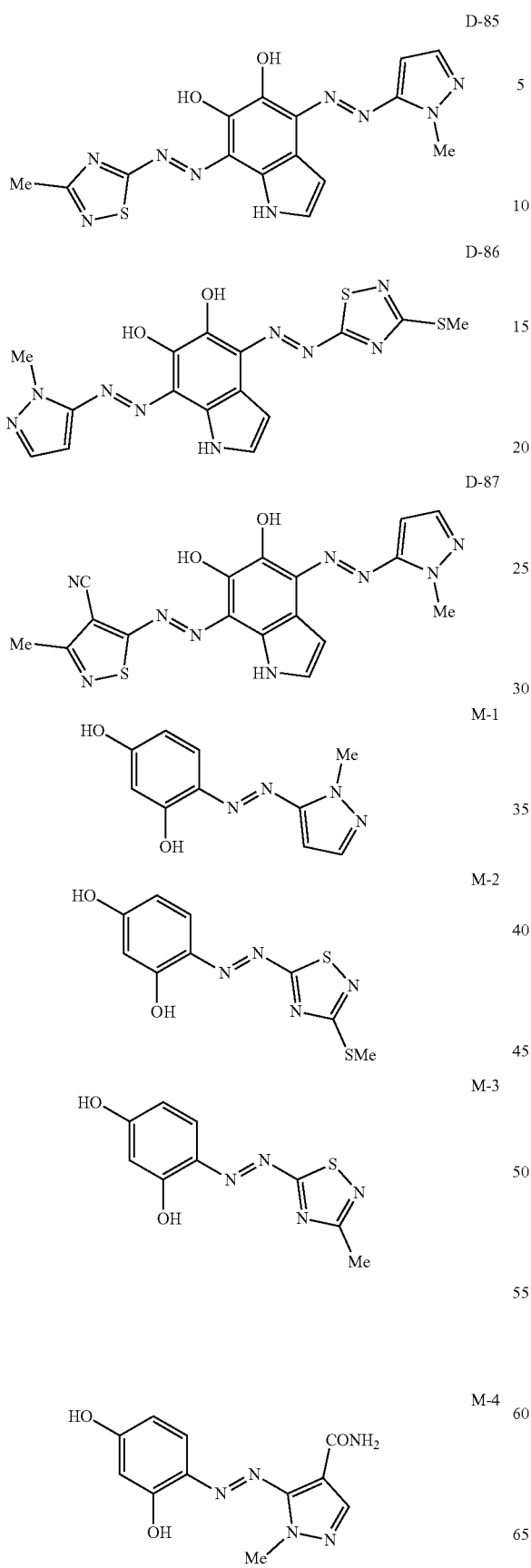
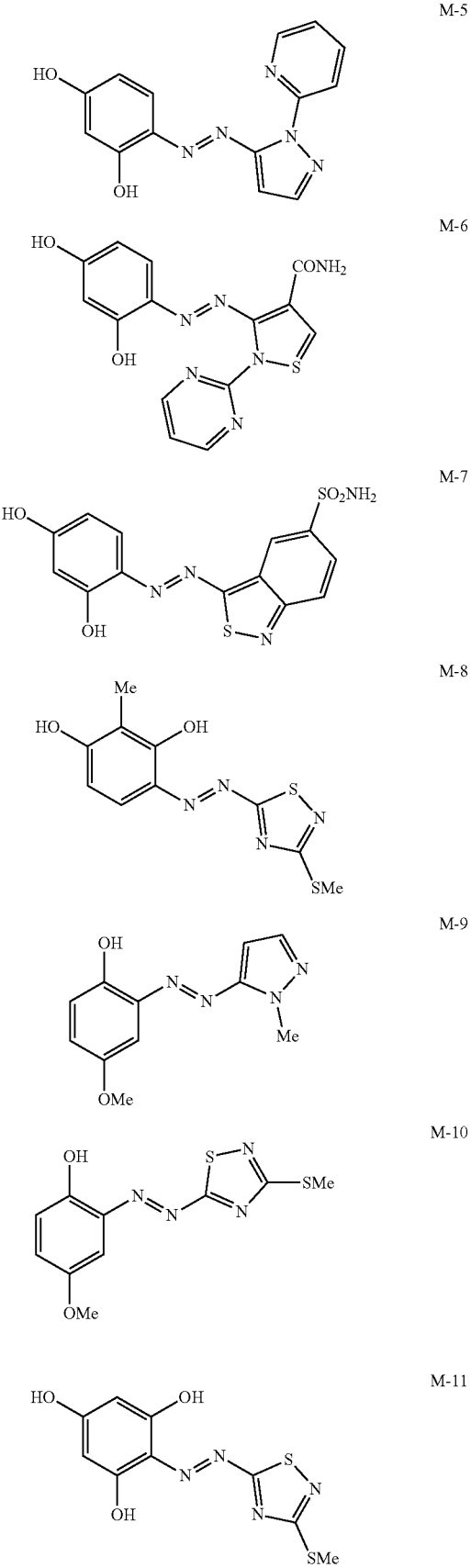

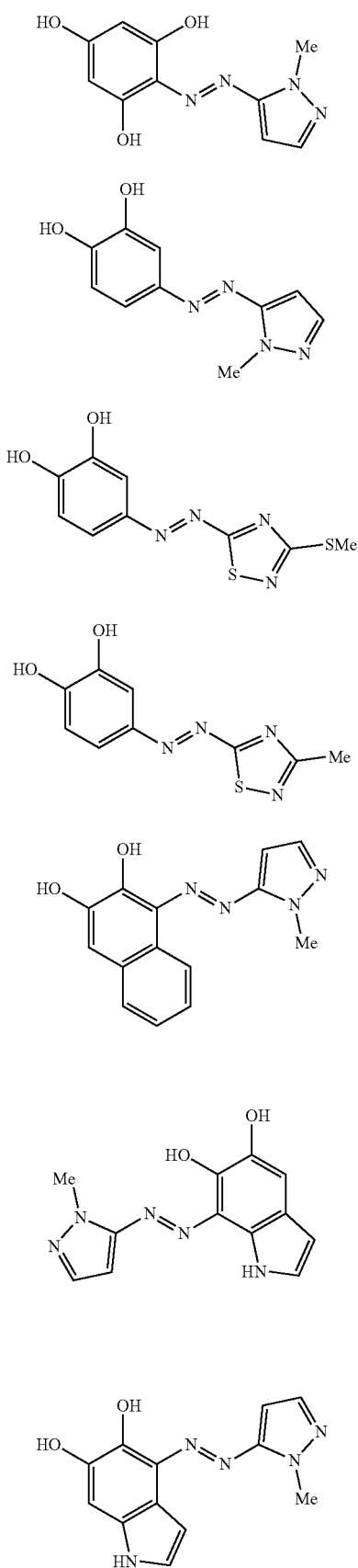
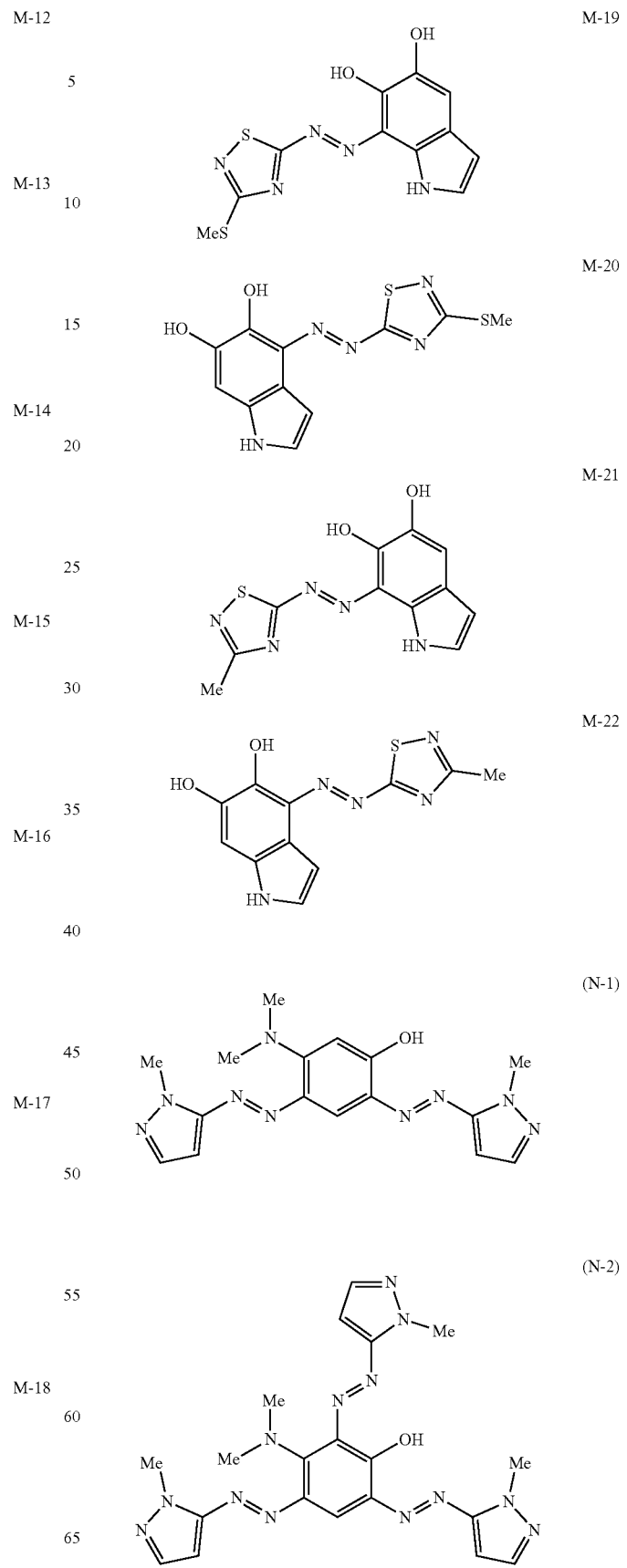

-continued (N-3), (N-4), (N-5), (N-6), (N-7), (N-8), (N-9), (N-10), (N-11)

(N-12) 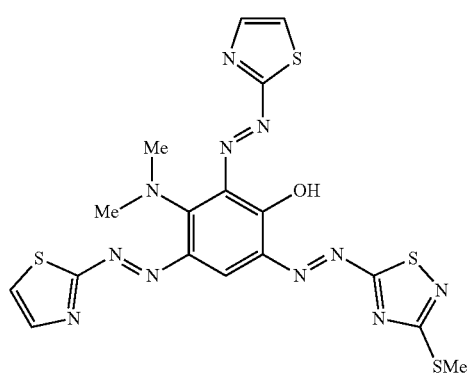
(N-13) 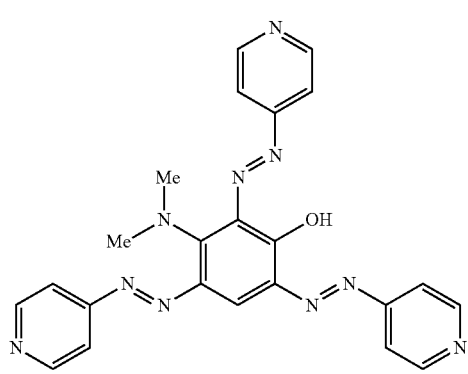
(N-14) 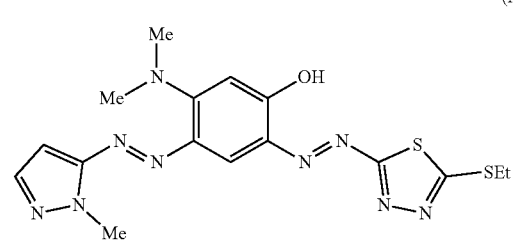
(N-15) 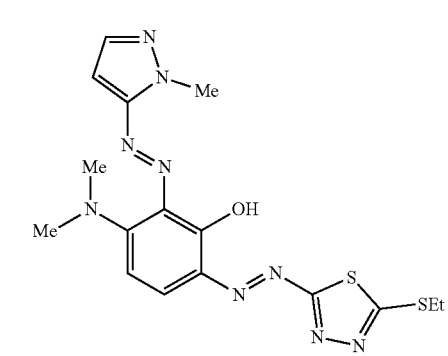
(N-16) 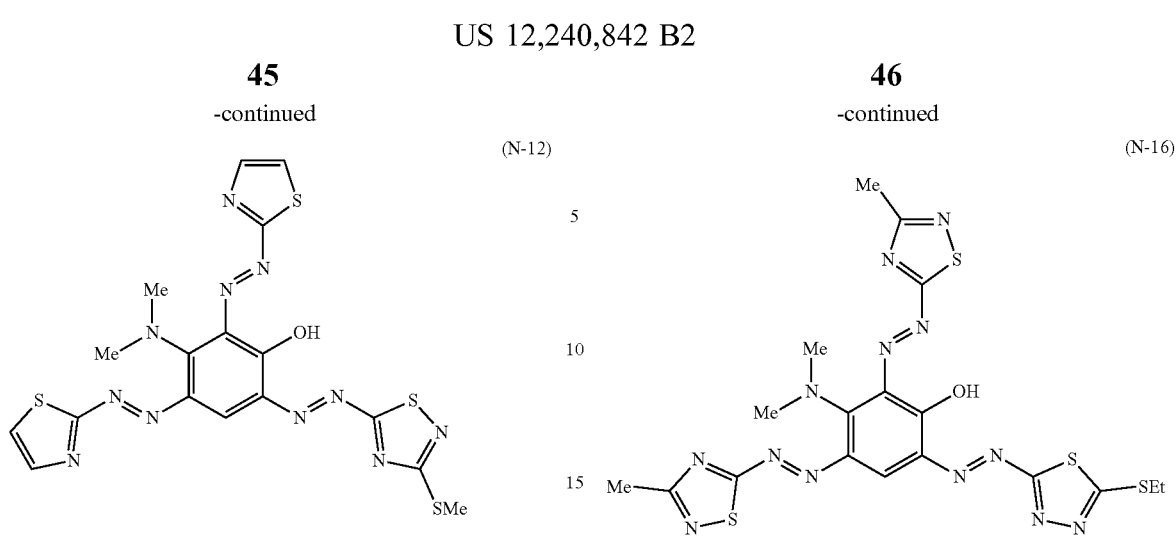
(N-17) 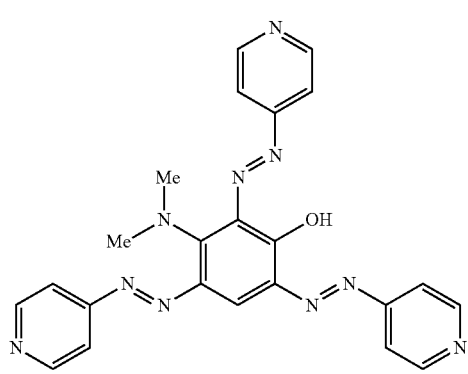
(N-18) 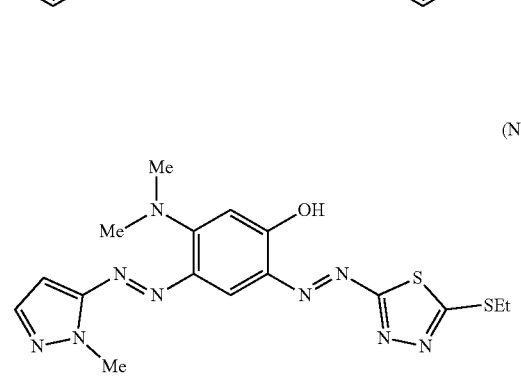
(N-19) 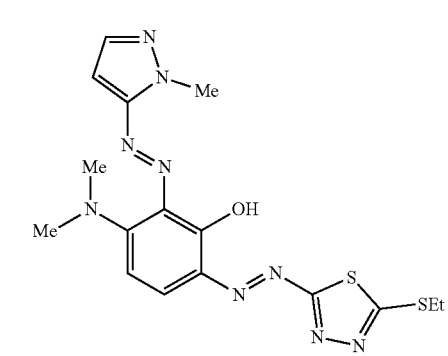

-continued
(N-20)
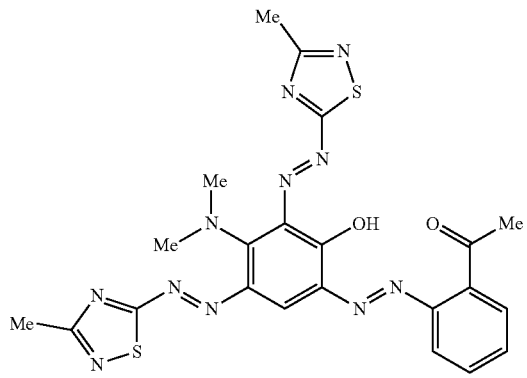
(N-21)
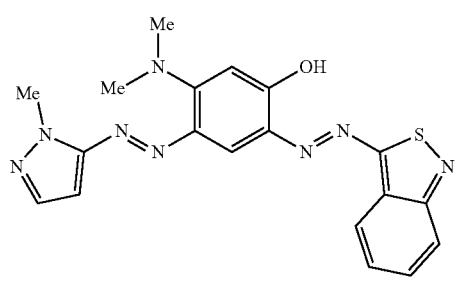
(N-22)
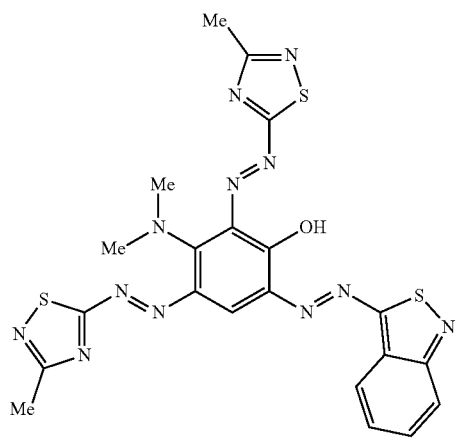
(N-23)
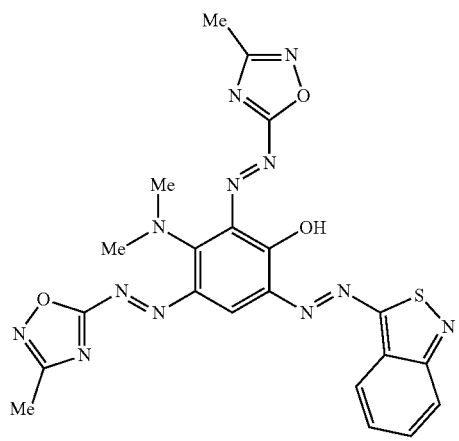
-continued
(N-24)
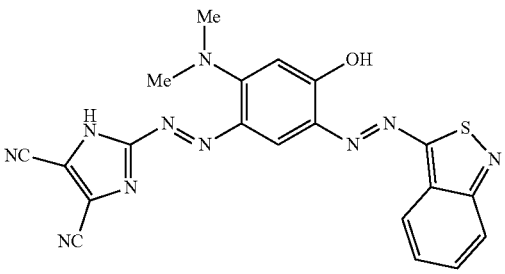
(N-25)
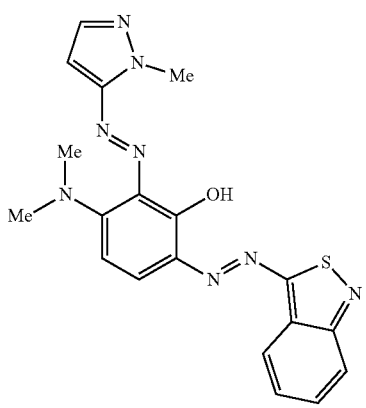
(N-26)
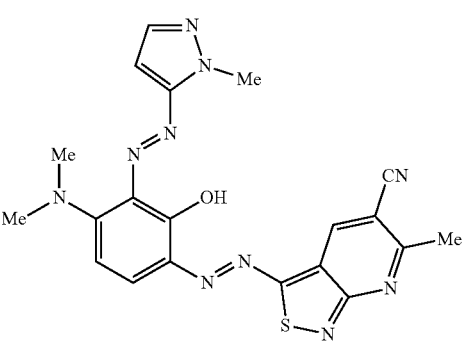
(N-27)
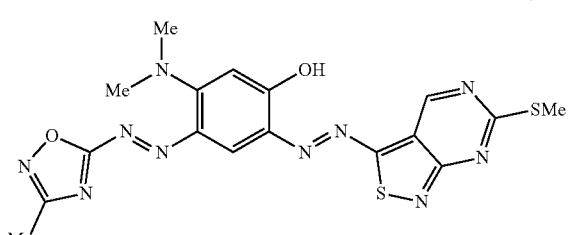
(N-28)
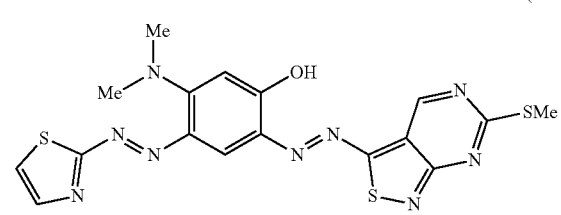

-continued
(N-29)
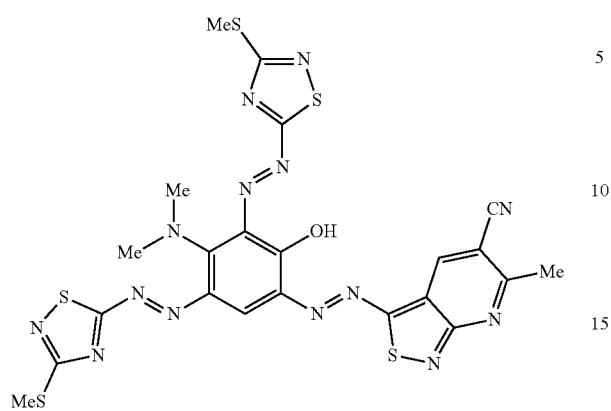
(N-30)
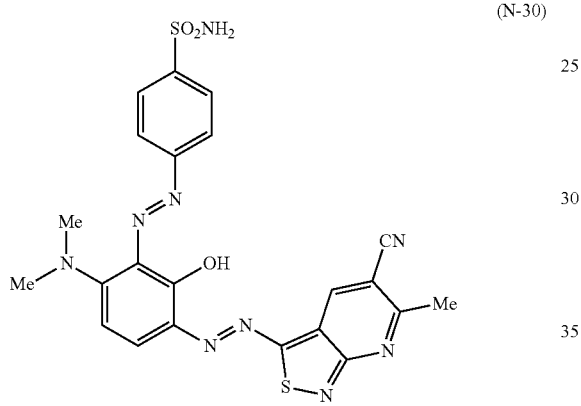
(N-31)
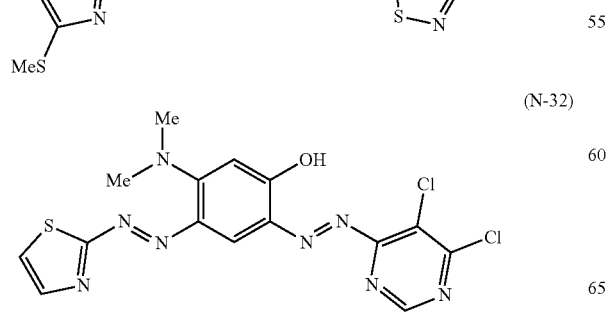
(N-32)
-continued
(N-33)
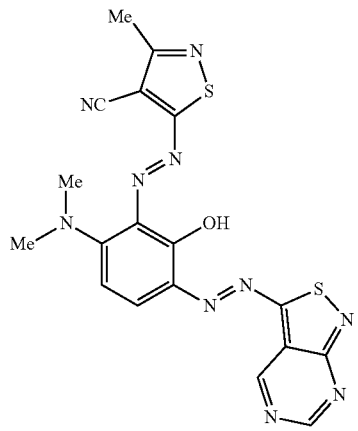
(N-34)
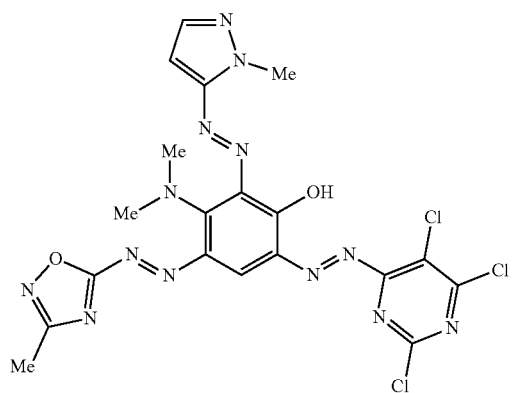
(N-35)
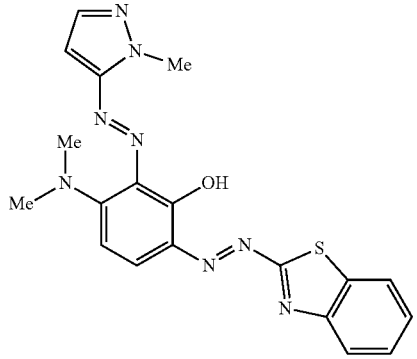
(N-36)
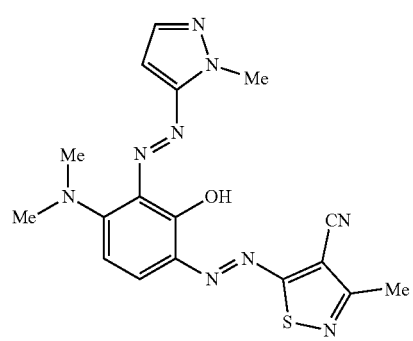

-continued
(N-37)
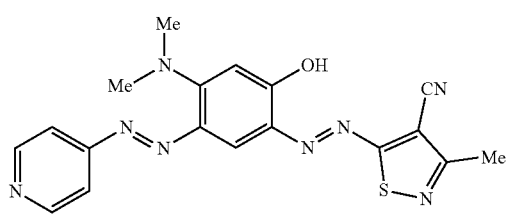
(N-38)
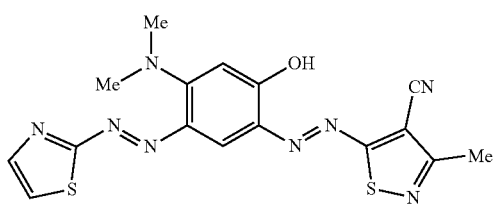
(N-39)
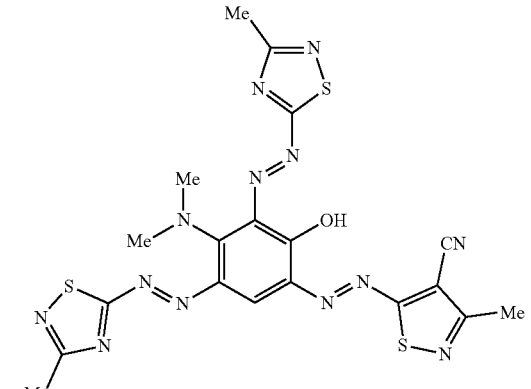
(N-40)
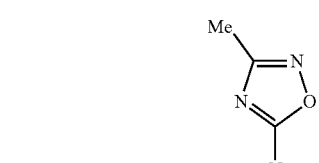
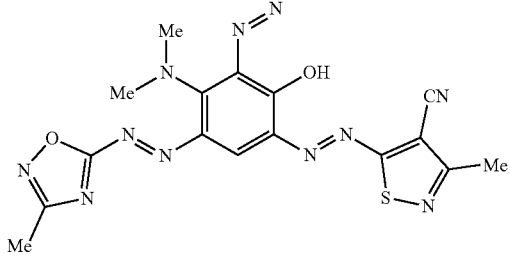
(N-41)
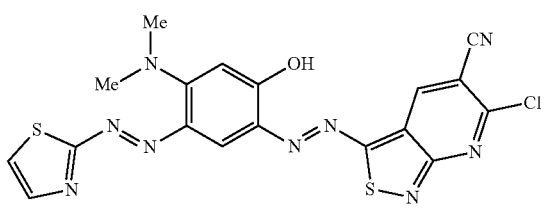
-continued
(N-42)
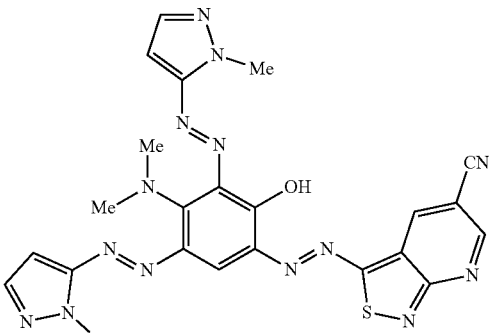
(N-43)
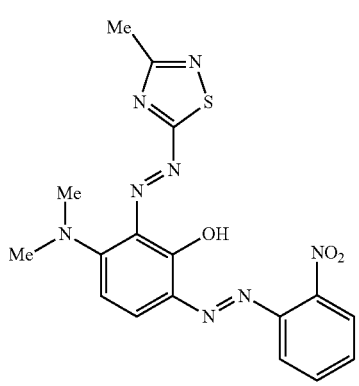
(N-44)
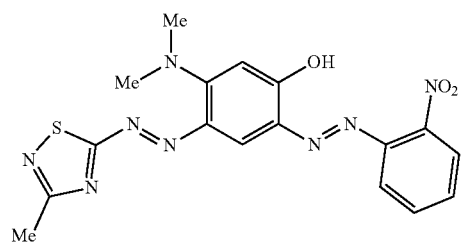
(N-45)

-continued
(N-46)
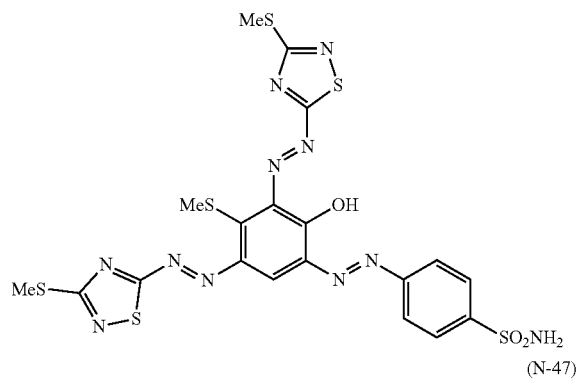
(N-47)
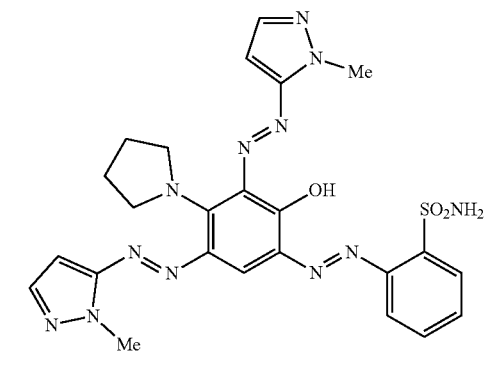
(N-48)
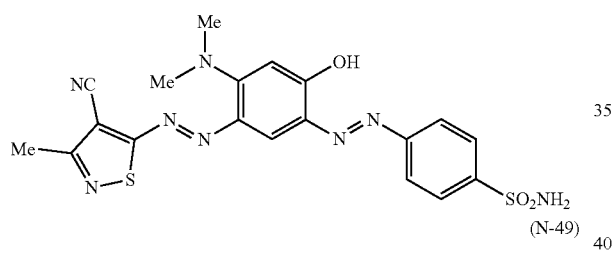
(N-49)
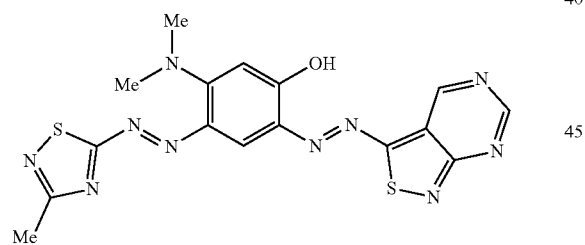
(N-50)
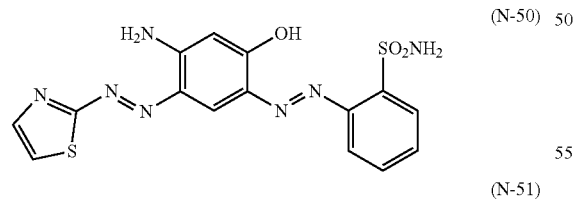
(N-51)
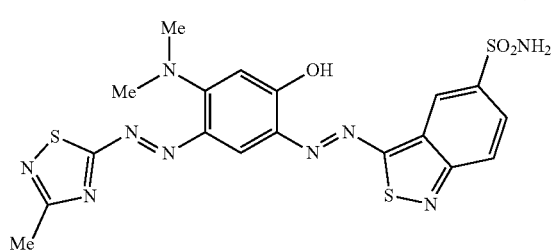
(N-52)
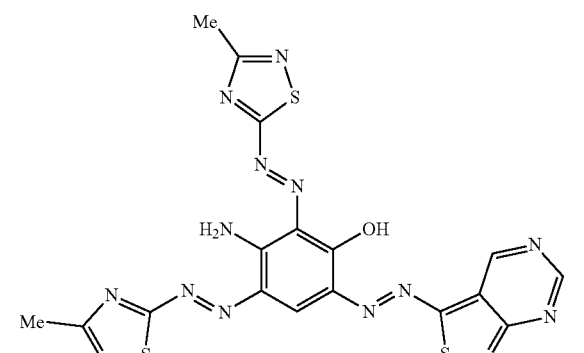
(N-53)
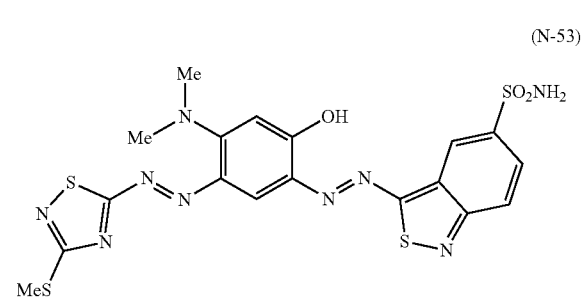
(N-54)
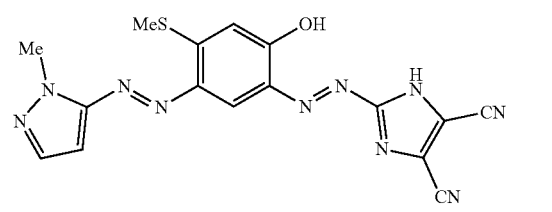
(N-55)
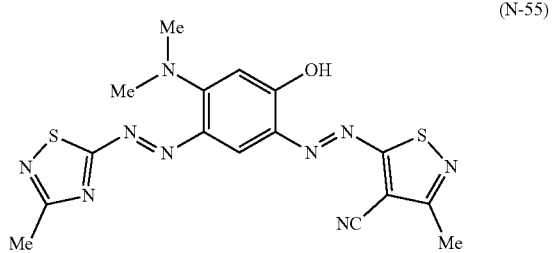
(N-56)
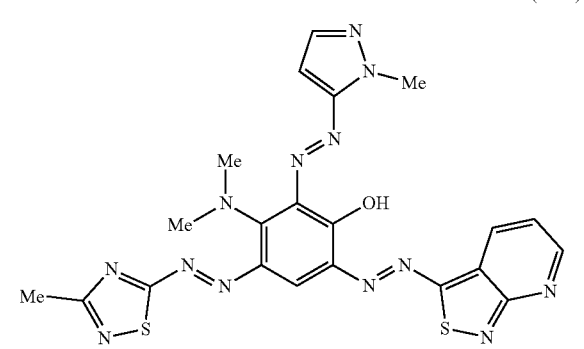

(N-57) (N-58) (N-59) (N-60) (N-61) (N-62) (N-63) (N-64) (N-65) (N-66) (N-67)

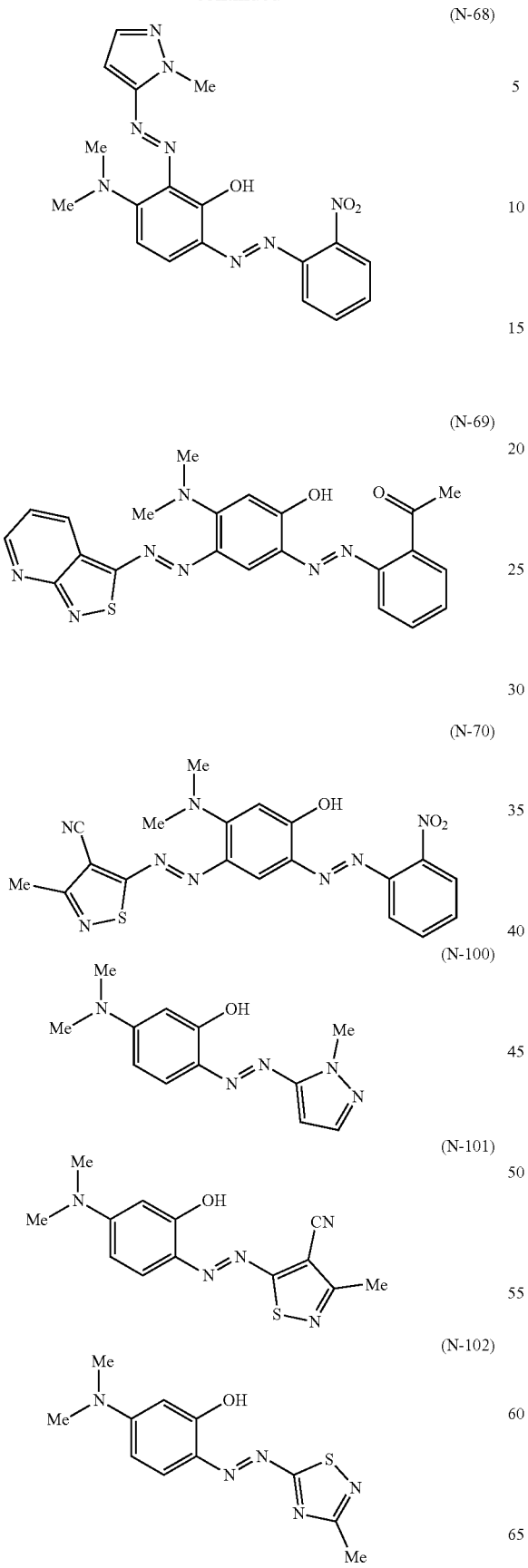
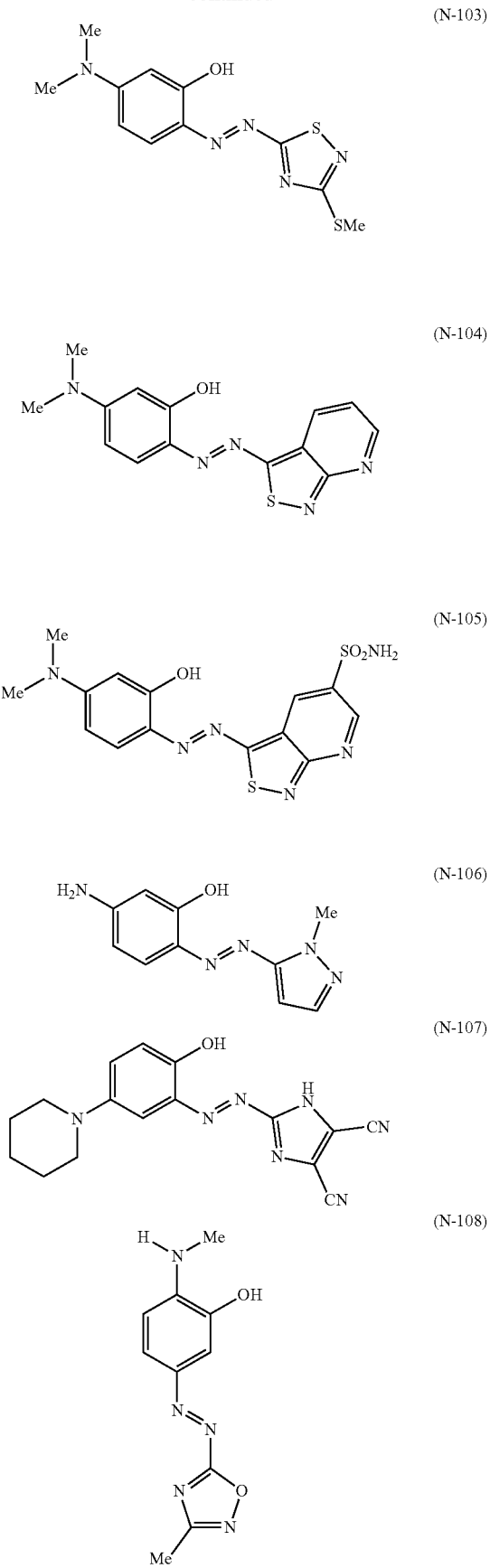

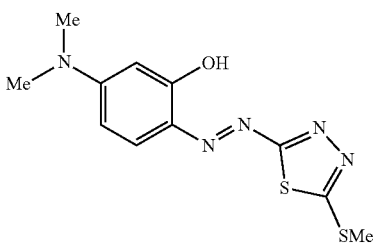

(N-109)

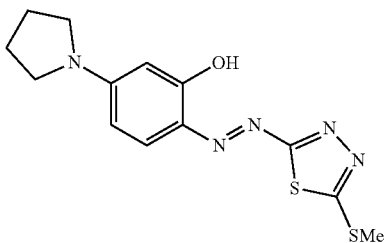

(N-110)

A method for producing the compound represented by Formula 1, the tautomer thereof, and the salt thereof is not particularly limited, and for example, the compound represented by Formula 1, the tautomer thereof, and the salt thereof can be synthesized by the method disclosed in JP2017-515930A.

In a certain aspect of the method for producing the compound represented by Formula 1, the tautomer thereof, and the salt thereof, it is preferable to include a step (also referred to as a "diazotization step 1'") of reacting a diazonium salt represented by Formula 5' with a compound represented by Formula 6 to obtain a compound represented by Formula 7'.

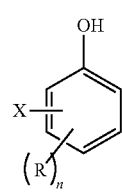

Formula 5'

Formula 6

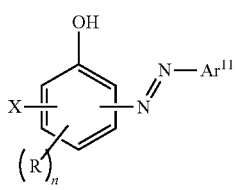

Formula 7'

In Formula 5', Formula 6, and Formula 7', $Ar^{11}$ represents a heterocyclic group, R represents a substituent, X— represents $R^1O$—, $R^{2a}R^{2b}N$—, or $R^3S$—, $R^1$, $R^{2a}$, and $R^{2b}$ each independently represent a hydrogen atom or an alkyl group, $R^3$ represents an alkyl group, n represents 0, 1, 2, or 3, and in a case where n represents 2 or 3, R's may be the same or different from each other.

In addition, in a certain aspect of the method for producing the compound represented by Formula 1, the tautomer thereof, and the salt thereof, it is preferable to include a step (diazotization step 1) of reacting a diazonium salt represented by Formula 5 with a compound represented by Formula 6 to obtain a compound represented by Formula 7 and a step (also referred to as a "diazotization step 2") of reacting the obtained compound represented by Formula 7 with a diazonium salt represented by Formula 8. That is, the method for producing the compound represented by Formula 1, the tautomer thereof, and the salt thereof may have an embodiment including an aspect in which a diazonium salt which is the compound represented by Formula 7 is used as an intermediate and reacted with the diazonium salt represented by Formula 8.

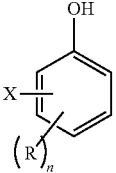

Formula 5

Formula 6

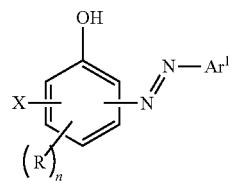

Formula 7

Formula 8

In Formulae 5 to 8, $Ar^1$ and $Ar^2$ each independently represent an aromatic hydrocarbon group or a heterocyclic group, R represents a substituent, X— represents $R^1O$—, R'S—, or $R^1R^2N$—, $R^1$ and $R^2$ each independently represent a hydrogen atom or an alkyl group, n represents 0, 1, 2, or 3, and in a case where n represents 2 or 3, R's may be the same or different from each other. However, $Ar^1$ and $Ar^2$ are not simultaneously aromatic hydrocarbon groups.

In a certain aspect of the method for producing the compound represented by Formula 1, the tautomer thereof, and the salt thereof, it is more preferable to include a step (also referred to as a "diazotization step 3") of reacting a diazonium salt represented by Formula 5 with a compound represented by Formula 10 to obtain a compound represented by Formula 11 and a step (also referred to as a "diazotization step 4") of reacting the obtained compound represented by Formula 11 with a diazonium salt represented by Formula 8 to obtain a compound represented by Formula 12.

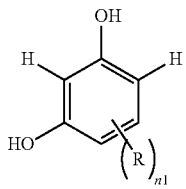

Formula 5

Formula 10

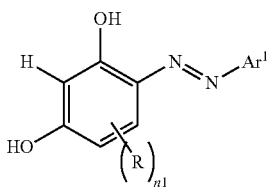

Formula 11

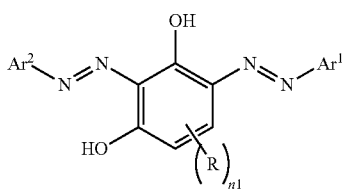

Formula 12

In Formula 5, Formula 8, and Formulae 10 to 12, $Ar^1$ and $Ar^2$ each independently represent an aromatic hydrocarbon group or a heterocyclic group, R represents a substituent, n1 represents 0, 1, or 2, and in a case where n1 represents 2, R's may be the same or different from each other. However, $Ar^1$ and $Ar^2$ are not simultaneously aromatic hydrocarbon groups.

In addition, in a certain aspect of the method for producing the compound represented by Formula 1, the tautomer thereof, and the salt thereof, it is more preferable to include a step (also referred to as a "diazotization step 5") of reacting a diazonium salt represented by Formula 5 with a compound represented by Formula 13 to obtain a compound represented by Formula 14 and a step (also referred to as a "diazotization step 6") of reacting the obtained compound represented by Formula 14 with a diazonium salt represented by Formula 8 to obtain a compound represented by Formula 15.

Formula 5

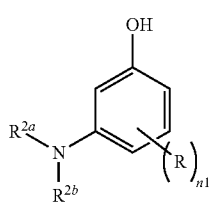

Formula 13

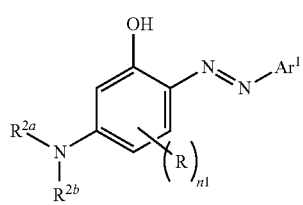

Formula 14

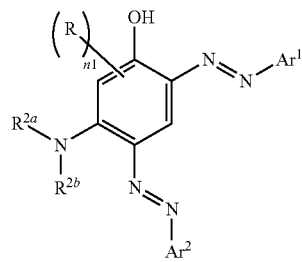

Formula 8

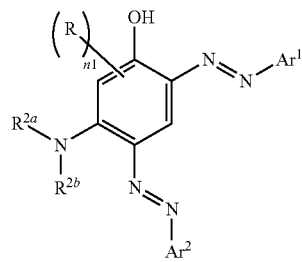

Formula 15

In Formula 5, Formula 8, and Formulae 13 to 15, $Ar^1$ and $Ar^2$ each independently represent an aromatic hydrocarbon group or a heterocyclic group. $R^1$ and $R^2$ each independently represent a hydrogen atom or an alkyl group, $R^1$ and $R^2$ may be the same or different from each other, and $R^1$ and $R^2$ may be bonded to each other to form a nitrogen-containing hetero ring. R represents a substituent, n1 represents 0, 1, or 2, and in a case where n1 represents 2, R's may be the same or different from each other. However, $Ar^1$ and $Ar^2$ are not simultaneously aromatic hydrocarbon groups.

$Ar^{11}$ in Formula 5' and Formula 7' has the same definition as Ar in Formula 1, and preferred aspects thereof are also the same.

$Ar^1$ and $Ar^2$ in Formula 5 and Formulae 7 and 8 each independently have the same definition as Ar in Formula 1, and preferred aspects thereof are also the same.

X—, R, and n in Formulae 6 and 7 and Formula 7' each independently have the same definition as X—, R, and n in Formula 1, and preferred aspects thereof are also the same.

$Ar^1$, $Ar^2$, R, $R^1$, and n1 in Formulae 10 to 12 each independently have the same definition as $Ar^1$, $Ar^2$, R, $R^1$, and n1 in Formula A1, and preferred aspects thereof are also the same.

$Ar^1$, $Ar^2$, R, $R^{2a}$ and $R^{2b}$, and n1 in Formulae 13 to 15 each independently have the same definition as $Ar^1$, $Ar^2$, R, $R^{2a}$ and $R^{2b}$, and n1 in Formula A1, and preferred aspects thereof are also the same.

A method for producing the diazonium salt represented by Formula 5', Formula 5, or Formula 8 is not particularly limited, and the diazonium salt may be prepared by a known method or with reference to a known method. Specific suitable examples thereof include a method of producing a diazonium salt by reacting an amino group of an amine compound with sodium nitrite or nitrosyl sulfate.

In addition, a counter anion of the diazonium salt represented by Formula 5 or Formula 8 is not particularly limited, and a known anion can be used.

In addition, in the diazotization step 1' and diazotization steps 1 to 6 described above, known reaction conditions of diazo coupling (for example, reaction temperature, reaction time, reaction solvent, and the like) can be used.

Furthermore, a molar ratio of reactants in the diazotization step 1' and diazotization steps 1 to 6 described above is not particularly limited, and can be appropriately selected depending on the rarity, reactivity, and the like of each reactant.

<Uses>

The compound represented by Formula 1, the tautomer thereof, and the salt thereof are preferably used as a coloring composition, and it is more preferable to use as a coloring composition containing an aqueous solvent, and the compound represented by Formula 1, the tautomer thereof, and the salt thereof.

In addition, since the compound represented by Formula 1, the tautomer thereof, the salt thereof, or the above-described coloring composition has a special hue with low chroma saturation, they can be suitably used as a coloring agent, and can be more suitably used as a dyeing agent.

In addition, examples of uses of the compound represented by Formula 1, the tautomer thereof, and the salt thereof include black matrix used in displays such as liquid crystal displays (LCD) and plasma display panels (PDP), a curable composition for producing the black matrix, and a color image recording material for forming a color image. Specific examples thereof include uses for an ink jet recording material (for example, ink for ink jet recording), a sublimation thermosensitive recording material, an electrophotographic recording material (for example, a color toner), a transfer type silver halide photosensitive material, a printing ink, a recording pen, or a fiber dyeing, and preferred examples thereof include uses for an ink jet recording material, a transfer type silver halide photosensitive material, a printing ink, or a fiber dyeing.

The compound represented by Formula 1, the tautomer thereof, or the salt thereof can be used with optimizing physical properties such as solubility and dispersibility, suitable for the uses, by adjusting the substituent. In addition, the compound represented by Formula 1, the tautomer thereof, or the salt thereof can be used in a dissolved state, an emulsified dispersed state, or a solid dispersed state depending on the system used.

(Coloring Composition)

The coloring composition according to the embodiment of the present disclosure contains the compound represented by Formula 1, the tautomer thereof, or the salt thereof, and from the viewpoint of dyeing properties, it is more preferable to further contain an aqueous solvent.

The coloring composition according to the embodiment of the present disclosure may contain one type of the compound represented by Formula 1, the tautomer thereof, or the salt thereof alone, or may contain two or more types thereof. In addition, the coloring composition according to the embodiment of the present disclosure may also be combined with other direct dyes or dispersed dyes.

The coloring composition according to the embodiment of the present disclosure can contain a medium.

The coloring composition according to the embodiment of the present disclosure can be produced by dissolving and/or dispersing at least one kind selected from the group consisting of the compound represented by Formula 1, the tautomer thereof, and the salt thereof using, as the medium, a lipophilic medium and/or an aqueous medium. A case where an aqueous medium is used is preferable, and a case where an aqueous solvent is used is more preferable.

A content of the compound represented by Formula 1, the tautomer thereof, and the salt thereof contained in the coloring composition according to the embodiment of the present disclosure is determined by the type of the substituent used in the compound represented by Formula 1, the tautomer thereof, and the salt thereof, and the type of a solvent component used to produce the coloring composition, and the content of the compound represented by Formula 1, the tautomer thereof, and the salt thereof in the coloring composition is preferably 0.001% by mass to 30% by mass, more preferably 0.001% by mass to 20% by mass, still more preferably 0.1% by mass to 10% by mass, and particularly preferably 0.5% by mass to 10% by mass with respect to the total mass of the coloring composition.

In a case where the content of the compound represented by Formula 1, the tautomer thereof, and the salt thereof is 0.001% by mass or more, a coloring density of the coloring agent on a medium to be colored can be ensured. In addition, in a case where the content of the compound represented by Formula 1, the tautomer thereof, and the salt thereof is 30% by mass or less, a coloring composition having a low viscosity can be prepared, which facilitates handling.

In a case of containing an aqueous solvent (preferably, water), the coloring composition according to the embodiment of the present disclosure can be used at any pH, but from the viewpoint of stability and dyeing properties of the compound, the pH is preferably in a range of 5 to 11 and more preferably in a range of 6 to 11, and from the viewpoint of stability and dyeing properties of the compound represented by Formula 1, the tautomer thereof, and the salt thereof, the pH is particularly preferably in a range of 7 to 11.

The value of pH in the present disclosure is a value at 25° C.

The coloring composition according to the embodiment of the present disclosure may contain a pH adjusting agent.

Examples of the pH adjusting agent used in the coloring composition according to the embodiment of the present disclosure include sodium hydroxide, potassium hydroxide, sodium carbonate, potassium carbonate, sodium hydrogen carbonate, potassium hydrogen carbonate, ammonia, monoethanolamine, diethanolamine, and guanidine.

The coloring composition according to the embodiment of the present disclosure can contain a surfactant. Examples of the surfactant which can be used include an anionic surfactant, a nonionic surfactant, a cationic surfactant, and an amphoteric or diionic surfactant. In addition, the above-described surfactants may be used alone or in combination of two or more kinds thereof.

Examples of the anionic surfactant which can be used in the coloring composition according to the embodiment of the present disclosure include monoalkylsulfate or a salt thereof, alkylbenzenesulfonic acid or a salt thereof, and α-olefin sulfonate or a salt thereof. In particular, examples thereof include sodium dodecyl benzene sulfonate, sodium dodecyl sulfate, alkaline salt of sulfosuccinic acid half ester such as disodium monooctyl sulfosuccinate, and alkaline salt of chain monoalkylethoxy sulfosuccinate.

Examples of the nonionic surfactant which can be used in the coloring composition according to the embodiment of the present disclosure include alkyl polyglycosides, sorbitan esters, and acetylene glycols.

Preferred examples of the cationic surfactant which can be used in the coloring composition according to the embodiment of the present disclosure include quaternary ammonium compounds, and more preferred examples thereof include quaternary ammonium compounds having a long-chain alkyl group (for example, alkyl group having 10 or more carbon atoms, preferably alkyl group having 10 to 24 carbon atoms). Examples thereof include cetyltrimethylammonium chloride, dimethyl stearylammonium chloride, trimethylacetylammonium bromide, stearyltrimethylammonium chloride, dimethyl stearylbenzylammonium chloride, benzyltetradecyldimethylammonium chloride, dimethyl di-hydrogenated-tallow ammonium chloride, lauryldimethylbenzylammonium chloride, behenyltrimethylammonium chloride, lauryltrimethyl ammonium chloride, tris(oligooxy-ethyl)alkylammonium phosphate, and cetylpyridinium chloride.

Examples of the amphoteric or diionic surfactant which can be used in the coloring composition according to the embodiment of the present disclosure include betaines such as fatty acid-amidoalkyl betaine and sulfobetaine (for example, lauryl hydroxysulfobetaine).

In a case where the coloring composition according to the embodiment of the present disclosure is used as an aqueous coloring composition, the coloring composition according to the embodiment of the present disclosure preferably contains an aqueous solvent.

Examples of the aqueous solvent include water, an organic solvent soluble in water (preferably, soluble at 25° C.), and a mixed solvent thereof.

Examples of the aqueous solvent which can be used include water, methanol, ethanol, isopropanol, n-propanol, butanol, n-pentanol, propylene glycol, ethylene glycol monoethyl ether, 1,2-hexanediol, butoxyethanol, phenoxyethanol, benzyl alcohol, propylene carbonate, and a mixture thereof. Among these, 1,2- or 1,3-propanediol, 1-methoxy-2-propanol, 1-ethoxy-2-propanol, 1,3- or 1,4-butanediol, diethylene glycol, diethylene glycol monomethyl or monoethyl ether, dipropylene glycol, or dipropylene glycol monomethyl or monoethyl ether is preferable.

In a case where the coloring composition according to the embodiment of the present disclosure is used as an aqueous coloring composition, a content of the compound represented by Formula 1, the tautomer thereof, and the salt thereof is preferably 0.001% by mass to 30% by mass, more preferably 0.001% by mass to 20% by mass, still more preferably 0.1% by mass to 10% by mass, and particularly preferably 0.5% by mass to 10% by mass with respect to the total mass of the coloring composition.

In addition, as the aqueous solvent, monohydric alcohols such as methanol, ethanol, isopropanol, and n-propanol; polyhydric alcohols such as glycerin and hexanetriol; ethyl carbitol; benzyl alcohol; benzyloxy ethanol; propylene carbonate (4-methyl-1,3-dioxan-2-one); n-alkylpyrrolidone; and urea may be used in combination.

The coloring composition according to the embodiment of the present disclosure can contain a viscosity improver.

Examples of the viscosity improver include oleic acid, cetyl alcohol, oleyl alcohol, sodium chloride, cetearyl alcohol, and stearyl alcohol.

A content of the viscosity improver is preferably 0.05% by mass to 20% by mass, more preferably 0.1% by mass to 10% by mass, and particularly preferably 0.5% by mass to 5% by mass with respect to the total mass of the coloring composition.

The coloring composition according to the embodiment of the present disclosure may contain a coloring compound (pigment, dye, or the like) other than the compound represented by Formula 1, the tautomer thereof, and the salt thereof.

Any yellow dye can be used as a yellow dye which can be used. Examples thereof include aryl or heteryl azo dyes, azomethine dyes, methine dyes, and quinone dyes, and examples of other dye types include quinophthalone dyes, nitro-nitriso dyes, acrydin dyes, and acridinone dyes.

Any magenta dye can be used as a magenta dye which can be used. Examples thereof include aryl or heteryl azo dyes, azomethine dyes, methine dyes, carbonium dyes such as diphenylmethane dye, triphenylmethane dye, and xanthene dye, quinone dyes such as naphthoquinone, anthraquinone, and anthrapyridone, and condensed polycyclic dyes such as dioxazine dye.

Any cyan dye can be used as a cyan dye which can be used. Examples thereof include aryl or heteryl azo dyes, azomethine dyes, polymethine dyes such as cyanine dye, oxonol dye, and merocyanine dye, carbonium dyes such as diphenylmethane dye, triphenylmethane dye, and xanthene dye, phthalocyanine dyes, anthraquinone dyes, indigo or thioindigo dyes.

In addition, a black dye can also be contained. Examples of the black dye which can be used include dissazo, trisazo, and tetraazo dyes, and a dispersion of carbon black.

In addition, the coloring composition according to the embodiment of the present disclosure may contain a binder polymer, a polymerizable compound, a polymerization initiator, and the like. As the binder polymer, the polymerizable compound, and the polymerization initiator, known ones can be used.

Examples of other additives which can be used in the coloring composition according to the embodiment of the present disclosure include silicone oil, hydrocarbon oil, polyolefin, and fatty acid ester.

In the coloring composition according to the embodiment of the present disclosure, as necessary, other additives can be blended within a range that does not impair the effects of the present disclosure. Examples of the additives in each use will be described later.

<Color Toner>

In a case where the coloring composition according to the embodiment of the present disclosure is used as a coloring composition for a color toner, a content of the compound represented by Formula 1, the tautomer thereof, and the salt thereof in the coloring composition for a color toner is preferably 0.1 parts by mass or more, more preferably 1 part by mass to 20 parts by mass, and particularly preferably 2 parts by mass to 10 parts by mass with respect to 100 parts by mass of the coloring composition for a color toner.

In a case where the coloring composition according to the embodiment of the present disclosure is used as a coloring composition for a color toner, the coloring composition for a color toner preferably contains a binder resin.

As the binder resin, any commonly used binder resin can be used. Examples thereof include a styrene resin, an acrylic resin, a styrene/acrylic resin, and a polyester resin.

In a case where the coloring composition according to the embodiment of the present disclosure is used as a coloring composition for a color toner, inorganic particles and/or organic particles can be externally added for the purpose of fluidity, charge control, and the like of the coloring composition for a color toner. For example, silica particles or titania particles which are surface-treated with an alkyl group-containing coupling agent or the like are preferable. A number-average primary particle diameter of these particles is preferably 10 nm to 500 nm, and it is preferable that these particles are added to the toner in an amount of 0.1% by mass to 20% by mass.

In a case where the coloring composition according to the embodiment of the present disclosure is used as a coloring composition for a color toner, the coloring composition for a color toner preferably contains a mold release agent.

As the mold release agent, any mold release agent used in the related art can be used. Specific examples thereof include polyolefins such as low-molecular-weight polypropylene and low-molecular-weight polyethylene, an ethylene-propylene copolymer, microcrystalline wax, carnauba wax, sasol wax, and paraffin wax.

A content of the mold release agent is preferably 1% by mass to 5% by mass with respect to the total mass of the composition for a color toner.

In a case where the coloring composition according to the embodiment of the present disclosure is used as a coloring composition for a color toner, the coloring composition for a color toner preferably contains a charge control agent.

Examples of the charge control agent include a quaternary ammonium salt compound and a calixarene compound.

In a case where the coloring composition according to the embodiment of the present disclosure is used as a coloring composition for a color toner, the coloring composition for a color toner can contain a carrier.

As the carrier, non-coated carrier composed only of magnetic material particles such as iron and ferrite or resin-coated carrier in which a surface of the magnetic material particles is coated with resin or the like may be used.

An average particle diameter of the carrier is preferably 30 μm to 150 μm in terms of volume average particle size.

<Ink for Ink Jet Recording>

In a case where the coloring composition according to the embodiment of the present disclosure is used as an ink for ink jet recording, the ink for ink jet recording is preferably an ink obtained by dissolving and/or dispersing the coloring composition in a lipophilic medium or an aqueous medium, and more preferably an ink using an aqueous medium (preferably, an aqueous solvent).

In a case where the coloring composition according to the embodiment of the present disclosure is used as an ink for ink jet recording, in the ink for ink jet recording, as necessary, known additives such as an anti-drying agent (wetting agent), a discoloration preventer, an emulsion stabilizer, a penetration enhancer, an ultraviolet absorber, a preservative, a fungicide, a pH adjusting agent, a surface tension adjuster, a defoamer, a viscosity adjuster, a dispersing agent, a dispersion stabilizer, a rust inhibitor, and a chelating agent.

In a case of a water-soluble ink, these various additives are added directly to an ink liquid. In a case where an oil-soluble dye is used in a form of a dispersion, it is generally added to the dispersion after preparation of a dye dispersion, but it may be added to the oil phase or the aqueous phase during the preparation.

The anti-drying agent is suitably used for the purpose of preventing clogging due to drying of the ink for ink jet recording at an ink jet port of a nozzle used in the ink jet recording method.

As the anti-drying agent, a water-soluble organic solvent having a vapor pressure lower than that of water is preferable. Specific examples thereof include polyhydric alcohols represented by ethylene glycol, propylene glycol, diethylene glycol, polyethylene glycol, thiodiglycol, dithiodiglycol, 2-methyl-1,3-propanediol, 1,2,6-hexanetriol, acetylene glycol derivative, glycerin, trimethylolpropane, and the like; lower alkyl ethers of polyhydric alcohols, such as ethylene glycol monomethyl (or ethyl) ether, diethylene glycol monomethyl (or ethyl) ether, and triethylene glycol monoethyl (or butyl) ether; heterocycles such as 2-pyrrolidone, N-methyl-2-pyrrolidone, 1,3-dimethyl-2-imidazolidinone, and N-ethylmorpholine; sulfur-containing compounds such as sulfolane, dimethylsulfoxide, and 3-sulfolene; polyfunctional compounds such as diacetone alcohol and diethanolamine; and urea derivatives. Among these, polyhydric alcohols such as glycerin and diethylene glycol are more preferable.

In addition, the above-described anti-drying agents may be used alone or in combination of two or more kinds.

It is preferable that these anti-drying agents are contained in the ink for ink jet recording in an amount of 10% by mass to 50% by mass.

The ultraviolet absorber is used for the purpose of improving storage stability of an image.

As the ultraviolet absorber, benzoxazole compounds described in JP1983-185677A (JP-S58-185677A), JP1986-190537A (JP-S61-190537A), JP1990-782A (JP-H2-782A), JP1993-197075A (JP-H5-197075A), JP1997-34057A (JP-H9-34057A), and the like; benzophenone compounds described in JP1971-2784A (JP-S46-2784A), JP1993-194483A (JP-H5-194483A), U.S. Pat. No. 3,214,463A, and the like; cinnamic acid compounds described in JP1973-30492A (JP-S48-30492A), JP1981-21141A (JP-S56-21141A), JP1998-88106A (JP-H10-88106A), and the like; triazine compounds described in JP1992-298503A (JP-H4-298503A), JP1996-53427A (JP-H8-53427A), JP1996-239368A (JP-H8-239368A), JP1998-182621A (JP-H10-182621A), JP1996-501291B (JP-H8-501291B), and the like; compounds described in Research Disclosure No. 24239; and a compound which absorbs ultraviolet rays and emits fluorescence, such as a stilbene-based compound or a benzoxazole-based compound, that is, a so-called fluorescent brightening agent can also be used.

The discoloration preventer is used for the purpose of improving storage stability of an image.

As the discoloration preventer, various organic or metal complex-based discoloration preventers can be used. As the organic discoloration preventer, hydroquinones, alkoxyphenols, dialkoxyphenols, phenols, anilines, amines, indanes, chromans, alkoxyanilines, heterocycles, and the like can be used, and as the metal complex, nickel complexes, zinc complexes, and the like can be used. More specifically, compounds described in patents cited in Research Disclosure No. 17643, Section VII, I and J, Research Disclosure No. 15162, Research Disclosure No. 18716, p. 650, left column, Research Disclosure No. 36544, p. 527, Research Disclosure No. 307105, p. 872, and Research Disclosure No. 15162, or compounds included in the general formulae and compound examples of representative compounds described in pp. 127 to 137 of JP1987-215272A (JP-S62-215272A) can be used.

Examples of the fungicide include sodium dehydroacetate, sodium benzoate, sodium pyridinethion-1-oxide, p-hydroxybenzoic acid ethyl ester, 1,2-benzisothiazolin-3-one, and a salt thereof. These are preferably contained in an amount of 0.02% by mass to 1.00% by mass with respect to the total mass of the ink.

As the pH adjusting agent, a neutralizing agent (organic base or inorganic alkali) can be used. For the purpose of improving the storage stability of the ink for ink jet recording, it is preferable that the pH adjusting agent is added so that the ink for ink jet recording has a pH of 6 to 10, and it is more preferable that the pH adjusting agent is added so that the ink for ink jet recording has a pH of 7 to 10.

Examples of the surface tension adjuster include nonionic, cationic, or anionic surfactants. The surface tension of the ink for ink jet recording is preferably 25 mN/m to 70 mN/m, and more preferably 25 mN/m to 60 mN/m at 25° C. In addition, the viscosity of the ink for ink jet recording is preferably 30 mPa·s or less at 25° C. Further, it is more preferable to adjust the viscosity to 20 mPa·s or less.

Examples of the surfactant include anionic surfactants such as fatty acid salts, alkyl sulfates, alkylbenzenesulfonates, alkylnaphthalenesulfonates, dialkylsulfosuccinates, alkyl phosphates, naphthalenesulfonic acid formalin condensates, and polyoxyethylene alkyl sulfuric acid ester salts; nonionic surfactants such as polyoxyethylene alkyl ethers, polyoxyethylene alkyl allyl ethers, polyoxyethylene fatty acid esters, sorbitan fatty acid esters, polyoxyethylene sorbitan fatty acid esters, polyoxyethylene alkylamines, glycerin fatty acid esters, and oxyethyleneoxypropylene block copolymers. In addition, SURFYNOLS (Air Products and Chemicals, Inc.) which is an acetylene-based polyoxyethylene oxide surfactant is also preferably used. In addition, an amine oxide-type amphoteric surfactant such as N,N-dimethyl-N-alkylamine oxide is also preferable. Furthermore, surfactants mentioned in pp. 37 and 38 of JP1984-157636A (JP-S59-157636A) or Research Disclosure No. 308119 (1989) can also be used.

As the defoamer, a fluorine-based compound, a silicone-based compound, a chelating agent typified by ethylenediaminetetraacetic acid (EDTA), or the like can also be used as necessary.

In a case where the compound represented by Formula 1, the tautomer thereof, and the salt thereof is dispersed in an aqueous medium, it is preferable that colored fine particles containing the compound and an oil-soluble polymer are dispersed in the aqueous medium as described in JP1999-286637A (JP-H11-286637A), JP2001-240763A, JP2001-262039A, JP2001-247788A, and the like; or the compound represented by Formula 1, the tautomer thereof, and the salt thereof, which has been dissolved in a high-boiling organic solvent, are dispersed in the aqueous medium as described in JP2001-262018A, JP2001-240763A, JP2001-335734A, JP2002-80772A, and the like. As the specific method, the oil-soluble polymer, the high-boiling organic solvent, and the additive to be used, and the used amount thereof in the case of dispersing the compound represented by Formula 1, the tautomer thereof, and the salt thereof in an aqueous medium, those described in the above-described patent documents can be preferably used. Alternatively, the compound represented by Formula 1, the tautomer thereof, and the salt thereof may be dispersed in a fine particle state in a solid state. With the dispersion, a dispersing agent or a surfactant can be used. As a dispersion apparatus, a simple stirrer or impeller stirring system, an in-line stirring system, a mill system (for example, colloid mill, ball mill, sand mill, attritor, roll mill, agitator mill, and the like), an ultrasonic system, or a high-pressure emulsifying and dispersing system (high-pressure homogenizer; specific commercial devices include Gaulin homogenizer, microfluidizer, DeBEE2000, and the like) can be used. For the method for preparing the ink for ink jet recording described above, in addition to the above-described patents, details are described in JP1993-148436A (JP-H5-148436A), JP1993-295312A (JP-H5-295312A), JP1995-97541A (JP-H7-97541A), JP1995-82515A (JP-H7-82515A), JP1995-118584A (JP-H7-118584A), JP1999-286637A (JP-H11-286637A), and JP2001-271003A, which can be used to prepare the ink for ink jet recording, containing the coloring composition according to the embodiment of the present disclosure.

As the aqueous medium, a mixture containing water as a main component and to which a hydrophilic organic solvent is added can be used as desired.

Examples of the above-described hydrophilic organic solvent include alcohols (for example, methanol, ethanol, propanol, isopropanol, butanol, isobutanol, sec-butanol, t-butanol, pentanol, hexanol, cyclohexanol, or benzyl alcohol); polyhydric alcohols (for example, ethylene glycol, diethylene glycol, triethylene glycol, polyethylene glycol, propylene glycol, dipropylene glycol, polypropylene glycol, butylene glycol, hexanediol, pentanediol, glycerin, hexanetriol, and thiodiglycol); glycol derivatives (for example, ethylene glycol monomethyl ether, ethylene glycol monoethyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monomethyl ether, triethylene glycol monoethyl ether, or ethylene glycol monophenyl ether); amines (for example, ethanolamine, diethanolamine, triethanolamine, N-methyl diethanolamine, N-ethyl diethanolamine, morpholine, N-ethylmorpholine, ethylene diamine, diethylene triamine, triethylene tetramine, polyethyleneimine, or tetramethyl propylene diamine); and other polar solvents (for example, formamide, N,N-dimethyl formamide, N,N-dimethyl acetamide, dimethylsulfoxide, sulfolane, 2-pyrrolidone, N-methyl-2-pyrrolidone, N-vinyl-2-pyrrolidone, 2-oxazolidone, 1,3-dimethyl-2-imidazolidinone, acetonitrile, and acetone). Two or more kinds of the hydrophilic organic solvents may be used in combination.

In a case where the coloring composition according to the embodiment of the present disclosure is used as an ink for ink jet recording, the compound represented by Formula 1, the tautomer thereof, and the salt thereof are contained in an amount of preferably 0.2 parts by mass to 10 parts by mass and more preferably 1 part by mass to 6 parts by mass with respect to 100 parts by mass of the ink for ink jet recording.

In addition, other coloring agents may be used in combination in the ink for ink jet recording. In a case where two or more kinds of coloring agents are used in combination, it is preferable that the total content of the coloring agents is within the above-described range.

(Dyeing Method and Dyed Article)

The dyeing method according to the embodiment of the present disclosure is a dyeing method using the compound represented by Formula 1, the tautomer thereof, or the salt thereof, and is preferably a dyeing method using the coloring composition according to the embodiment of the present disclosure.

The dyed article according to the embodiment of the present disclosure contains the compound represented by Formula 1, the tautomer thereof, or the salt thereof.

As the dyeing method using the compound represented by Formula 1, the tautomer thereof, or the salt thereof, it is sufficient to use at least one kind selected from the group consisting of the compound represented by Formula 1, the tautomer thereof, and the salt thereof as a dye. For example, a method such as dipping, kneading, coating, printing, and ink jet printing can be used.

In addition, as the dyeing method according to the embodiment of the present disclosure, a known dyeing method can be used except that the compound represented by Formula 1, the tautomer thereof, or the salt thereof is used.

The dyed article according to the embodiment of the present disclosure may contain a pigment and/or a dye other than the compound represented by Formula 1, the tautomer thereof, and the salt thereof.

In addition, a dyed portion containing the compound represented by Formula 1, the tautomer thereof, or the salt thereof in the dyed article according to the embodiment of the present disclosure may be a part of the dyed article or the entire dyed article.

As an object to be dyed in the dyed article according to the embodiment of the present disclosure, natural fibers such as silk, cotton, and hemp; synthetic fibers such as nylon, polyester, acrylic and polyurethane; inorganic substances such as glass, metal, and ceramics; or paper such as plain paper, resin-coated paper, and ink jet recording paper can be used.

EXAMPLES

Hereinafter, the present disclosure will be described in detail with reference to examples, but the present disclosure is not limited thereto. In the present examples, "%" and "part" respectively indicate "% by mass" and "part by mass" unless otherwise specified.

Example 1: Synthesis of Exemplary Compound M-2 and Exemplary Compound D-2

A mixture of 4.4 g of 5-amino-3-methylthio-1,2,4-thiadiazole, 8.8 g of concentrated sulfuric acid, 4.2 g of water, and 20 mL of acetic acid was stirred under ice-cooling. A solution of 2.3 g of sodium nitrite and 4 mL of water was added dropwise to the mixture, the mixture was stirred for 1 hour, and 4.9 mL of acetic acid was added thereto to obtain a diazonium salt solution.

Separately, a mixture of 6.6 g of resorcinol (1,3-dihydroxybenzene) and 60 mL of methanol (MeOH) was prepared, the above-described diazonium salt solution was added dropwise thereto under ice-cooling, and the mixture was left as it was for 4 days. 60 mL of water was added to the reaction mixture, and the precipitated crystals were collected by filtration and washed with water and methanol. The obtained crystals were dried to obtain 6.6 g of Exemplary Compound M-2.

$^1$H-NMR (DMSO-$d_6$) δ=11.6 (br., 1H), 7.71 (d, 1H), 6.51 (dd, 1H), 6.46 (d, 1H), 2.67 (s, 3H)

A mixture of 2.3 g of concentrated sulfuric acid, 13.8 g of acetic acid (AcOH), and 5.9 g of 5-amino-1-methylpyrazole phosphate was stirred under ice-cooling, and 9.5 g of nitrosyl sulfate (43%) was added dropwise thereto. After stirring for 20 minutes, the diazonium salt obtained above was added dropwise to a mixture of 5.9 g of Exemplary Compound M-2, 6.5 g of sodium acetate (AcONa), and 60 mL of methanol under ice-cooling. After stirring at room temperature (20° C. to 25° C.; the same applies hereinafter) for 1 hour, the precipitated crystals were collected by filtration and washed with water and methanol. The obtained crystals were stirred in 50 mL of acetonitrile, collected by filtration, washed with acetonitrile, and dried to obtain 4.5 g of Exemplary Compound D-2.

$^1$H-NMR (CDCl$_3$) δ=15.0 (br., 1H), 7.51 (d, 1H), 7.31 (d, 1H), 6.56 (d, 1H), 6.53 (d, 1H), 4.06 (s, 3H), 2.67 (s, 3H)

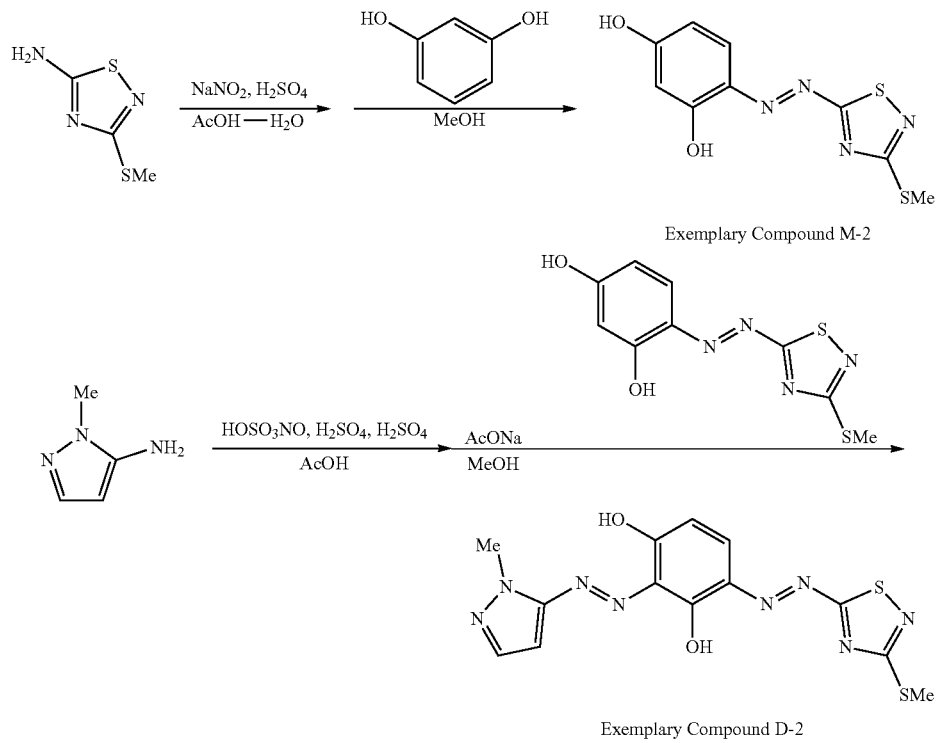

Maximum absorption wavelength (λmax): 492 nm, molar absorption coefficient ε: 2.63×10$^4$ (N,N-dimethylformamide (DMF))

<Evaluation 1: Dyeing of Ink Jet Paper with Exemplary Compound D-2>

62 mg of SURFYNOL 465 (manufactured by Nissin Chemical Co., Ltd.) was added to 100 mL of pure water to prepare a surfactant solution. 2.5 g of the above-described surfactant solution was added to and uniformly dissolved in a mixture of 50 mg of Exemplary Compound D-2 and 2.5 mL of 0.1 M (M=mol/L) sodium hydroxide aqueous solution. As a result, a coloring composition containing a salt of Exemplary Compound D-2 which is the compound according to the embodiment of the present disclosure was obtained.

The obtained coloring composition was applied onto an ink jet paper photo (manufactured by FUJIFILM Corporation) using a bar coater. A brown dyed article was obtained. L*, a*, and b* of the obtained dyed article were measured using i1 Pro (manufactured by X-Rite, Incorporated). The results are shown in Table 1 below.

Comparative Example 1: Dyeing of Ink Jet Paper with Acid Brown M

A coloring composition containing a salt of a comparative compound Acid Brown M was obtained in the same manner except for using Acid Brown M instead of Exemplary Compound D-2 described above.

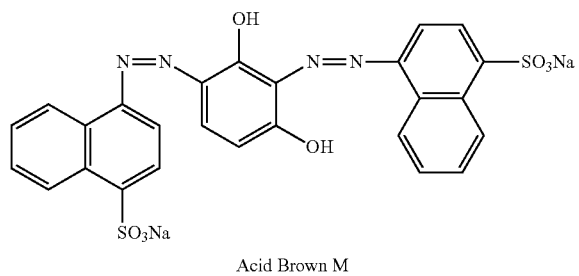

Acid Brown M

The obtained coloring composition was applied onto an ink jet paper photo (registered trademark, manufactured by FUJIFILM Corporation) using a bar coater. A reddish brown dyed article was obtained. L*, a*, and b* of the obtained dyed article were measured using i1 Pro (manufactured by X-Rite, Incorporated). The results are shown in Table 1 below.

TABLE 1

| Compound | | Brightness L* | Chroma saturation a* | b* |
|---|---|---|---|---|
| Example 1 | Exemplary Compound D-2 | 13.2 | 39.5 | 15.0 |
| Comparative Example 1 | Acid Brown M | 19.6 | 42.9 | 25.8 |

The column of compounds in Table 1 shows exemplary compounds used for evaluation of the dyeing.

Exemplary Compound D-2, which is the compound according to the embodiment of the present disclosure, had a hue with lower chroma saturation and brightness that the comparative compound Acid Brown M.

Example 2: Synthesis of Exemplary Compound M-11 and Exemplary Compound D-11

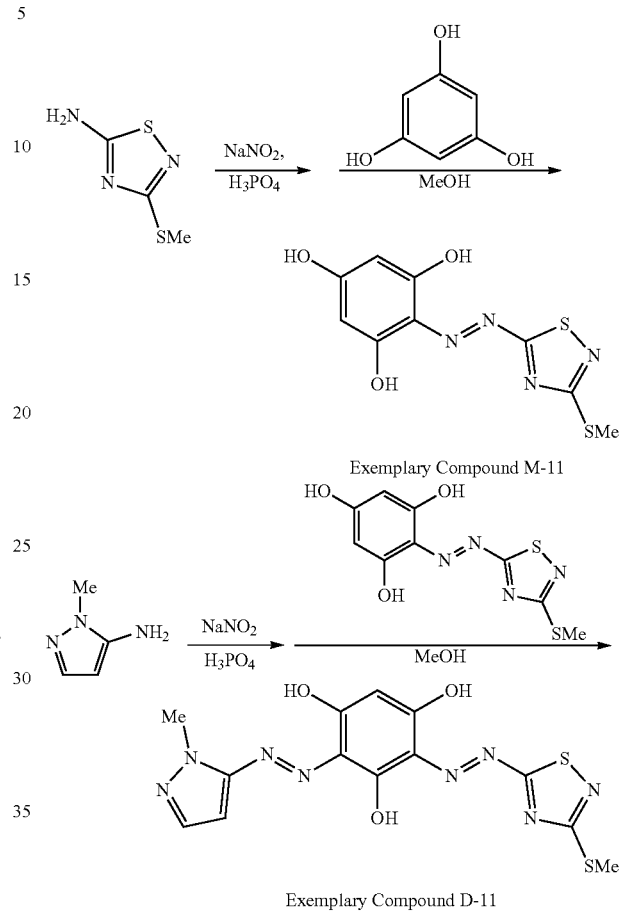

In a 200 mL three-neck flask, 14.7 g of 5-amino-3-methylthio-1,2,4-thiadiazole was dissolved in 80 mL of phosphoric acid (85%, manufactured by FUJIFILM Wako Pure Chemical Corporation), and the internal temperature was lowered to 0° C. 6.9 g of sodium nitrite (manufactured by FUJIFILM Wako Pure Chemical Corporation) was slowly added thereto up in portions while maintaining an internal temperature of 5° C. or lower. After completion of the addition, the mixture was stirred at an internal temperature of 0° C. to 5° C. for 1 hour to prepare a diazonium salt solution.

In another 500 mL three-neck flask, 12.6 g of 1,3,5-benzenetriol (manufactured by FUJIFILM Wako Pure Chemical Corporation) was dissolved in 200 mL of methanol, and the internal temperature was lowered to 5° C. The previously prepared diazonium salt solution was slowly added thereto while maintaining an internal temperature of 10° C. lower. After completion of the addition, the mixture was stirred at an internal temperature of 0° C. to 5° C. for 30 minutes, and then at 25° C. for 1 hour. The precipitated crystals were collected by filtration, washed with 200 mL of methanol times, and dried with a blast dryer at 50° C. for 6 hours to obtain powder crystals of Exemplary Compound M-11. Yield amount: 25.6 g (yield: 90%)

$^1$H-NMR (DMSO-d$_6$) δ=12.71 (br., 2H), 5.96 (s, 2H), 2.64 (s, 3H)

In a 200 mL three-neck flask, 9.8 g of 5-amino-1-methylpyrazole phosphate was dissolved in 80 mL of phosphoric acid (85%, manufactured by FUJIFILM Wako Pure Chemical Corporation), and the internal temperature was lowered to 0° C. 3.5 g of sodium nitrite (manufactured by FUJIFILM Wako Pure Chemical Corporation) was slowly added thereto up in portions while maintaining an internal temperature of 5° C. or lower. After completion of the addition, the mixture was stirred at an internal temperature of 0° C. to 5° C. for 1 hour to prepare a diazonium salt solution.

In another 500 mL three-neck flask, 14.2 g of Exemplary Compound M-11 was suspended and dispersed in 200 mL of methanol, and the internal temperature was lowered to 5° C. The previously prepared diazonium salt solution was slowly added thereto while maintaining an internal temperature of 10° C. lower. After completion of the addition, the mixture was stirred at an internal temperature of 0° C. to 5° C. for 30 minutes, and then at 25° C. for 1 hour. The precipitated crystals were collected by filtration and washed with 200 mL of methanol three times. The crystals were suspended and washed by heating with 100 mL of acetonitrile at 50° C., and dried with a blast dryer at 50° C. for 6 hours to obtain green glossy crystals of Exemplary Compound D-11. Yield amount: 16.2 g (yield: 83%)

$^1$H-NMR (DMSO-d$_6$) δ=10.2 (br., 2H), 7.31 (d, 1H), 6.66 (d, 1H), 6.40 to 6.59 (br, 1H), 5.79 (s, 1H), 4.10 (s, 3H), 2.56 (s, 3H)

λmax: 424 nm, ε: 2.44×10$^4$ (DMF)

The hue of Exemplary Compound D-11 was low in chroma saturation and brightness.

Example 3: Synthesis of Exemplary Compound N-100

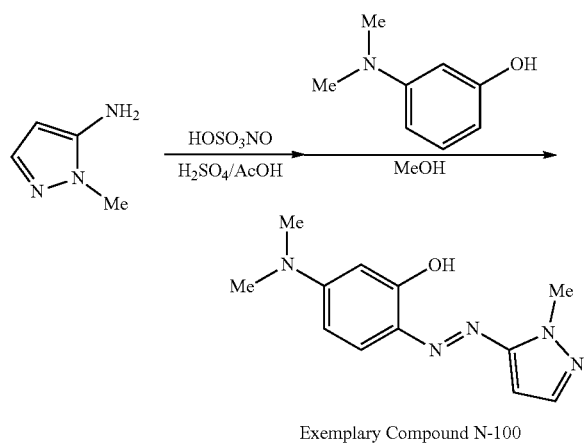

Exemplary Compound N-100

A mixture of 3.5 g of concentrated sulfuric acid, 20.7 g of acetic acid (AcOH), and 8.9 g of 5-amino-1-methylpyrazole phosphate was stirred under ice-cooling, and 14.3 g of nitrosyl sulfate (43%) was added dropwise thereto to obtain a diazonium salt solution. After stirring for 30 minutes, the diazonium salt solution obtained above was added dropwise to a mixture of 6.3 g of 3-hydroxy-N,N-dimethylaniline and 125 mL of methanol under ice-cooling. After stirring at room temperature (20° C. to 25° C.; the same applies hereinafter) for 1 hour, a 5% sodium hydrogen carbonate aqueous solution was added thereto until the pH reached 7 under ice-cooling, and the precipitated crystals were collected by filtration and spray-washed with water. The obtained crystals were dried to obtain 9.8 g of Exemplary Compound N-100.

$^1$H-NMR (CDCl$_3$) δ=7.7 (d, 1H), 7.5 (s, 1H), 6.5 (d, 2H), 6.2 (s, 2H), 4.0 (s, 3H), 3.1 (s, 6H)

Spectral characteristics in N,N-dimethylformamide were λmax: 470 nm and a molar absorption coefficient ε: 4.00×10$^4$.

In the case of 3-hydroxy-N,N-dimethylaniline, there were three reaction points where this reaction could occur in the diazo coupling reaction, but Exemplary Compound N-100 could be selectively obtained. As shown below, Exemplary Compound N-100 functioned as a valuable synthetic intermediate for obtaining Exemplary Compounds N-1, N-2, and N-6.

Example 4: Synthesis of Exemplary Compound N-1

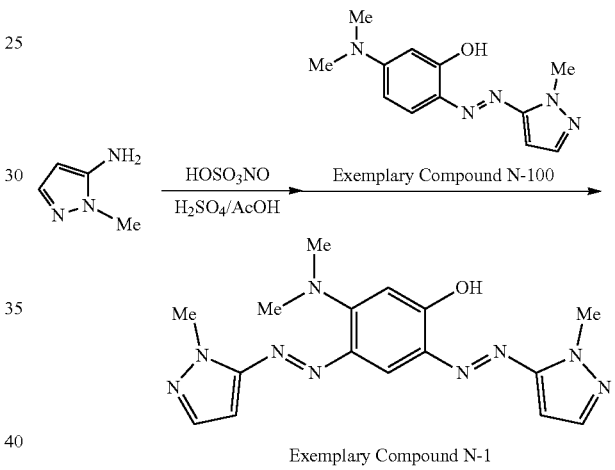

Exemplary Compound N-1

A mixture of 1.2 g of concentrated sulfuric acid, 6.9 g of acetic acid (AcOH), and 3 g of 5-amino-1-methylpyrazole phosphate was stirred under ice-cooling, and 4.8 g of nitrosyl sulfate (43%) was added dropwise thereto to obtain a diazonium salt solution. After stirring for 30 minutes, the diazonium salt solution obtained above was added dropwise to a mixture of 3.1 g of an intermediate A and 60 mL of methanol under ice-cooling. After stirring at room temperature (20° C. to 25° C.; the same applies hereinafter) for 1 hour, a 5% sodium hydrogen carbonate aqueous solution was added thereto until the pH reached 7 under ice-cooling, and the precipitated crystals were collected by filtration and spray-washed with water. The obtained crystals were dried and purified by silica gel chromatography to obtain 2.0 g of Exemplary Compound N-1.

$^1$H-NMR (CDCl$_3$) δ=12.7 (s, 1H), 8.2 (s, 1H), 7.5 (d, 2H), 6.56 (d, 2H), 6.35 (s, 1H), 4.3 (s, 3H), 4.1 (s, 3H), 3.3 (s, 6H)

Spectral characteristics in N,N-dimethylformamide were λmax1: 521 nm and a molar absorption coefficient ε: 2.03×10$^4$; λmax2: 442 nm and a molar absorption coefficient ε: 2.13×10$^4$; and λmax3: 347 nm and a molar absorption coefficient ε: 2.13×10$^4$.

Example 5: Synthesis of Exemplary Compound N-2 and Exemplary Compound N-6

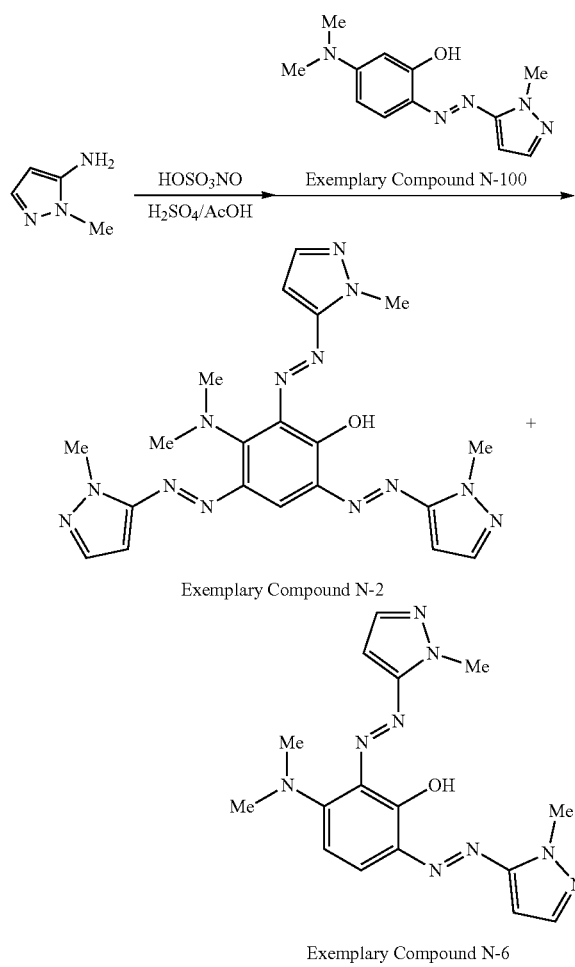

Exemplary Compound N-2

Exemplary Compound N-6

A mixture of 3.0 g of concentrated sulfuric acid, 17.3 g of acetic acid (AcOH), and 7.5 g of 5-amino-1-methylpyrazole phosphate was stirred under ice-cooling, and 12.0 g of nitrosyl sulfate (43%) was added dropwise thereto to obtain a diazonium salt solution. After stirring for 30 minutes, the diazonium salt solution obtained above was added dropwise to a mixture of 3.1 g of Exemplary Compound N-100 and 60 mL of methanol under ice-cooling. After stirring at room temperature (20° C. to 25° C.; the same applies hereinafter) for 1 hour, a 5% sodium hydrogen carbonate aqueous solution was added thereto until the pH reached 7 under ice-cooling, and the precipitated crystals were collected by filtration and spray-washed with water. The obtained crystals were dried and purified by silica gel chromatography to obtain 2.5 g of Exemplary Compound N-2 and 1.0 g of Exemplary Compound N-6.

($^1$H-NMR (CDCl$_3$))

Exemplary Compound N-2:

δ=14.9 (s, 1H), 8.6 (s, 1H), 7.6 (d, 3H), 6.56 (d, 2H), 6.35 (s, 1H), 4.3 (s, 3H), 4.2 (s, 3H), 4.1 (s, 3H), 3.5 (s, 6H)

Exemplary Compound N-6:

δ=14.7 (s, 1H), 7.9 (d, 1H), 7.5 (d, 2H), 6.6 (d, 2H), 6.4 (d, 2H), 4.2 (s, 3H), 4.1 (s, 3H), 3.4 (s, 6H)

(Spectral Characteristics in N,N-Dimethylformamide)

Exemplary Compound N-1:

λmax1: 521 nm, molar absorption coefficient ε: 2.03×10$^4$

λmax2: 442 nm, molar absorption coefficient ε: 2.13×10$^4$

λmax3: 347 nm, molar absorption coefficient ε: 2.13×10$^4$

Exemplary Compound N-2:

λmax1: 600 nm, molar absorption coefficient ε: 1.70×10$^4$

λmax2: 496 nm, molar absorption coefficient ε: 2.13×10$^4$

λmax3: 419 nm, molar absorption coefficient ε: 2.70×10$^4$

Exemplary Compound N-6:

λmax1: 449 nm, molar absorption coefficient ε: 3.45×10$^4$

λmax2: 420 nm, molar absorption coefficient ε: 3.35×10$^4$

<Evaluation 2: Dyeing of Ink Jet Paper with Exemplary Compound N-1, N-2, or N-6>

(1) Production of Coloring Composition Containing Salt of Exemplary Compound N-1

62 mg of SURFYNOL 465 (manufactured by Nissin Chemical Co., Ltd.) was added to 100 mL of pure water to prepare a surfactant solution. 2.5 g of the above-described surfactant solution was added to and uniformly dissolved in a mixture of 47 mg of Exemplary Compound N-1 and 2.5 mL of 0.1 M (M=mol/L) sodium hydroxide aqueous solution. As a result, a coloring composition containing a salt of Exemplary Compound N-1 which is the compound according to the embodiment of the present disclosure was obtained.

(2) Production of Coloring Composition Containing Salt of Exemplary Compound N-2

A coloring composition containing a salt of Exemplary Compound N-2, which is the compound according to the embodiment of the present disclosure, was obtained in the same manner except for using 61 mg of Exemplary Compound N-2 instead of Exemplary Compound N-1 described above.

(3) Production of Coloring Composition Containing Salt of Exemplary Compound N-6

A coloring composition containing a salt of Exemplary Compound N-6, which is the compound according to the embodiment of the present disclosure, was obtained in the same manner except for using 47 mg of Exemplary Compound N-6 instead of Exemplary Compound N-1 described above.

Each of the coloring compositions obtained above was applied onto an ink jet paper photo (manufactured by FUJIFILM Corporation) using a bar coater. A brown dyed article was obtained. L*, a*, and b* of the obtained dyed article were measured using i1 Pro (manufactured by X-Rite, Incorporated).

The above evaluation results are shown in Table 2 below. Table 2 also shows the evaluation results of Comparative Example 1.

TABLE 2

| | Compound | Brightness L* | Chroma saturation a* | b* |
|---|---|---|---|---|
| Example 4 | Exemplary Compound N-1 | 13.9 | 15.7 | 6.7 |
| Example 5 | Exemplary Compound N-2 | 12.7 | 31.9 | 21.7 |
| | Exemplary Compound N-6 | 10.2 | 3.2 | 9.4 |
| Comparative Example 1 | Acid Brown M | 19.6 | 42.9 | 25.8 |

The column of compounds in Table 2 shows exemplary compounds used for evaluation of the coloring compositions.

Exemplary Compounds N-1, N-2, and N-6, which are the compound according to the embodiment of the present disclosure, had a hue with lower chroma saturation and brightness that the comparative compound Acid Brown M.

The disclosure of JP2020-173290 filed on Oct. 14, 2020 and the disclosure of JP2020-217653 filed on Dec. 25, 2020 are incorporated in the present specification by reference. All documents, patent applications, and technical standards described in the present specification are herein incorporated by reference to the same extent that each individual document, patent application, or technical standard was specifically and individually indicated to be incorporated by reference.

What is claimed is:

1. A compound represented by Formula 1, a tautomer of the compound, or a salt of the compound or the tautomer,

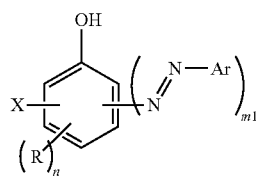

Formula 1 wherein, in Formula 1, X— represents $R^1O$—, $R^{2a}R^{2b}N$—, or $R^3S$—, $R^1$, $R^{2a}$, and $R^{2b}$ each independently represent a hydrogen atom or an alkyl group, $R^3$ represents an alkyl group, in a case where X— is $R^{2a}R^{2b}N$—, $R^{2a}$ and $R^{2b}$ may be the same or different from each other and $R^{2a}$ and $R^{2b}$ may be bonded to each other to form a nitrogen-containing hetero ring, R's each independently represent a substituent, n represents 0, 1, 2, or 3, in a case where n represents 2 or 3, R's may be the same or different from each other, Ar represents an aromatic hydrocarbon group or a heterocyclic group, m1 represents 2 or 3, and in a case where m1 represents 2 or 3, Ar's may be the same or different from each other, provided that at least one of Ar's is a heterocyclic group, and wherein the at least one of Ar's is a group represented by any of the group consisting of Formulae (A-1) to (A-27) and (A-28):

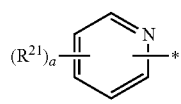
(A-1)

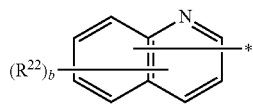
(A-2)

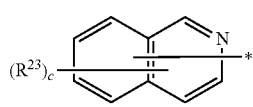
(A-3)

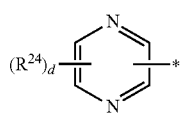
(A-4)

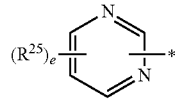
(A-5)

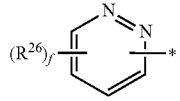
(A-6)

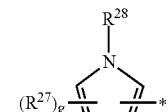
(A-7)

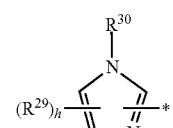
(A-8)

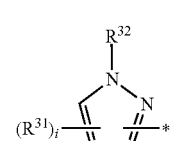
(A-9)

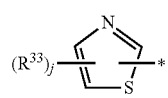
(A-10)

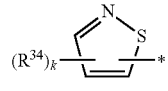
(A-11)

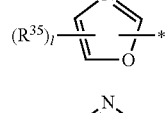
(A-12)

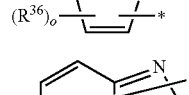
(A-13)

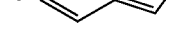
(A-14)

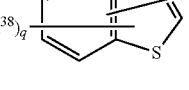
(A-15)

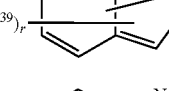
(A-16)

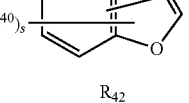
(A-17)

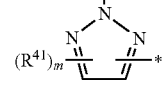
(A-18)

-continued

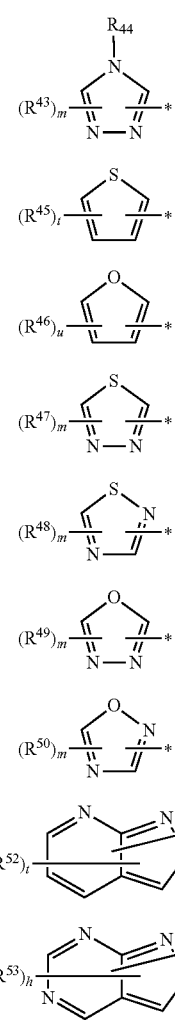

(A-19)
(A-20)
(A-21)
(A-22)
(A-23)
(A-24)
(A-25)
(A-27)
(A-28)

in Formulae (A-1) to (A-25), (A-27) and (A-28), * represents a position bonded to an azo group in Formula 1, $R^{21}$ to $R^{27}$, $R^{29}$, $R^{31}$, and $R^{33}$ to $R^{53}$ each independently represent a halogen atom, an alkyl group, an aryl group, a heterocyclic group, a cyano group, a hydroxy group, a nitro group, an alkoxy group, an aryloxy group, an amino group, an acylamino group, an aminocarbonylamino group, an alkoxycarbonylamino group, an alkylsulfonylamino group, an arylsulfonylamino group, an alkylthio group, an arylthio group, a heterocyclicthio group, a sulfamoyl group, an alkylsulfonyl group, an arylsulfonyl group, an acyl group, an alkoxycarbonyl group, or a carbamoyl group, $R^{28}$ $R^{30}$, and $R^{32}$ each independently represent a hydrogen atom, a halogen atom, an alkyl group, an aryl group, a heterocyclic group, a cyano group, a hydroxy group, a nitro group, an alkoxy group, an aryloxy group, an amino group, an acylamino group, an aminocarbonylamino group, an alkoxycarbonylamino group, an alkylsulfonylamino group, an arylsulfonylamino group, an alkylthio group, an arylthio group, a heterocyclicthio group, a sulfamoyl group, an alkylsulfonyl group, an arylsulfonyl group, an acyl group, an alkoxycarbonyl group, or a carbamoyl group, adjacent groups among $R^{21}$ to $R^{53}$ may be bonded to each other to form a saturated or unsaturated 5- or 6-membered ring structure, a, p, q, r, and s represent an integer of 0 to 4, b and c represent an integer of 0 to 6, d, e, f, g, t, and u represent an integer of 0 to 3, h, i, j, k, l, and o represent an integer of 0 to 2, w represents an integer of 0 to 5, m represents 0 or 1, and two or more groups represented by $R^{21}$ to $R^{53}$ in a same molecule may be the same or different from each other.

2. The compound, the tautomer of the compound, or the salt of the compound or the tautomer according to claim 1, wherein m1 is 2.

3. The compound, the tautomer of the compound, or the salt of the compound or the tautomer according to claim 1, wherein a bonding position of X— is a meta-position with respect to a hydroxy group.

4. The compound, the tautomer of the compound, or the salt of the compound or the tautomer according to claim 1, wherein R is a halogen atom, a hydroxy group, an alkyl group, an aryl group, an alkoxy group, an aryloxy group, an acyl group, an alkoxycarbonyl group, a carboxy group, a carbamoyl group, a cyano group, an acylamino group, a sulfonylamino group, an alkylthio group, an arylthio group, an alkylsulfonyl group, an arylsulfonyl group, or a sulfo group.

5. The compound, the tautomer of the compound, or the salt of the compound or the tautomer according to claim 1, wherein the compound, the tautomer of the compound, or the salt of the compound or the tautomer is a bisazo coloring agent.

6. A coloring composition comprising:
the compound, the tautomer of the compound, or the salt of the compound or the tautomer according to claim 1.

7. The coloring composition according to claim 6, further comprising:
an aqueous solvent.

8. A dyeing method of dyeing an article, comprising utilizing the coloring composition according to claim 6.

9. A dyed article comprising:
the compound, the tautomer of the compound, or the salt of the compound or the tautomer according to claim 1.

10. A method for producing the compound, the tautomer of the compound, or the salt of the compound or the tautomer according to claim 1, the method comprising:
a step of reacting a diazonium salt represented by Formula 5' with a compound represented by Formula 6 to obtain a compound represented by Formula 7',

Formula 5'

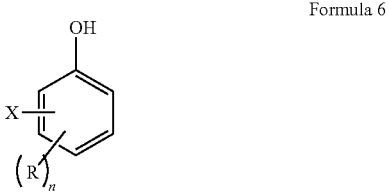

Formula 6

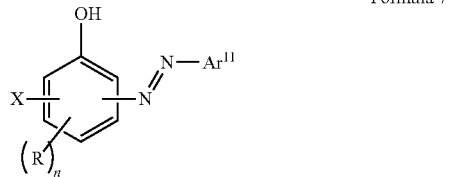

Formula 7' in Formula 5', Formula 6, and Formula 7', $Ar^{11}$ represents a heterocyclic group, R represents a substituent, X— represents $R^1O$—, $R^{2a}R^{2b}N$—, or $R^3S$—, $R^1$, $R^{2a}$, and $R^{2b}$ each independently represent a hydrogen atom or an alkyl group, $R^3$ represents an alkyl group, n represents 0, 1, 2, or 3, and in a case where n represents 2 or 3, R's may be the same or different from each other.

11. A method for producing the compound, the tautomer of the compound, or the salt of the compound or the tautomer according to claim 1, the method comprising:

a step of reacting a diazonium salt represented by Formula 5 with a compound represented by Formula 6 to obtain a compound represented by Formula 7; and a step of reacting the obtained compound represented by Formula 7 with a diazonium salt represented by Formula 8, to produce the compound according to Formula 1, the tautomer of the compound, or the salt,

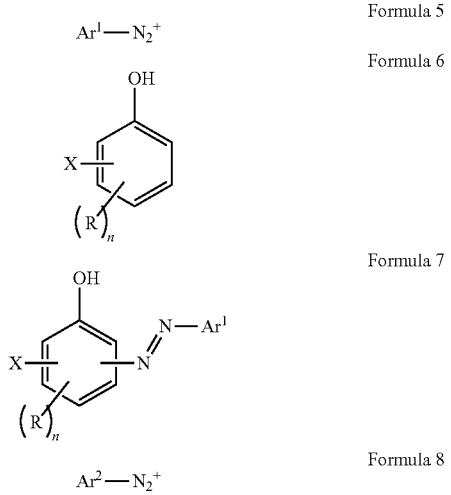

Formula 5

Formula 6

Formula 7

Formula 8 wherein, in Formulae 5 to 8, $Ar^1$ and $Ar^2$ each independently represent an aromatic hydrocarbon group or a heterocyclic group, R represents a substituent, X— represents $R^1O$—, $R^{2a} R^{2b}N$—, or $R^3S$—, $R^1$, $R^{2a}$, and $R^{2b}$ each independently represent a hydrogen atom or an alkyl group, $R^3$ represents an alkyl group, n represents 0, 1, 2, or 3, and in a case where n represents 2 or 3, R's may be the same or different from each other, provided that $Ar^1$ and $Ar^2$ are not simultaneously aromatic hydrocarbon groups.

12. A method for producing the compound, the tautomer of the compound, or the salt of the compound or the tautomer according to claim 1, the method comprising:

a step of reacting a diazonium salt represented by Formula 5 with a compound represented by Formula 10 to obtain a compound represented by Formula 11; and a step of reacting the obtained compound represented by Formula 11 with a diazonium salt represented by Formula 8 to obtain a compound represented by Formula 12,

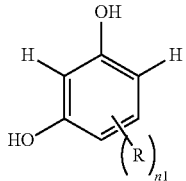

Formula 5

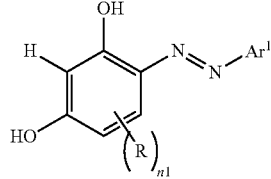

Formula 10

Formula 11

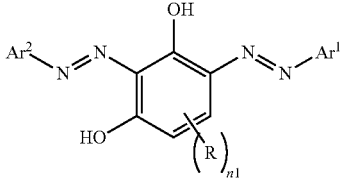

Formula 8

Formula 12 in Formula 5, Formula 8, and Formulae 10 to 12, $Ar^1$ and $Ar^2$ each independently represent an aromatic hydrocarbon group or a heterocyclic group, R represents a substituent, n1 represents 0, 1, or 2, and in a case where n1 represents 2, R's may be the same or different from each other, provided that $Ar^1$ and $Ar^2$ are not simultaneously aromatic hydrocarbon groups.

13. A method for producing a compound represented by Formula 1, a tautomer of the compound, or a salt of the compound or the tautomer,

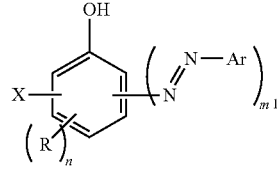

Formula 1 wherein, in Formula 1, X— represents $R^1O$—, $R^{2a}R^{2b}N$—, or $R^3S$—, $R^1$, $R^{2a}$, and $R^{2b}$ each independently represent a hydrogen atom or an alkyl group, $R^3$ represents an alkyl group, in a case where X— is $R^{2a}R^{2b}N$—, $R^{2a}$ and $R^{2b}$ may be the same or different from each other and $R^{2a}$ and $R^{2b}$ may be bonded to each other to form a nitrogen-containing hetero ring, R's each independently represent a substituent, n represents 0, 1, 2, or 3, in a case where n represents 2 or 3, R's may be the same or different from each other, Ar represents an aromatic hydrocarbon group or a heterocyclic group, m1 represents 2 or 3, and in a case where m1 represents 2 or 3, Ar's may be the same or different from each other, provided that at least one of Ar's is a heterocyclic group, the method comprising:

a step of reacting a diazonium salt represented by Formula 5 with a compound represented by Formula 13 to obtain a compound represented by Formula 14; and a step of reacting the obtained compound represented by Formula 14 with a diazonium salt represented by Formula 8 to obtain a compound represented by Formula 15, Formula 5

Ar$^1$—N$_2^+$

Formula 13

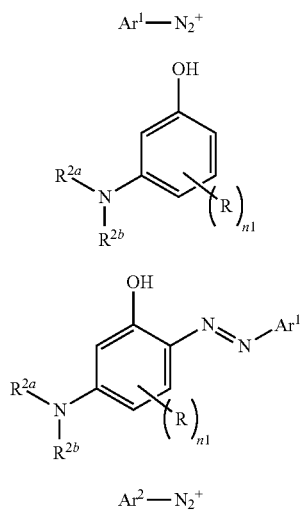

Formula 14

Formula 8

Formula 15

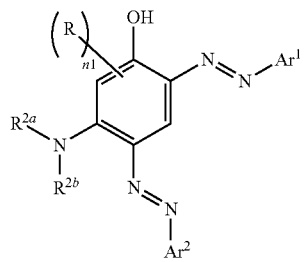

in Formula 5, Formula 8, and Formulae 13 to 15, Ar$^1$ and Ar$^2$ each independently represent an aromatic hydrocarbon group or a heterocyclic group, R$^{2a}$ and R$^{2b}$ each independently represent a hydrogen atom or an alkyl group, R$^{2a}$ and R$^{2b}$ may be the same or different from each other, R$^{2a}$ and R$^{2b}$ may be bonded to each other to form a nitrogen-containing hetero ring, R represents a substituent, n1 represents 0, 1, or 2, and in a case where n1 represents 2, R's may be the same or different from each other, provided that Ar$^1$ and Ar$^2$ are not simultaneously aromatic hydrocarbon groups.

* * * * *